(12) United States Patent
Xie et al.

(10) Patent No.: US 7,072,046 B2
(45) Date of Patent: Jul. 4, 2006

(54) OPTICAL IMAGING SYSTEM AND OPTICAL IMAGING DETECTION METHOD

(75) Inventors: Tianyu Xie, Shibuya-ku (JP); Akio Uchiyama, Shibuya-ku (JP); Atsushi Okawa, Shibuya-ku (JP)

(73) Assignee: Olympus Corporation (JP)

( * ) Notice: Subject to any disclaimer, the term of this patent is extended or adjusted under 35 U.S.C. 154(b) by 268 days.

(21) Appl. No.: 10/633,832

(22) Filed: Aug. 4, 2003

(65) Prior Publication Data

US 2004/0085543 A1    May 6, 2004

Related U.S. Application Data

(63) Continuation of application No. PCT/JP02/04385, filed on May 2, 2002.

(30) Foreign Application Priority Data

May 9, 2001   (JP)   ............................ 2001-139136
Apr. 17, 2002  (JP)   ............................ 2002-115399

(51) Int. Cl.
*G01B 9/02* (2006.01)

(52) U.S. Cl. .................................................. 356/479
(58) Field of Classification Search ................ 356/479
See application file for complete search history.

(56) References Cited

U.S. PATENT DOCUMENTS

| 5,807,247 | A  | * | 9/1998 | Merchant et al. ............ 600/310 |
| 6,069,698 | A  | * | 5/2000 | Ozawa et al. ................ 356/511 |
| 6,903,761 | B1 | * | 6/2005 | Abe et al. ..................... 348/65 |
| 2004/0181148 | A1 | * | 9/2004 | Uchiyama et al. .......... 600/425 |

FOREIGN PATENT DOCUMENTS

| JP | 62006593 A | * | 1/1987 |
| JP | 01270842 A | * | 10/1989 |
| JP | 11148897 A | * | 6/1999 |
| JP | 2001008199 A | * | 1/2001 |

* cited by examiner

*Primary Examiner*—Constantine Hannaher
(74) *Attorney, Agent, or Firm*—Ostrolenk, Faber, Gerb & Soffen, LLP

(57) ABSTRACT

An attachment 10 that is proximal to an optical probe 9 includes probe information holding means 39 that holds probe information such as a scanning technique and an optical path length or the like. When the optical probe 9 is connected (attached) to an observing device 6, probe information detecting means included in the observing device 6 automatically detects the probe information held in the optical probe. Based on the detected probe information, a scanning technique and an optical path length of reference light are set to values suitable to an actually connected optical probe 9.

28 Claims, 48 Drawing Sheets

FIG.8
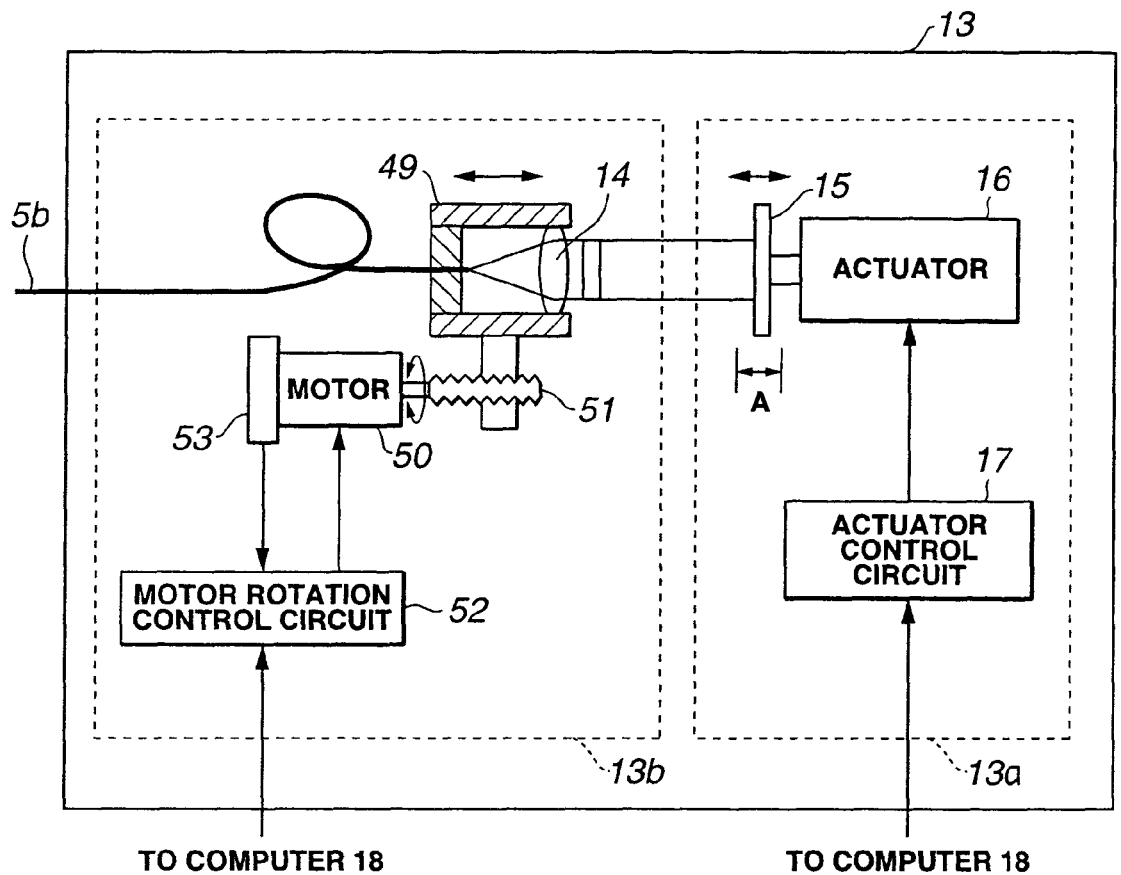
TO COMPUTER 18        TO COMPUTER 18
FIG.9A          FIG.9B
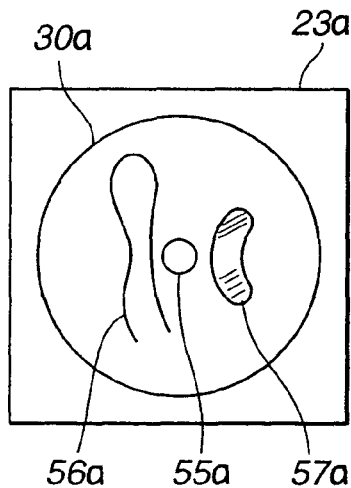 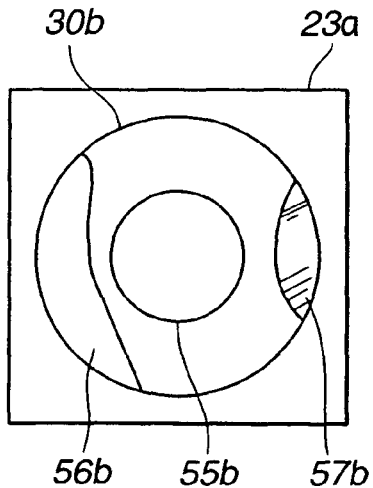

FIG.30A

| TYPE (S/N) | AMOUNT OF RETURN LIGHT | OPTICAL LENGTH | NUMERICAL APERTURE (NA) | FOCAL LENGTH | RESOLUTION | APPROPRIATE WAVELENGTH OF LIGHT EMANATING FROM LIGHT SOURCE | NOISE LEVEL | DIAMETER OF LIGHT SPOT |
|---|---|---|---|---|---|---|---|---|

FIG.30B

| X PHASE CORRECTION COEFFICIENT ($\theta x$) | X DRIVING VOLTAGE (Vx) | X DRIVING FREQUENCY (fx) | X OFFSET VOLTAGE (Vxo) | X FIELD OF VIEW (lx) | KIND OF X DRIVING WAVE | X IMAGE RANGE (Px) | X SCANNING TECHNIQUE (X=···) |
|---|---|---|---|---|---|---|---|

FIG.30C

| Y PHASE CORRECTION COEFFICIENT ($\theta y$) | Y DRIVING VOLTAGE (Vy) | Y DRIVING FREQUENCY (fy) | Y OFFSET VOLTAGE (Vyo) | Y FIELD OF VIEW (ly) | KIND OF Y DRIVING WAVE | Y IMAGE RANGE (Py) | Y SCANNING TECHNIQUE (Y=···) |
|---|---|---|---|---|---|---|---|

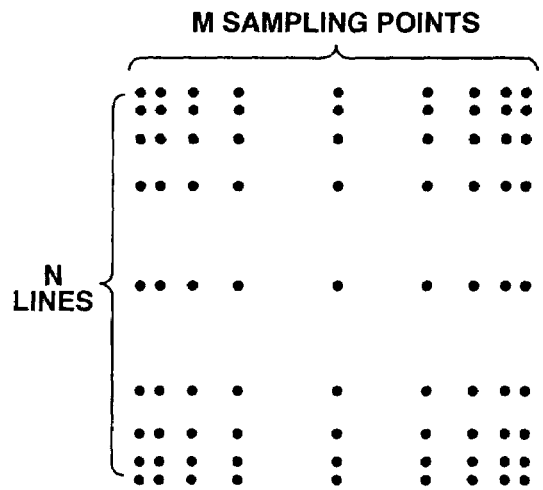
FIG.35A
M SAMPLING POINTS
N LINES
INTERPOLATION
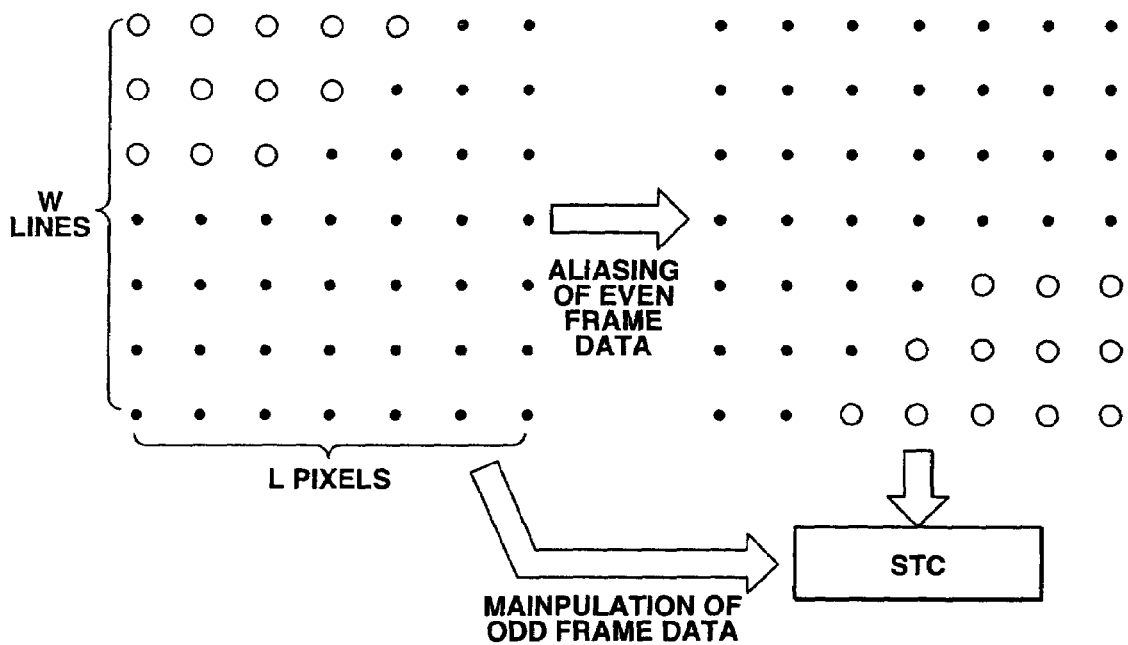
FIG.35B
W LINES
L PIXELS
FIG.35C
ALIASING OF EVEN FRAME DATA
MAINPULATION OF ODD FRAME DATA
STC

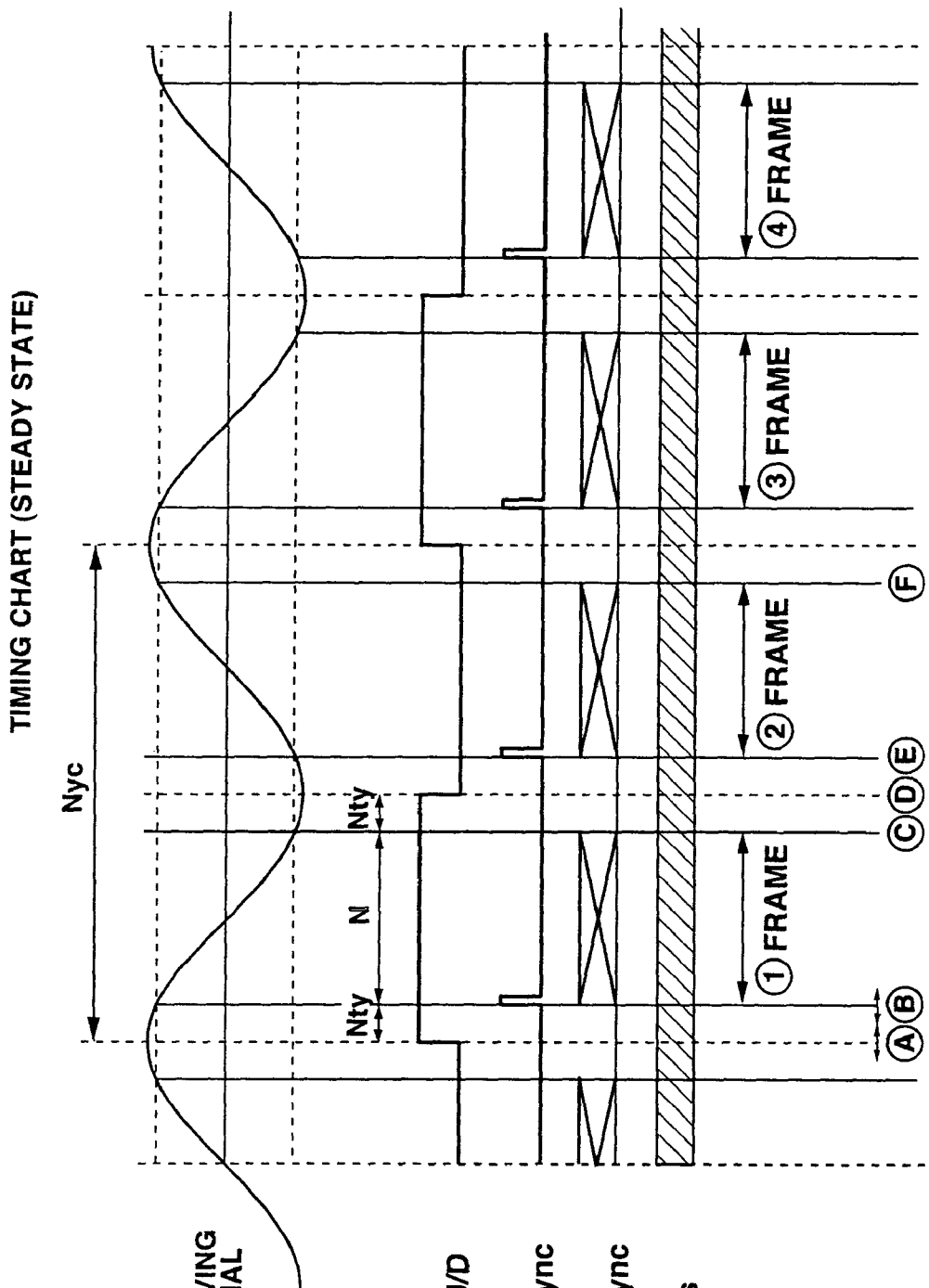

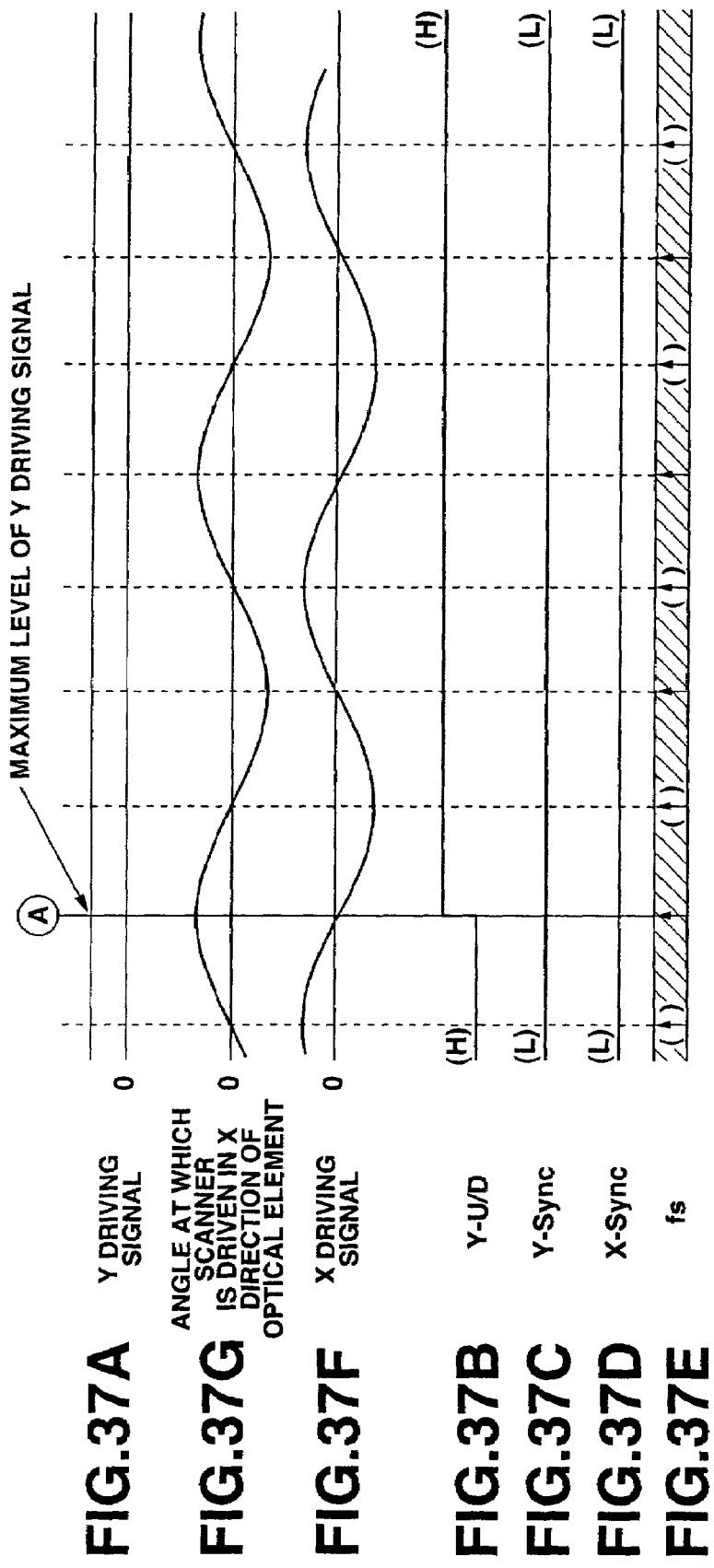

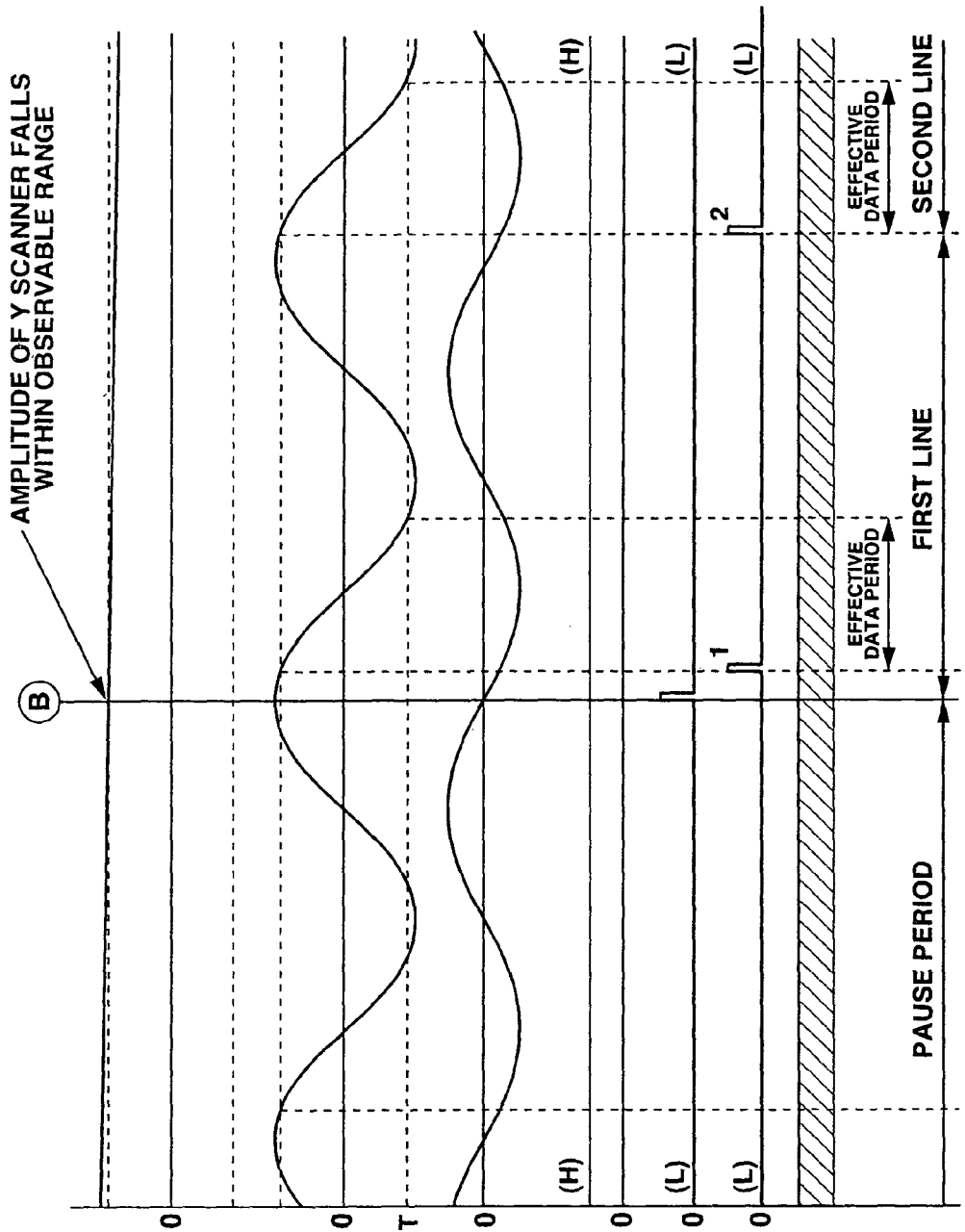

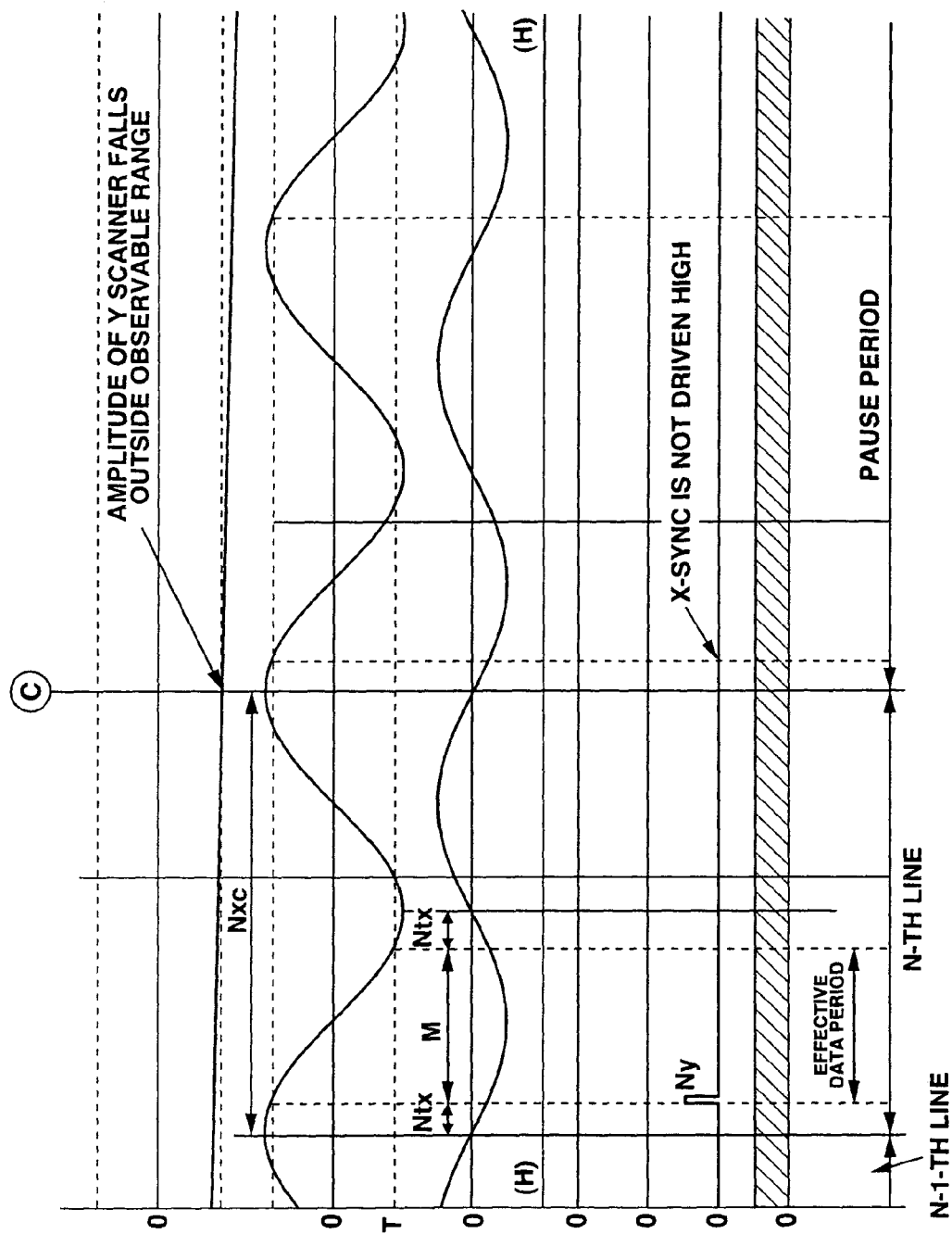

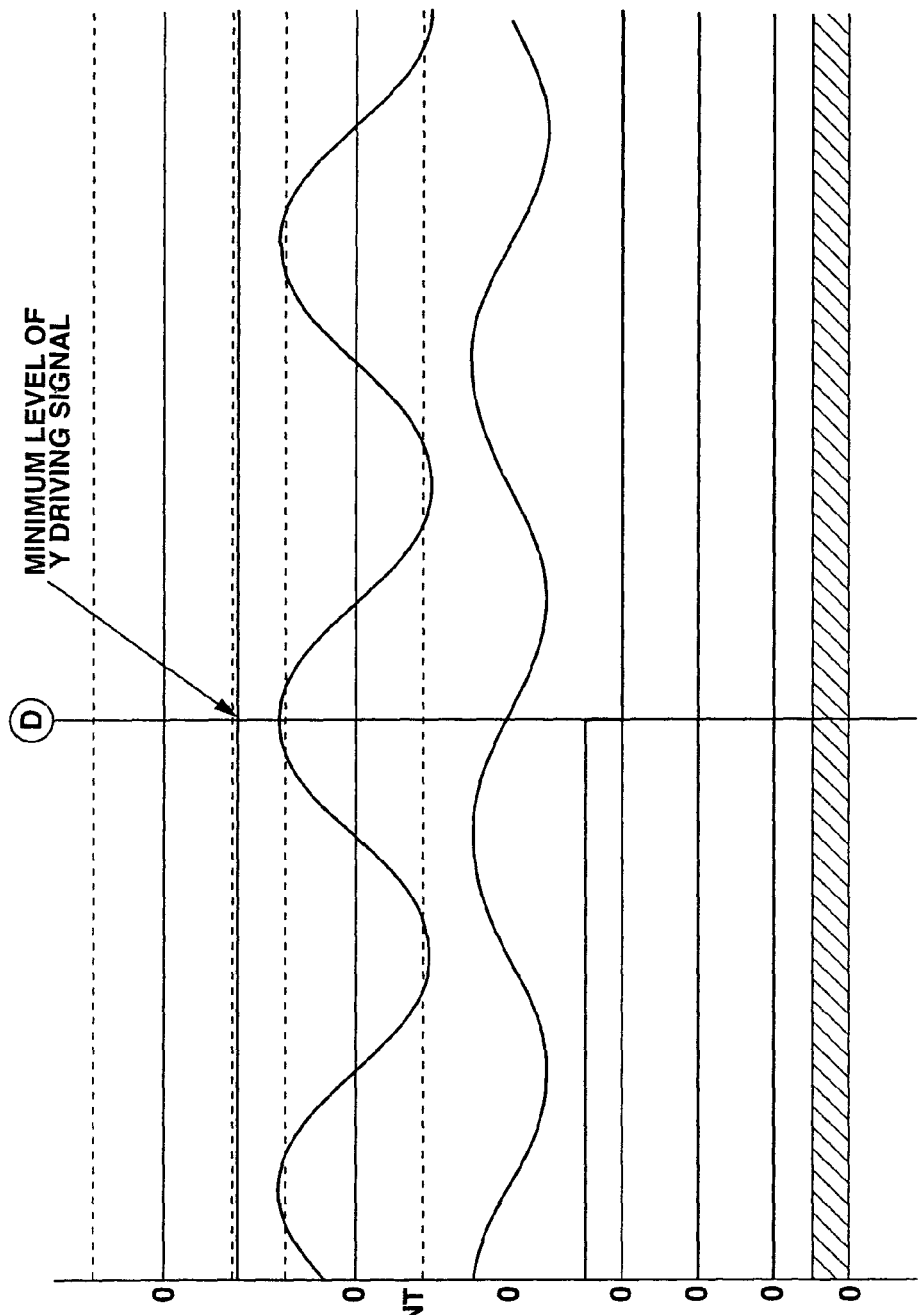

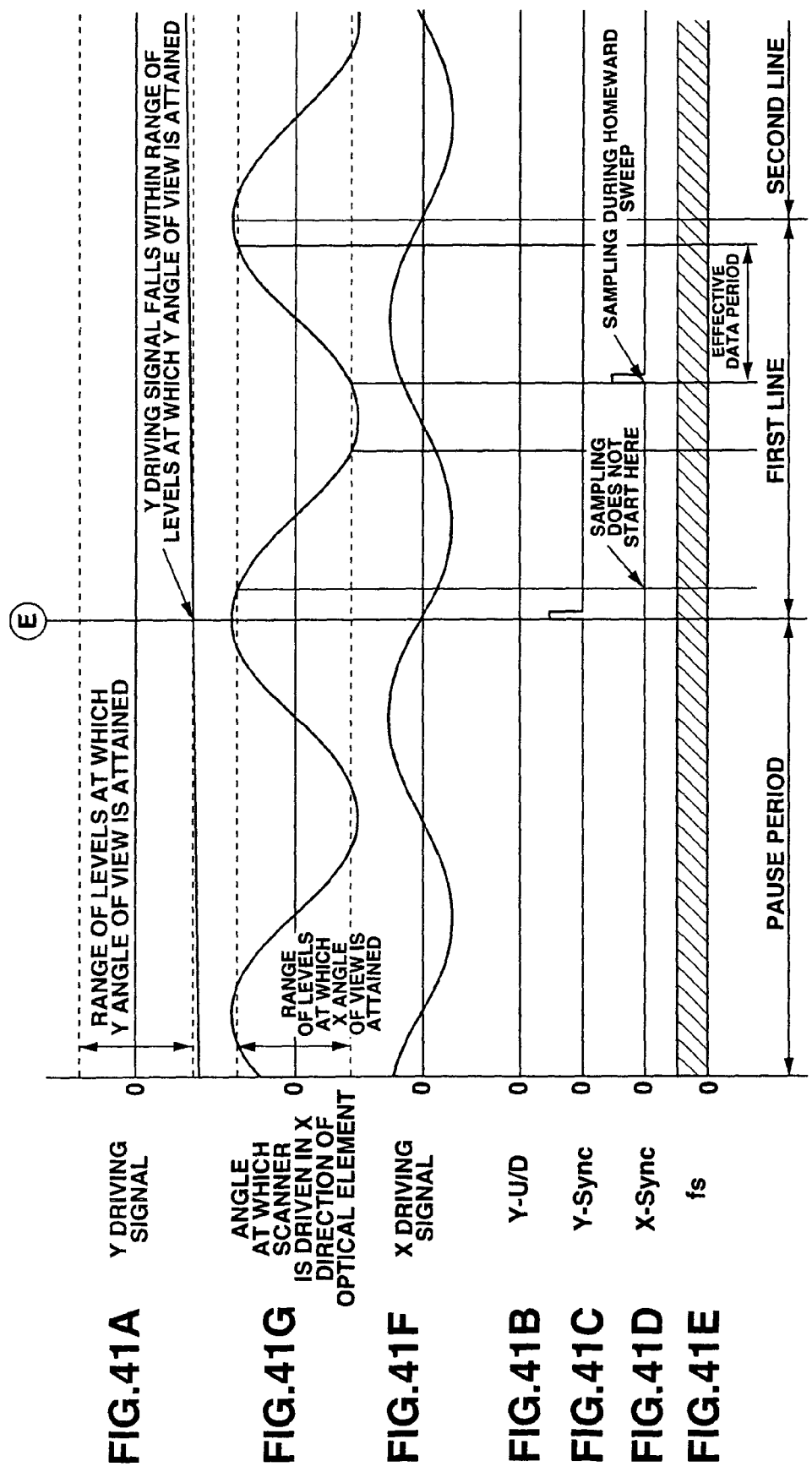

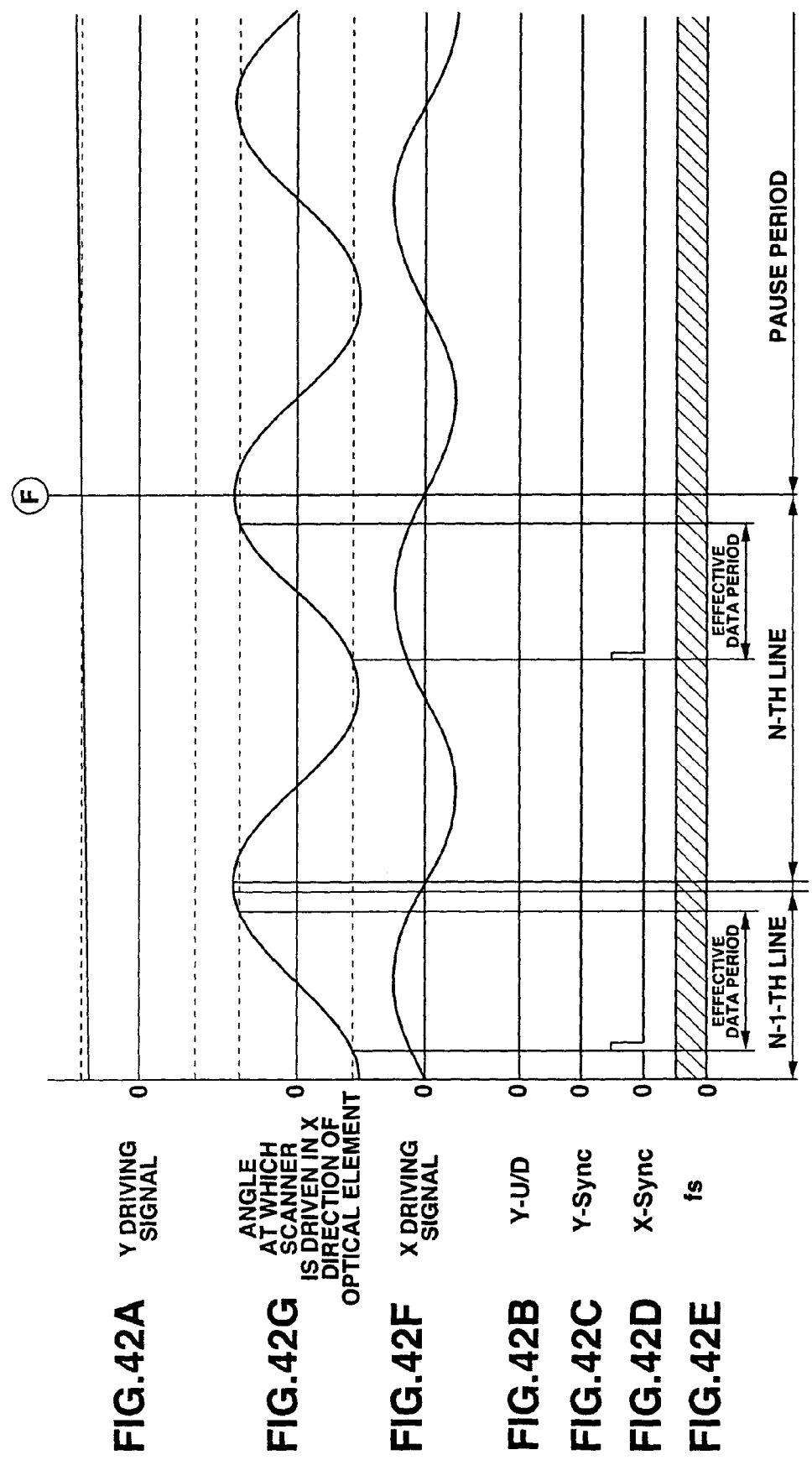

FOR WHOLE OF ONE SPECIFIC FRAME

FOR ALL OF PLURALITY OF CONSECUTIVE FRAMES

FOR PART OF PLURALITY OF FRAMES CHOSEN EVERY SPECIFIC NUMBER OF FRAMES

FOR SPECIFIC AREA IN ONE SPECIFIC FRAME

FOR SPECIFIC AREAS IN PLURALITY OF CONSECUTIVE FRAMES

FOR SPECIFIC AREAS IN PART OF PLURALITY OF FRAMENS CHOSEN EVERY SPECIFIC NUMBER OF FRAMES

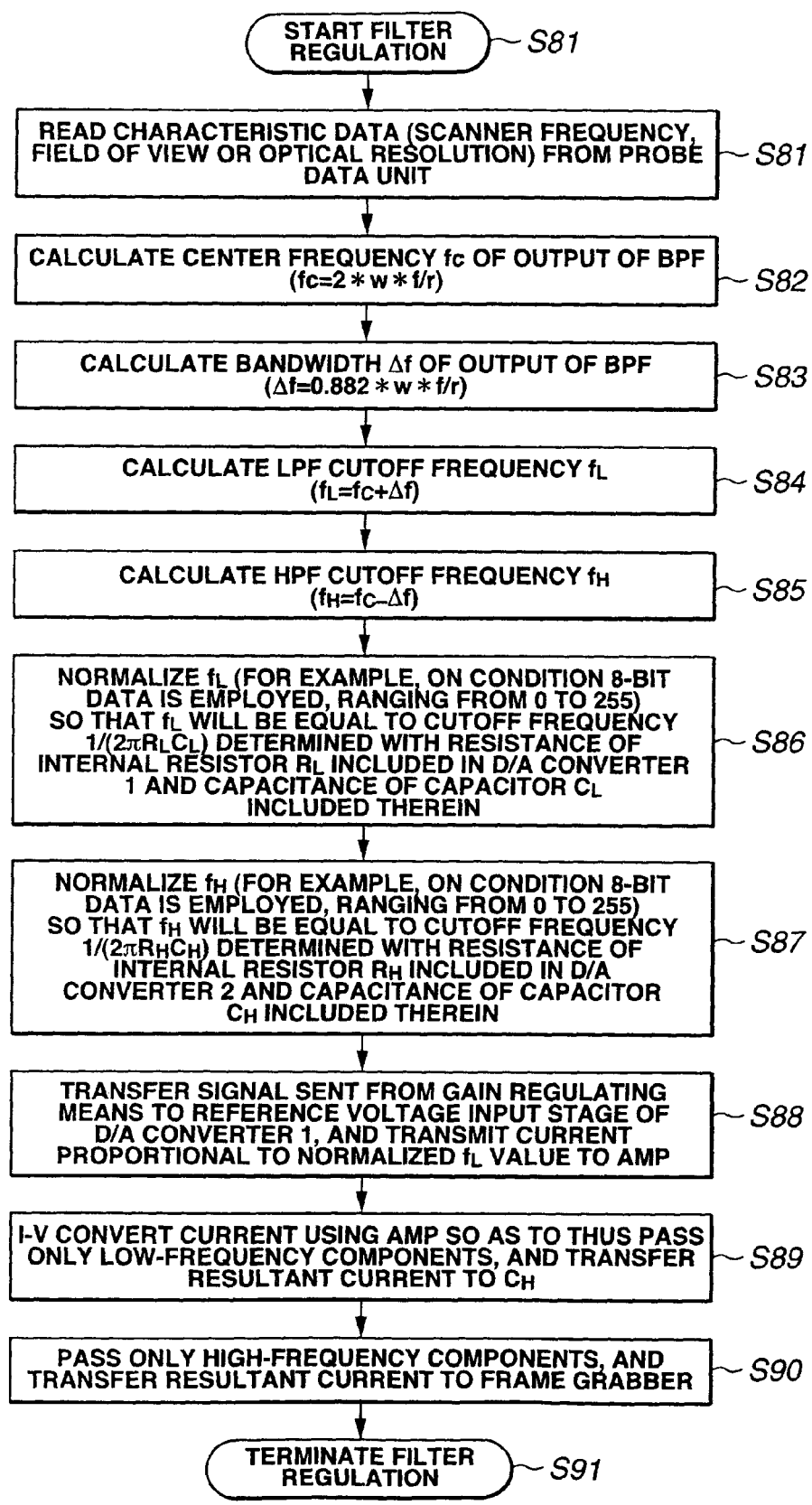

OPTICAL IMAGING SYSTEM AND OPTICAL IMAGING DETECTION METHOD

The present application is a continuation application of International PCT Application No. PCT/JP02/04385 filed May 2, 2002 to which priority is being asserted.

TECHNICAL FIELD

The present invention relates to an optical imaging system and an optical imaging detection method for irradiating a low coherence light beam to an object and constructing a tomographic image of the inside of the object from information of light scattered or reflected from the object.

BACKGROUND ART

Arts related to optical imaging systems include, for example, the one described in Japanese Unexamined Patent Application Publication No. 11-148897. As one type of optical imaging system, an optical imaging system referred to as an optical coherence tomography system is known. The optical coherence tomography system has an optical probe that is inserted into a human body and that has a light receiving/emitting means incorporated in the distal part thereof. The light receiving/emitting means emits low coherence light beam to an object through a light receiving/ emitting port and receives light reflected from the object. Based on the reflected light the optical probe receives from the object, a tomographic image of the object is produced by utilizing the interference of light.

In the optical imaging system, an optical scanner probe is connected to a main body of an observing device through a connector by which the optical scanner probe can be freely detachably attached to the main body. The probe can be readily replaced with another.

Aside from the above optical imaging system, for example, Japanese Patent Application No. 11-134590 has disclosed another type of optical imaging system. This type of optical imaging system includes a rotational driving means, which rotates an optical scanner probe, and an advancement/withdrawal driving means, which advances or withdraws the optical scanner program in axial directions, so as to produce a three-dimensional tomographic image of an object.

In the optical imaging system described in the Japanese Unexamined Patent Application Publication No. 11-148897, when a plurality of types of optical probes that are different from one another in terms of a scanning range within which an optical probe can scan data, a focal length, or the diameter of a sheath are used, a human being by himself/herself must discriminate one type of optical probe from the others. The human being then has to carry out time-consuming work, that is, manually determine the settings of the system (hardware and software alike) based on the type of optical probe and the characteristics thereof.

Moreover, in the related art, no consideration is taken into a change in any parameter (for example, the diameter of a probe or a focal point) other than a difference in the length of an optical scanner probe. Therefore, optical scanner probes that are different from one another in terms of any parameter other than the length thereof (different types of optical scanner probes) are not interchangeable.

Furthermore, in the related art, a human being must discern a difference in the lengths of optical scanner probes. An optical path length is manually adjusted in order to correct the length. Detection, discernment, and adjustment are time-consuming.

On the other hand, the optical imaging system described in the Japanese Patent Application No. 11-134590 is a dedicated three-dimensional optical imaging system. The optical imaging system is therefore of little general-purpose. When an optical scanner probe other than a three-dimensional optical scanner probe is used in combination, it is hard to control the system and display images suitable to the probe therewith. Thus, the optical imaging system has low adaptability.

Moreover, in the above system, it is hard to find a focal point at which a resolution of a displayed tomographic image is the highest. An operator has to find a focal point with his/her eyes. It therefore takes too much time to achieve diagnosis. In particular, when a plurality of types of optical probes are employed, since the focal points of the optical probes are different from one another, it is very hard to find where is the focal point of an optical probe.

Furthermore, the conventional optical imaging systems have not taken measures to obviate the necessity of correcting an individual difference of an optical probe that is freely detachably attached to a main body.

Furthermore, the conventional optical imaging systems include a scanning means that includes a scanner but do not attempt to control an image producing means using information, which is acquired by the scanning means, in consideration of the characteristics of an optical probe.

Moreover, in the conventional optical imaging systems, a gain to be produced is controlled based on the property of return light from an object to be observed which is measured in advance. It is therefore necessary to measure the property of return light relative to each probe whose optical characteristics are different from the others. Gain control is therefore labor-intensive.

Furthermore, in the conventional optical imaging systems, bandwidth is optimally adjusted by observing an object to be observed and by manually adjusting a bandwidth limitation filter. Every time a probe whose optical characteristics are different from a reference probe, or every time an object is observed using the same probe, the bandwidth must be regulated. This is bothering.

Moreover, in the conventional optical imaging systems, a predetermined gamma is calculated in advance relative to an object to be observed. An actual gamma is corrected based on the calculated value. It is therefore necessary to acquire and adjust the gamma every time an optical probe whose optical characteristics are different from a reference probe. Attending to gamma control is labor-intensive. The conventional optical imaging systems include, for example, like the system described in Japanese Unexamined Patent Application Publication No. 2000-75210, an optical imaging system having two scanners driven to scan inputs while tracing a Lissajous figure. However, the optical imaging system described in the Japanese Unexamined Patent Application Publication No. 2000-75210 does not provide measures against the conditions for driving the scanners, the details of an operating procedure, and imaging.

The present invention attempts to address the foregoing situations. An object of the present invention is to provide an optical imaging system and an optical imaging detection method capable of automatically detecting and identifying the characteristics of any of a plurality of types of optical probes.

Another object of the present invention is to provide an optical imaging system that automatically detects the characteristics of an optical probe (including a scanning technique, a focal point, and the diameter of a sheath) so a to control the probe optimally relative to the type thereof or determine an optimal display. Otherwise, the optical imaging system presents on a display image the information of the type of optical probe or of the characteristics thereof or enables designation of the information thereof.

Still another object of the present invention is to provide an optical imaging system capable of scanning-drive controlling, a light path adjusting, or a display image adjusting, suitable to a connected optical probe.

DISCLOSURE OF INVENTION

The present invention provides an optical imaging system that irradiates light from a light source and constructs an observed image of an object using information carried by return light from the object. The optical imaging system mainly comprises:

an optical probe, which is replaceable, propagates the light emanating from the light source to the object, and receives the return light from the object;

a main body which includes a light receiving means that receives the return light from the light source and object and converts the received light into an electric signal, and to which the optical probe can be freely detachably attached;

a detecting means that detects the characteristics of an optical probe attached to the main body; and a designating means that designates the conditions for controlling the optical probe according to the characteristics of the optical probe detected by the detecting means.

Moreover, the present invention provides an optical imaging detection method according to which light emanating from a light source is irradiated to an object, and an observed image of the object is constructed using information carried by return light from the object. The optical imaging detection method is implemented in an optical imaging system that includes:

an optical probe, replaceable, that propagates the light, which emanates from the light source, to the object, receives return light from the object;

a light receiving means that receives the return light from the light source and object and converts the light into an electrical signal;

a device main body to which the optical probe can be freely detachably attached; and detecting means that detects the characteristics of an optical probe attached to the device main body.

According to the optical imaging detection method, the conditions for controlling an optical probe are determined based on the characteristics of the optical probe detected by the detecting means.

BRIEF DESCRIPTION OF THE DRAWINGS

FIG. 8 shows the configuration of an optical path length adjusting mechanism for dealing with reference light that is included in an optical path length scanning unit;

FIG. 9A shows an OCT image produced when an optical path length of measurement light reflected from a living-body tissue agrees with an optical path length of a reference light; FIG. 9B shows an OCT image produced when an optical path length of measurement light reflected from a living-body tissue is larger than an optical path length of a reference light;

28B is a graph indicating a driving frequency at which an X scanner is driven.

FIG. 30A is a data table specifying a type of probe, an optical path length and others; FIG. 30B is a data table specifying the conditions for driving an X scanner; FIG. 30C is a data table specifying the conditions for driving a Y scanner;

FIG. 35A is an explanatory diagram showing sampled image data items rearranged in a real space; FIG. 35B is an explanatory diagram concerning an interpolation extraction performed in an odd frame using the bi-linear interpolation method in the state shown in FIG. 35A; FIG. 35C is an explanatory diagram concerning aliasing of data, performed in an even frame, in the state shown in FIG. 35B;

FIG. 36A is a graph showing the waveform of a Y driving signal that is a driving signal with which a Y scanner is driven; FIG. 36B is a graph showing the waveform of a (Y-U/D) signal with which it is discriminated whether the Y scanner driven with the Y driving signal shown in FIG. 36A is on the outward sweep or homeward sweep; FIG. 36C is a graph showing the waveform of a Y triggering signal (Y-Sync); FIG. 36D is a graph showing the waveform of an X triggering signal (X-Sync); FIG. 36E is a graph showing the waveform of a signal having a clock frequency fs;

FIG. 37A is a graph showing the waveform of a Y driving signal that is a driving signal with which the Y scanner is driven; FIG. 37B is a graph showing the waveform of the (Y-U/D) signal with which it is discriminated whether the Y scanner driven with the Y driving signal shown in FIG. 37A is on the outward sweep or homeward sweep; FIG. 37C is a graph showing the waveform of the Y triggering signal (Y-Sync); FIG. 37D is a graph showing the waveform of the X triggering signal (X-Sync); FIG. 37E is a graph showing the waveform of a signal having a clock frequency fs; FIG. 37F is a graph showing the waveform of an X driving signal that is a driving signal with which the X scanner is driven; FIG. 37G is a graph showing an angle by which an optical element whose input is scanned by the X scanner is driven in an X direction;

FIG. 38A is a graph indicating the waveform of a Y driving signal that is a driving signal with which the Y scanner is driven; FIG. 38B is a graph indicating the waveform of a (Y-U/D) signal with which it is discriminated whether the Y scanner driven with the Y driving signal shown in FIG. 38A is on the outward sweep or homeward sweep; FIG. 38C is a graph indicating the waveform of the Y triggering signal (Y-Sync); FIG. 38D is a graph indicating the waveform of the X triggering signal (X-Sync); FIG. 38E is a graph indicating the waveform of a signal having the clock frequency fs; FIG. 38F is a graph indicating the waveform of the X driving signal that is a driving signal with which the X scanner is driven; FIG. 38G is a graph indicating an angle by which an optical element whose input is scanned by the X scanner is driven in the X direction;

FIG. 39A is a graph indicating the waveform of the Y driving signal that is a driving signal with which the Y scanner is driven; FIG. 39B is a graph indicating the waveform of the (Y-U/D) signal with which it is discriminated whether the Y scanner driven with the Y driving signal shown in FIG. 39A is on the outward sweep or homeward sweep; FIG. 39C is a graph indicating the waveform of the Y triggering signal (Y-Sync); FIG. 39D is a graph indicating the waveform of the X triggering signal (X-Sync); FIG. 39E is a graph indicating the waveform of a signal having the clock frequency fs; FIG. 39F is a graph indicating the waveform of the X driving signal that is a driving signal with which the X scanner is driven; FIG. 39G is a graph indicating an angle by which an optical element whose input is scanned by the X scanner is driven in the X direction;

FIG. 40A is a graph indicating the waveform of the Y driving signal that is a driving signal with which the Y scanner is driven; FIG. 40B is a graph indicating the waveform of the (Y-U/D) signal with which it is discriminated whether the Y scanner driven with the Y driving signal shown in FIG. 40A is on the outward sweep or homeward sweep; FIG. 40C is a graph indicating the waveform of the Y triggering signal (Y-Sync); FIG. 40D is a graph indicating the waveform of the X triggering signal (X-Sync); FIG. 40E is a graph indicating the waveform of a signal having the clock frequency fs; FIG. 40F is a graph indicating the waveform of the X driving signal that is a driving signal with which the X scanner is driven; FIG. 40G is a graph indicating an angle by which an optical element whose input is scanned by the X scanner is driven in the X direction;

FIG. 41A is a graph indicating the waveform of the Y driving signal that is a driving signal with which the Y scanner is driven; FIG. 41B is a graph indicating the waveform of the (Y-U/D) signal with which it is discriminated whether the Y scanner driven with the Y driving signal shown in FIG. 41A is on the outward sweep or homeward sweep; FIG. 41C is a graph indicating the waveform of the Y triggering signal (Y-Sync); FIG. 41D is a graph indicating the waveform of the X triggering signal (X-Sync); FIG. 41E is a graph indicating the waveform of a signal having the clock frequency fs; FIG. 41F is a graph indicating the waveform of the X driving signal that is a driving signal with which the X scanner is driven; FIG. 41G is a graph indicating an angle by which an optical element whose input is scanned by the X scanner is driven in the X direction;

FIG. 42A is a graph indicating the waveform of the Y driving signal that is a driving signal with which the Y scanner is driven; FIG. 42B is a graph indicating the waveform of the (Y-U/D) signal with which it is discriminated whether the Y scanner driven with the Y driving signal shown in FIG. 42A is on the outward sweep or homeward sweep; FIG. 42C is a graph indicating the waveform of the Y triggering signal (Y-Sync); FIG. 42D is a graph indicating the waveform of the X triggering signal (X-Sync); FIG. 42E is a graph indicating the waveform of a signal having the clock frequency fs; FIG. 42F is a graph indicating the waveform of the X driving signal that is a driving signal with which the X scanner is driven; FIG. 42G is a graph indicating an angle by which an optical element whose input is scanned by the X scanner is driven in the X direction;

FIG. 64 is a flowchart describing filter adjustment; and

BEST MODE FOR CARRYING OUT THE INVENTION

Figure 1:
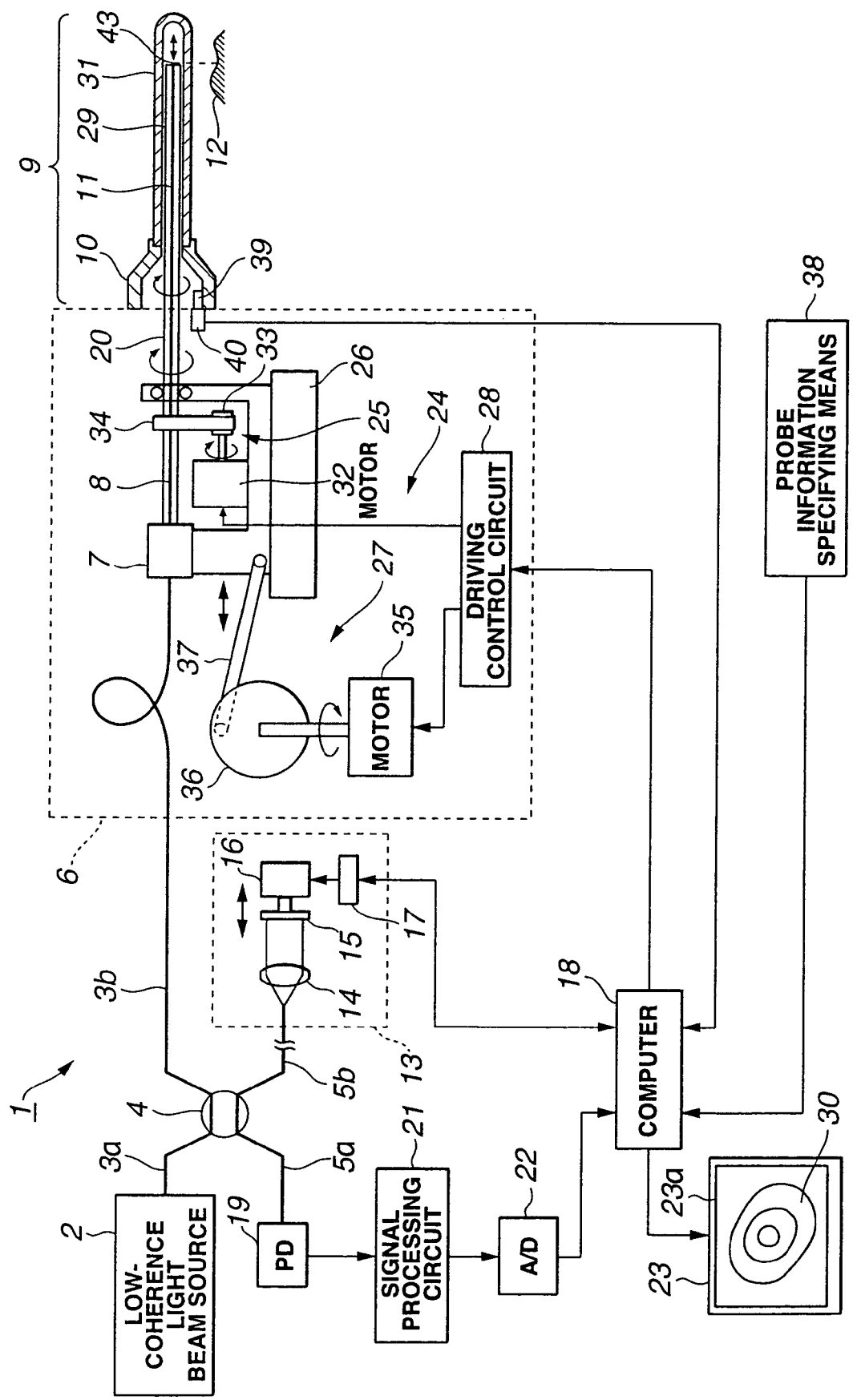
FIG. 1 shows the configuration of an optical imaging system in accordance with a first embodiment of the present invention.

Referring to the drawings, embodiments of the present invention will be described below.

FIRST EMBODIMENT

Figure 2:
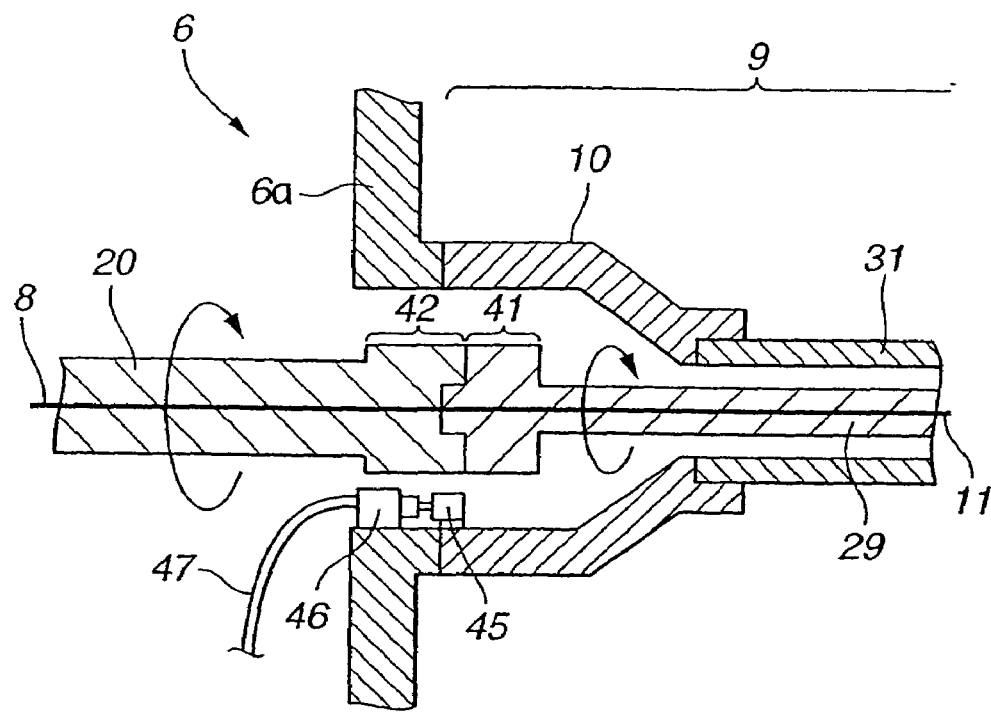
FIG. 2 shows the structure of a micro-switch-inclusive probe information detecting mechanism included in the optical imaging system shown in FIG. 1.
Figure 3:
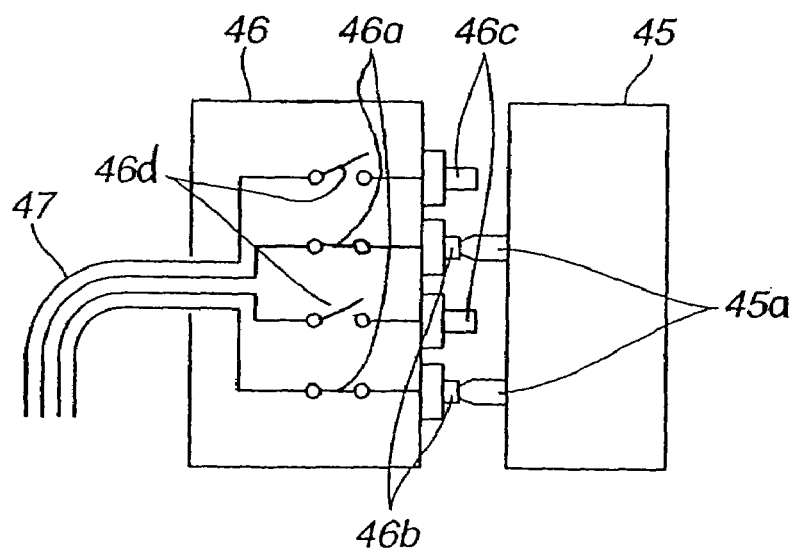
FIG. 3 is an explanatory diagram concerning the principles of operation based on a micro-switch detecting method implemented in the mechanism shown in FIG. 2.
Figure 4:
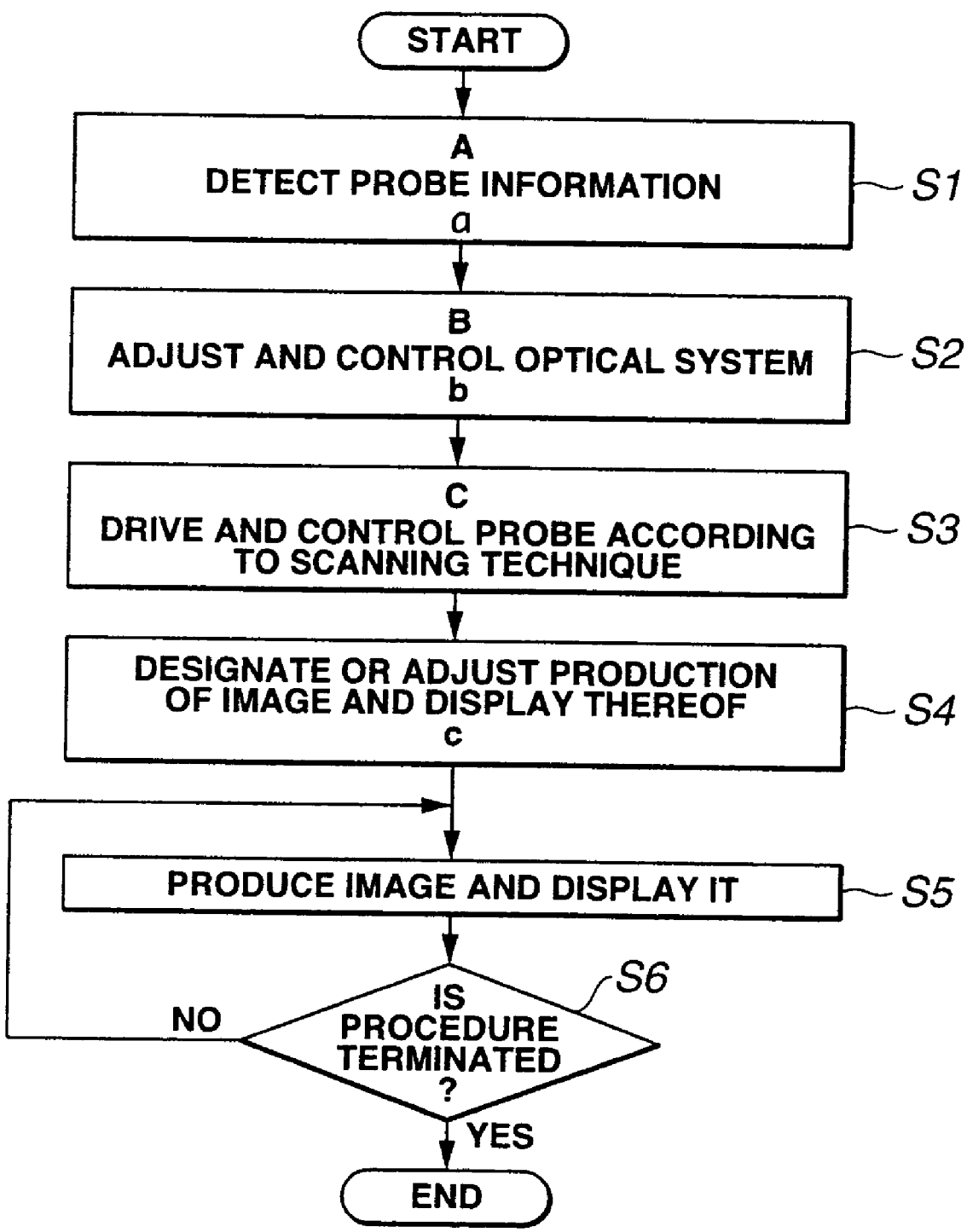
FIG. 4 is a flowchart describing a procedure of detecting and processing probe information.
Figure 5:
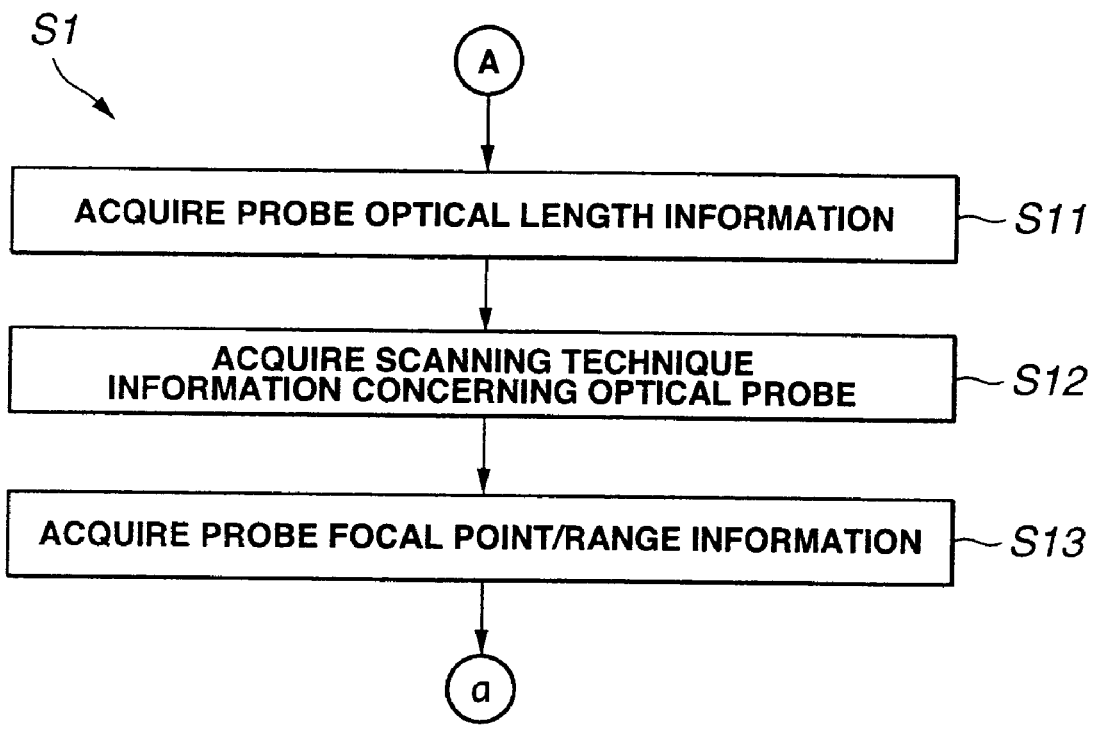
FIG. 5 is a flowchart describing the details of the probe information detecting procedure described in FIG. 4.
Figure 6:
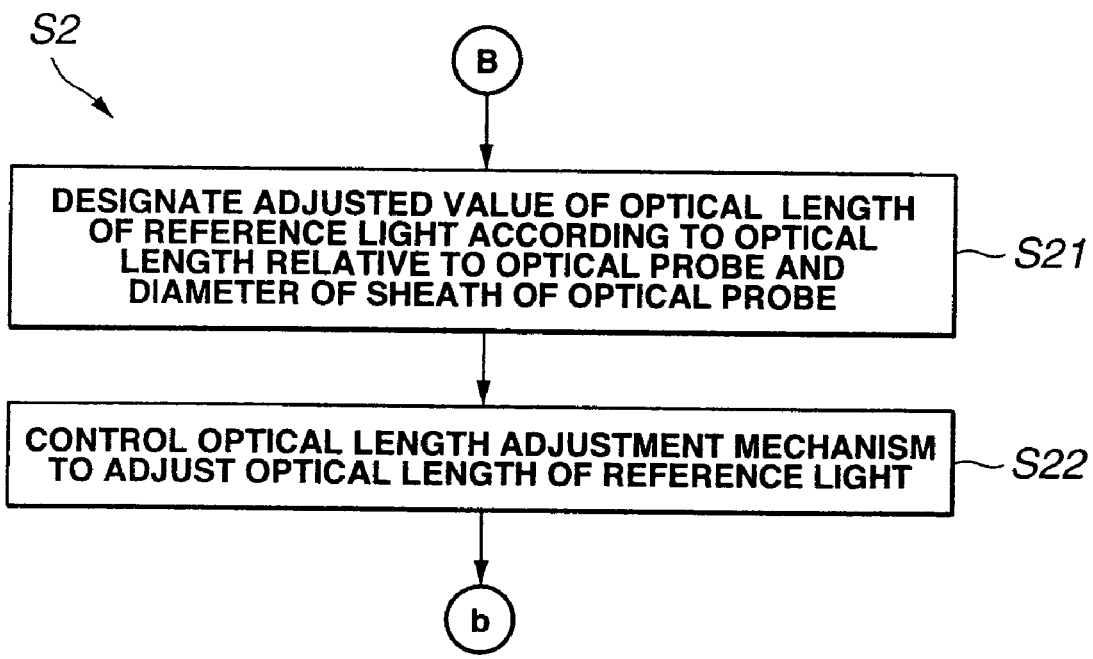
FIG. 6 is a flowchart describing a procedure of adjusting and controlling an optical system mentioned in FIG. 4.
Figure 7:
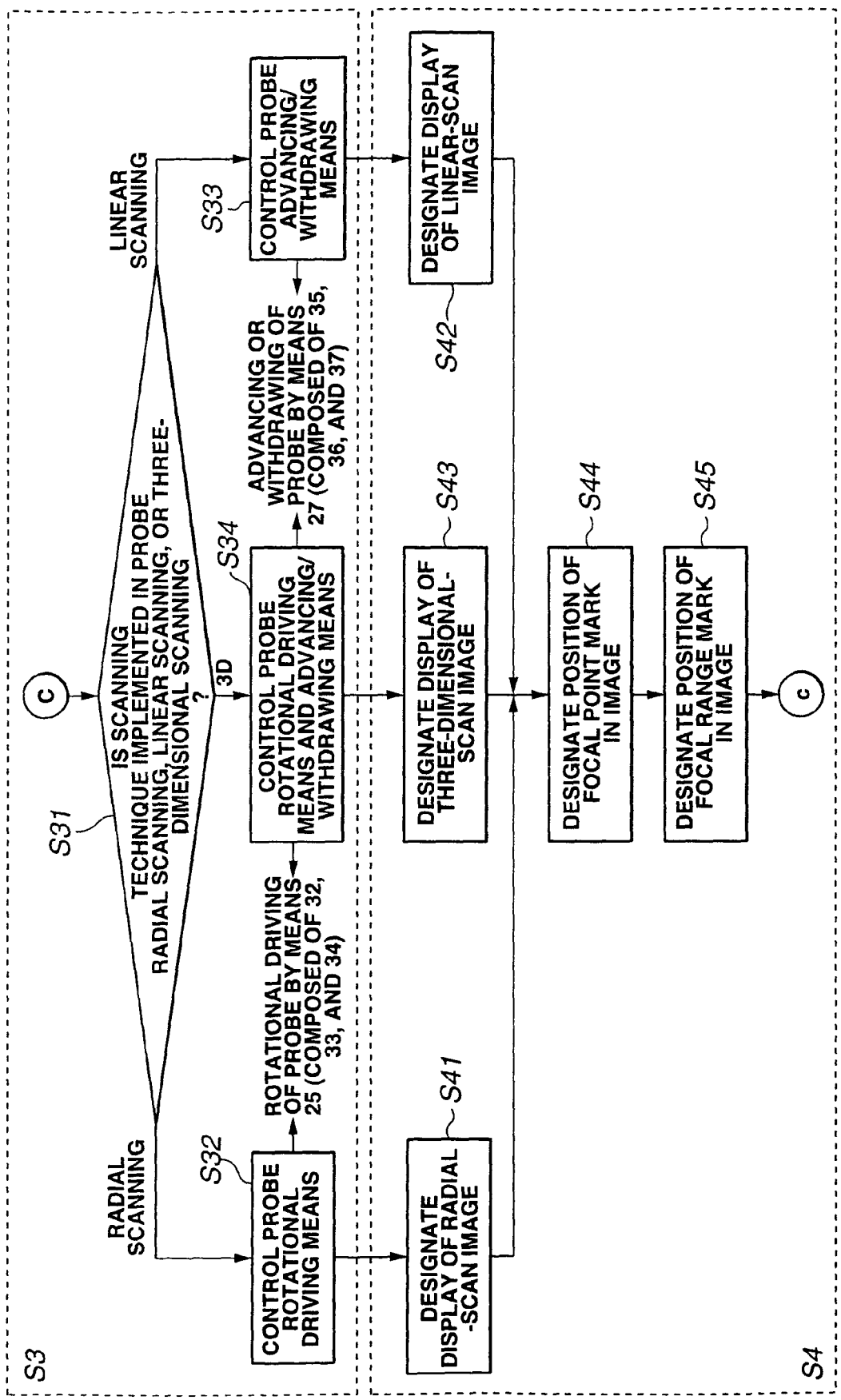
FIG. 7 is a flowchart describing a procedure of driving and controlling a probe according to a scanning technique implemented in the probe, and a procedure of setting the imaging and the display thereof.
Figure 10:
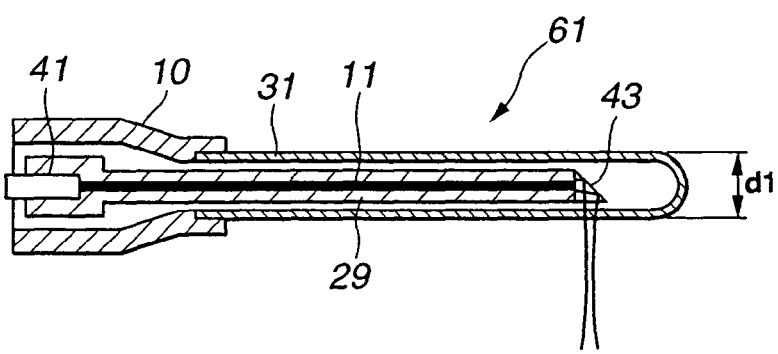
FIG. 10 shows the structure of an optical probe whose sheath has a small diameter.
Figure 11:
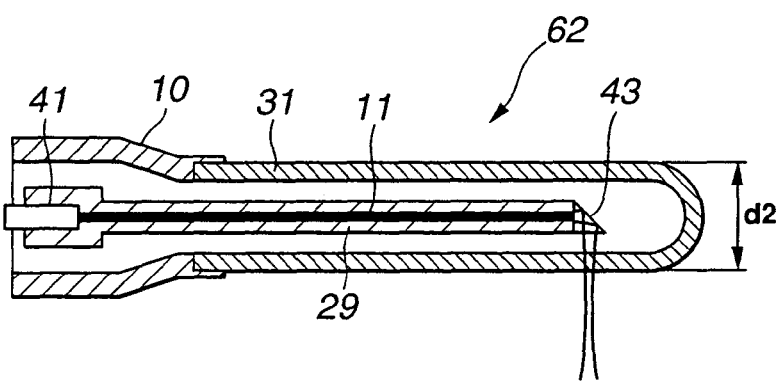
FIG. 11 shows the structure of an optical probe whose sheath has a large diameter.
Figure 12:
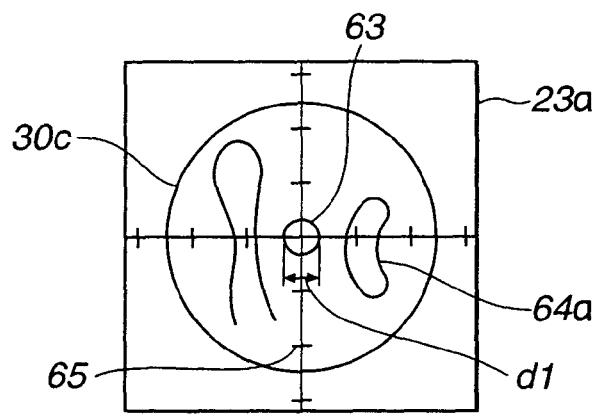
FIG. 12 is an explanatory diagram showing on a radial-scan tomographic image the sheath of the probe shown in FIG. 10.
Figure 13:
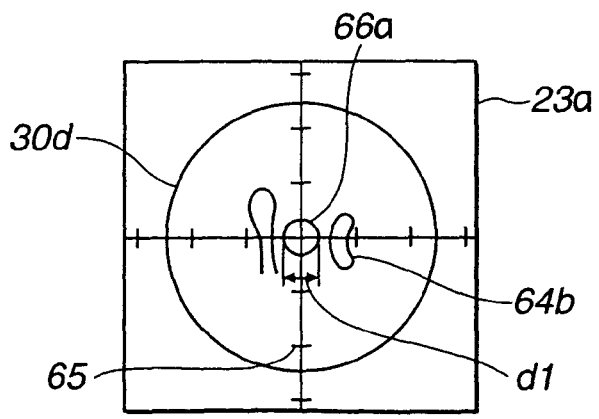
FIG. 13 is an explanatory diagram showing the sheath of the optical prove shown in FIG. 11 on a radial-scan tomographic image without an optical path length adjusted.
Figure 14:
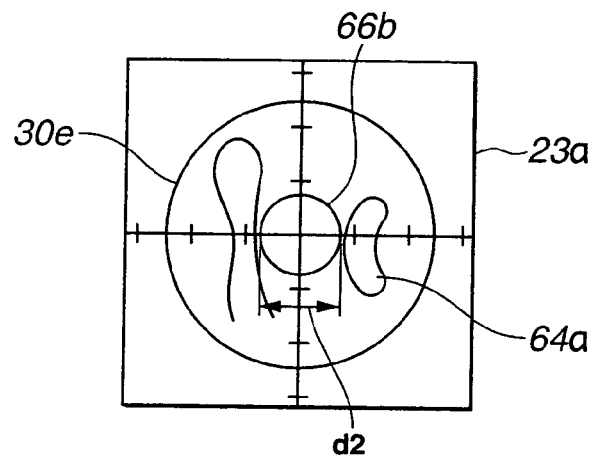
FIG. 14 is an explanatory diagram showing the sheath of the optical probe shown in FIG. 11 on a radial-scan tomographic image with an optical path length adjusted.
Figure 15:
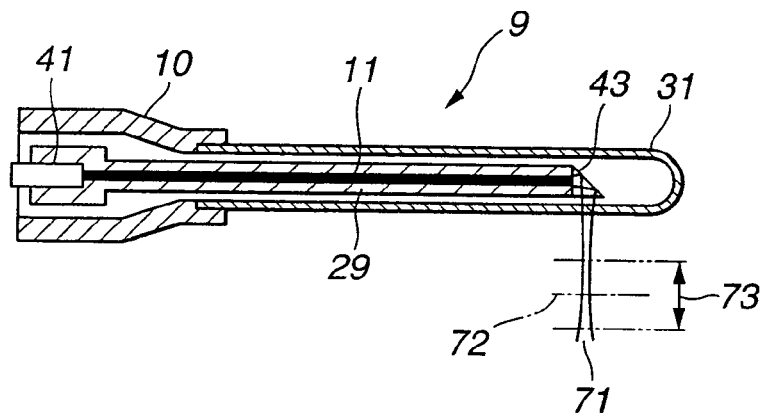
FIG. 15 is an explanatory diagram showing a focal point of measurement light beam emitted from an optical probe and a focal range thereof.
Figure 16:
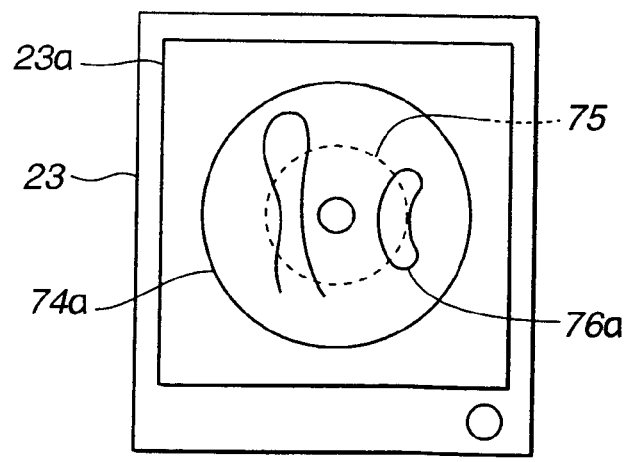
FIG. 16 is an explanatory diagram showing a focal point offered by an optical probe and delineated in an OCT image produced by performing radial scanning.
Figure 17:
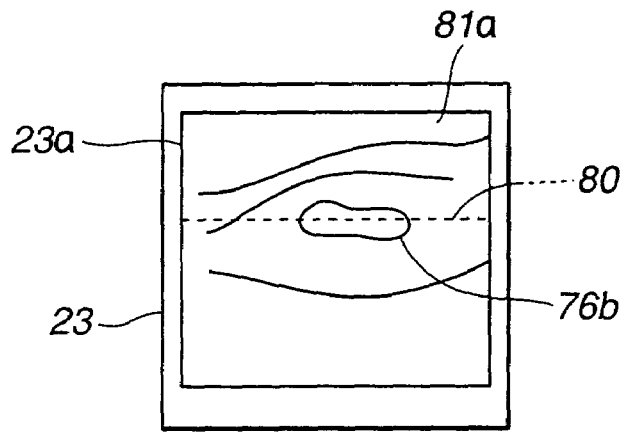
FIG. 17 is an explanatory diagram showing a focal point offered by an optical probe and delineated in an OCT image produced by performing linear scanning.
Figure 18:
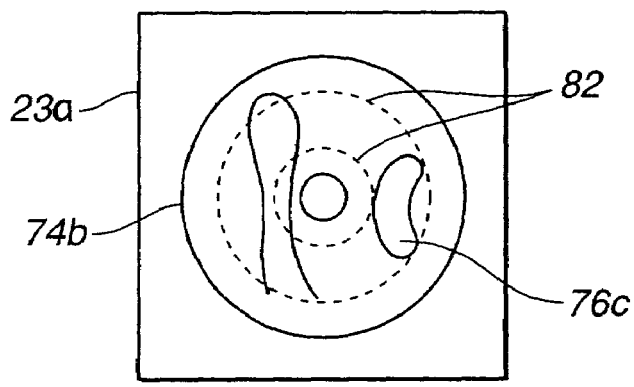
FIG. 18 is an explanatory diagram showing a focal range offered by an optical probe and delineated in an OCT image produced by performing radial scanning.
Figure 19:
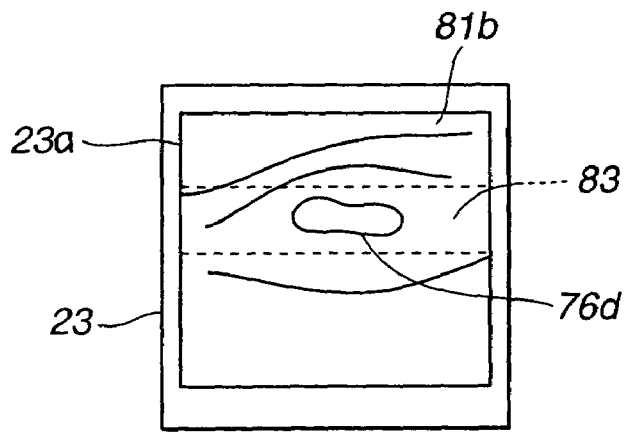
FIG. 19 is an explanatory diagram showing a focal range offered by an optical probe and delineated in an OCT image produced by performing linear scanning.

FIG. 1 to FIG. 19 are concerned with a first embodiment of the present invention. FIG. 1 shows the configuration of an optical imaging system in accordance with the first embodiment. FIG. 2 shows the structure of a micro-switch-inclusive probe information detecting mechanism included in the optical imaging system shown in FIG. 1. FIG. 3 is an explanatory diagram concerning the principles of operation based on a micro-switch-inclusive detecting method implemented in the mechanism shown in FIG. 2. FIG. 4 is a flowchart describing a procedure for detecting and processing probe information. FIG. 5 is a flowchart detailing the probe information detecting procedure mentioned in FIG. 4. FIG. 6 is a flowchart describing a procedure of adjusting and controlling an optical system included in the procedure mentioned in FIG. 4. FIG. 7 is a flowchart describing a procedure of driving and controlling a probe according to a scanning technique implemented in the probe, a procedure of imaging, and a procedure of determining the settings for display, which correspond to steps described in FIG. 4. FIG. 8 shows the structure of an optical path length automatic adjustment mechanism that adjusts the optical path length of reference light and that is included in an optical path length scanning unit. FIG. 9A and FIG. 9B show radial-scan tomographic images produced by performing radial scanning before and after the optical path length automatic adjustment mechanism shown in FIG. 8 is actuated. FIG. 10 shows the structure of an optical probe whose sheath has a small diameter. FIG. 11 shows the structure of an optical probe whose sheath has a large diameter. FIG. 12 is an explanatory diagram showing an image displayed on the optical imaging system shown in FIG. 10. FIG. 13 is an explanatory diagram showing the sheath of the optical probe shown in FIG. 11 on a radial-scan tomographic image with an optical path length unadjusted. FIG. 14 is an explanatory diagram showing the sheath of the optical probe shown in FIG. 11 on a radial-scan tomographic image with an optical path length adjusted. FIG. 15 is an explanatory diagram showing a focal point of measurement light beam, which is propagated from an optical probe, and a focal range thereof. FIG. 16 is an explanatory diagram showing a focal point offered by an optical probe and delineated in a radial-scan OCT image. FIG. 17 is an explanatory diagram showing a focal point offered by an optical probe and delineated in a linear-scan OCT image. FIG. 18 is an explanatory diagram showing a focal range offered by an optical probe and delineated in a radial-scan OCT image. FIG. 19 is an explanatory diagram showing a focal range offered by an optical probe and delineated in a linear-scan OCT image.

An optical imaging system (optical tomographic imaging system) 1 shown in FIG. 1 includes a low coherence light beam source 2. The low coherence light beam source 2 generates low coherence light beam whose wavelength is, for example, 1300 nm and whose coherence length is, for example, about 17 μm, that is, low coherence light beam that exhibits coherence within a short distance. For example, assume that the light beam is bisected and then merged again. If a difference between two optical path lengths to a point of bisection is a short distance of about 17 μm, the light is detected as coherent light beam. If the difference exceeds about 17 μm, the light exhibits incoherence.

Light emanating from the low coherence light beam source 2 is incident on one end of a first single-mode fiber 3a and propagated to the other end thereof. The first single-mode fiber 3a is optically coupled with a second single-mode fiber 5a within an optical coupler 4. The optical coupler 4 bisects light into measurement light beam and reference light. The measurement light beam is transmitted to a third single-mode fiber 3b, while the reference light is transmitted to a fourth single-mode fiber 5b.

The distal end of the third single-mode fiber 3b (coupled to the optical coupler 4) is joined with a fifth single-mode fiber 8 via an optical rotary joint 7, which has non-rotating and rotating sections and passes light, within an optical imaging observation device 6. A connector (or attachment) 10 of an optical scanner probe (hereinafter abbreviated to an optical probe) 9 is freely detachably attached to the distal end of the fifth single-mode fiber 8. The light emanating from the low coherence light beam source 2 is transmitted to a sixth single-mode fiber 11 that runs through the optical scanner probe 9. The transmitted measurement light beam is reflected from a prism 43 incorporated in the distal part of the optical probe 9, and irradiated to a living-body tissue 12 that is an object while being scanned.

Moreover, the reference light separated by the optical coupler 4 and propagated along the fourth single-mode fiber 5b is transmitted to an optical path length scanning unit 13 that changes the optical path length of the reference light.

The reference light is irradiated to a mirror 15 via a lens 14 from the distal end surface of the optical fiber 5b within the optical path length scanning unit 13, and then reflected from it. The mirror 15 can be advanced or withdrawn in optical-axis directions by means of an actuator 16. By changing the position of the mirror 15, the optical path length (optical delay) can be varied.

The action of the actuator 16 is controlled by an actuator control circuit 17 connected to a computer 18. The optical path length scanning unit 13 can change with high speed the optical path length of the reference light within the scanning range by the optical probe 9, in relative to a predetermined scanning range extending in the direction of depth of the living-body tissue 12.

Moreover, part of the measurement light beam scattered or reflected from the surface of the living-body tissue 12 or internally thereof is fetched into the optical probe 9 and returned to the third single-mode fiber 3b by reversely tracing the light path. Moreover, the reference return light from the optical path length scanning unit 13 returns to the fourth single-mode fiber 5b. The return light of the measurement light beam and the reference light interfere with each other within the optical coupler 4, and the resultant light is incident on a photo-detector (PD) 19 through the distal end of the second single-mode fiber 5a.

A coherence electric signal resulting from photoelectric conversion performed by the photo-detector 19 is inputted to a signal processing circuit 21. The signal processing circuit 21 processes the coherence electric signal. The output of the signal processing circuit 21 is transmitted to the computer 18 via an A/D converter 22. The computer 18 produces image data representing a tomographic image, and transmits the image data to a monitor 23. Consequently, an OCT (image produced by optical imaging) image 30 is displayed on a display surface 23a of the monitor.

Incidentally, the optical rotary joint 7 is driven by a drive unit 24 included in the observing device 6.

The drive unit 24 includes rotational driving means 25 that rotationally drives the rotor included in the optical rotary joint 7, and an advancing/withdrawing means 27 that advances or withdraws the optical rotary joint 7 and rotational driving means 25, which are mounted on a lock mount 26, in axial directions. The rotational driving means 25 and advancing/withdrawing means 27 are controlled by a driving control circuit 28.

A light guide member (a hollow flexible shaft 29 having the optical fiber 11 run through it) included in the probe 9 and joined with the rotor included in the optical rotary joint 7 radially rotates or linearly advances or withdraws within a sheath 31 of the optical probe 9.

The rotational driving means 25 consists of a motor 32 that rotates for driving, a motor rotor (pulley) 33 fixed to the rotation shaft of the motor 32, and a belt 34 laid over between the motor rotor (pulley) 33 and a shaft 20 through which the fifth single-mode fiber 8 runs.

The advancing/withdrawing means 27 consists of a motor 35 that rotates for driving, a rotary plate 36 that is rotated by the motor 35, and a driving rod 37 having one end thereof coupled to the rotary plate 36, having the other end thereof coupled to the lock mount 26, and being used to advance or withdraw the assemblage coupled to the other end thereof.

Moreover, the computer 18 controls the rotational driving means 25 and advancing/withdrawing means 27, which are included in the driving unit 24, via the driving control circuit 28.

Probe information specifying means 38 that specifies feature information concerning the optical probe 9 is connected to the computer 18. The probe information specifying means 38 is used to enter the feature information of the optical probe 9, whereby the computer 18 can control or perform adjustment or adjustment suitable to the optical probe 9. The probe information specifying means 38 is a kind of manual input means, for example, a keyboard or switches.

Alternatively, the probe information specifying means 38 may be replaced with means for automatically detecting the feature information of the optical probe 9 as described later.

For brevity's sake, FIG. 1 and others show the means for automatically detecting the feature information of the optical probe 9 together with the probe information specifying means 38.

As shown in FIG. 1, the optical probe 9 is connected to the optical imaging observation device 6 via the attachment 10 of the optical probe 9. A probe information holding means 39 is incorporated in the attachment 10 of the optical probe 9.

A probe information detecting means 40 is provided opposite the probe information holding means 39 and located in the portion of the observing device 6 coupled to the attachment 10 of the optical probe 9. Owing to this structure, when the optical probe 9 is connected to the observing device 6, probe information held in the probe information holding means 38 is detected by the probe information detecting means 40 and inputted thereto. The probe information is then transmitted to the computer 18. The computer 18 checks the detected probe information, and controls the system or determines the settings of the system according to the optical probe 9.

Next, a description will be made of a micro-switch-inclusive mechanism as a concrete example of an assemblage of the probe information holding means 39 and probe information detecting means 40.

FIG. 2 and FIG. 3 are concerned with an optical probe information holding and detecting means employed in the present embodiment. A micro-switch-inclusive type mechanism for detecting optical probe information will be described below. FIG. 2 shows the optical probe 9 connected to the optical imaging observation device 6.

The sheath 31 of the optical probe 9 and the attach 10 thereof are coupled to a joint member 6a of the optical imaging observation device 6. The light guide member (optical fiber 11 and flexible shaft 29) of the optical probe 9 is coupled to the shaft 20, through which the optical fiber 8 extended in the optical imaging observation device 6 runs, via an optical connector 41 formed as the rear part of the light guide member and an optical connector bearing 42 meshed with the optical connector 41. A plurality of sensor pins 45 are projected in parallel with the center axis of the optical probe 9 within the attachment 10 of the optical probe 9, whereby the probe information holding means 39 shown in FIG. 1 is constituted.

Moreover, micro-switches 46 are disposed on the internal surface of the joint member 6a of the optical imaging observation device 6 and opposed to the sensor pins 45 so that the micro-switches 46 can freely come into contact with or non-contact with the sensor pins 45, whereby the probe information detecting means 40 shown in FIG. 1 is constituted. All the micro-switch elements included in the micro-switches 46 have one terminals thereof connected to a detection circuit included in the computer 18 over cables 47.

FIG. 3 shows the relationship among connections. Push pins 46b (of each micro-switch 46) located to face projections 45a of each sensor pin 45 are pressed by the projections 45a. Consequently, switches 46ad connected to the push pins 46b are turned on.

Push pins 46c of each micro-switch 46 located at positions at which no projection of each sensor pin 45 is jutting are not pressed. Switches 46a connected to the push pins 46c therefore remain off. The switches 46a and switches 46d are connected to the computer 18 over the cables 47. The (on or off) states of the switches are recognized as probe feature information by the computer 18.

When both the joint members are joined as mentioned above, the switch elements of each micro-switch 46 are turned on or off depending on the arrangement of the projections 45a of each sensor pin 45. The computer 18 detects the on or off states of the switch elements included in each of the micro-switches 46. The computer 18 recognizes the on or off states as probe feature information concerning the connected optical probe 9.

The arrangement pattern of the projections 45a included in the sensor pins 45 is associated with each type of optical probe 9. The number of types of optical probes that can be identified is a square of the number of switch elements included in each micro-switch 46. For example, when the number of switch elements is 4 as shown in FIG. 3, the number of types of optical probes that can be identified is 16.

Based on the feature information of the optical probe 9 detected by the feature information detecting means included in the optical probe 9, the optical imaging system is controlled and adjusted suitably to the optical probe 9.

FIG. 4 is a flowchart describing a procedure of detecting and processing probe information. Referring to FIG. 4, at step S1, feature information concerning the connected optical probe 9 is acquired from the probe information holding means 39 and probe information detecting means 40 (acquisition procedure will be described in conjunction with FIG. 5). At step S2, based on the optical characteristics information concerning the optical probe 9 acquired at step S1, the computer 18 adjusts or controls an optical system included in the optical imaging system 1 (adjustment procedure will be described in conjunction with FIG. 6).

At step S3 in FIG. 4, based on a scanning technique implemented in the optical probe 9 and acquired at step S1, the optical probe 9 is driven and controlled for scanning (the control sequence will be described in conjunction with FIG. 7).

At step S4 in FIG. 4, based on the information of the optical probe 9 acquired at step S1, the production of an OCT image and the display thereof are designated (adjusted) (the designation procedure will be described in conjunction with FIG. 7). At step S5 in FIG. 4, an OCT image is produced and displayed. At step S6 in FIG. 4, it is judged whether the procedure is completed. If completion of the procedure is designated, the procedure is terminated. If completion of the procedure is not designated, control is returned to step S5.

FIG. 5 is a flowchart describing the contents of a concrete example of step S1 mentioned in FIG. 4. Referring to FIG. 5, at step S11, the optical path length relative to the optical probe 9 and the diameter of the sheath of the optical probe 9 are acquired from the probe information holding means 39 and probe information detecting means 40. At step S12 in FIG. 5, the scanning technique implemented in the optical probe 9 (radial scanning, linear scanning, or three-dimensional scanning) is acquired. At step S13 in FIG. 5, a focal path length or focal range offered by the probe is acquired.

For example, when the computer 18 judges from probe information detected by the probe information detecting means 40 that the optical probe 9 connected to the observing device 6 is, for example, a linear scanning probe, the computer 18 controls the advancing/withdrawing means 27 (composed of the motor 35, rotary plate 36, and driving rod 37) using the driving control circuit 28. Thus, the optical probe 9 is advanced or withdrawn (linearly moved).

Moreover, if it is judged that the connected optical probe 9 is a radial scanning probe, the computer 18 controls the rotational driving means 25 (composed of the motor 32, motor rotor 33, and belt 34) using the driving control circuit 28. Thus, the optical probe 9 is rotated.

Moreover, if a three-dimensional probe (capable of performing both linear scanning and radial scanning) is connected to the observation device 6, the computer 18 identifies the optical probe 9 as the three-dimensional probe. The computer 18 controls the advancing/withdrawing means 27 and rotational driving means 25 using the driving control circuit 28, whereby the optical probe 9 is advanced or withdrawn while being rotated.

FIG. 6 is a flowchart detailing step S2 mentioned in FIG. 4. Namely, FIG. 6 describes a concrete example of step S2 in FIG. 4 at which an optical system is adjusted or controlled. As described later in conjunction with FIG. 8, the optical path length scanning unit 13 includes an optical path length adjusting mechanism 13b that adjusts the optical path length of reference light. FIG. 6 is a flowchart describing a procedure according to which the optical path length adjusting mechanism 13b adjusts or controls the optical path length of reference light.

Referring to FIG. 6, at step S21, an adjusted value of the optical path length of reference light is designated based on the optical path length relative to the optical probe 9 and the diameter of the sheath of the optical probe 9.

In other words, the computer 18 extracts the optical path length relative to the connected optical probe 9 and the diameter of the sheath of the optical probe 9 from the probe information detected by the probe information detecting means 40. The computer 18 adds up the optical path length relative to the optical probe 9 and the diameter of the sheath of the optical probe 9, and transmits the sum as a set value for the optical path length of reference light (an adjusted value of the optical path length) to the optical path length adjusting mechanism 13b.

At step S22 in FIG. 6, the optical path length adjusting mechanism 13b for dealing with the reference light is controlled in order to adjust the optical path length of the reference light.

Specifically, the (motor rotation control circuit 52 shown in FIG. 8 and included in) optical path length adjusting mechanism 13b is controlled in order to control the position of the lens 14 so that the adjusted value of the optical path length of reference light will be equal to a designated optical path length value. Control is then passed to step S3.

The upper half of FIG. 7 (detailing step 3) is a flowchart describing a procedure of driving and controlling a probe according to a scanning technique which corresponds to step S3 in FIG. 4.

At step S31 in FIG. 7, a scanning technique implemented in the optical probe 9 is checked. If the checking reveals that the optical probe 9 is of, for example, a radial scanning type, control is passed to step S32 in FIG. 7.

At step S32, the probe rotational driving means 25 (composed of 32, 33, and 34) shown in FIG. 1 is controlled in order to rotate the optical probe 9.

If the optical probe 9 is of a linear scanning type, control is passed to step S33 in FIG. 7. The prove advancing/withdrawing means 27 (composed of 35, 36, and 37) shown in FIG. 1 is controlled in order to advance or withdraw the optical probe 9.

If the optical probe 9 is of a three-dimensional scanning type, control is passed to step S34 in FIG. 7. Both the probe rotational driving control means 25 (composed of 32, 33, and 34) and the probe advancing/withdrawing means 27 (composed of 35, 36, and 37) are controlled simultaneously in order to advance or withdraw the optical probe 9 while rotating the optical probe 9.

The lower half of FIG. 7 (detailing step S4) is a flowchart describing a procedure of producing an OCT image and designating the display parameters for the OCT image which corresponds to step S4 in FIG. 4.

At step S41 in FIG. 7, the imaging of an OCT and the display thereof are set to a radial-scan OCT image and the display thereof.

At step S42 in FIG. 7, the imaging of an OCT and the display thereof are set to a linear-scan OCT image and the display thereof.

At step S43 in FIG. 7, the imaging of an OCT and the display thereof are set to a three-dimensional-scan OCT image and the display thereof.

At step S44 in FIG. 7, a display position for a focal point mark at which a focal point mark is displayed is specified in an OCT image according to focal position information concerning the optical probe 9 acquired at step S13 in FIG. 5.

At step S45 in FIG. 7, a display position for a focal range mark at which a focal range mark is displayed is specified in an OCT image according to focal range information concerning the optical probe 9 acquired at step S13 in FIG. 5.

Referring to FIG. 8 and FIGS. 9A–9B, a description will be made of a control mechanism for automatically adjusting the optical path length of reference light according to optical path length information concerning the optical probe 9 so that the optical path length of reference light will agree with the optical path length of measurement light beam.

FIG. 8 shows the components of the optical path length scanning mechanism 13a included in the optical path length scanning unit 13, which is included in the optical imaging system 1 and deals with reference light, and the components of the optical path length adjusting mechanism 13b included therein. The optical path length scanning mechanism 13a irradiates reference light (over a predetermined range in the direction of depth), and the optical path length adjusting mechanism 13b adjusts the optical path length of the reference light. FIG. 9A shows an OCT image produced when the optical path length of measurement light beam reflected from the living-body tissue 12 agrees with the optical path length of the reference light. FIG. 9B shows an OCT image produced when the optical path length of the measurement light beam reflected from the living-body tissue 12 is larger than the optical path length of the reference light.

In the optical imaging system 1, even optical probes 9 of the same type may be different from one another in terms of the length of the optical fiber 11, over which measurement light beam is propagated within the optical probe 9, because of an individual difference caused in the course of manufacture or a difference in the specifications for the optical probe 9.

In the optical imaging system 1, an OCT image is produced by converting a light signal, which is produced by coherence light between the measurement light beam propagated from the optical probe 9 and the reference light propagated from the optical path length scanning unit 13, into an electric signal. If the optical path lengths of the measurement light beam and reference light are different from each other, the display position and size of a representation in the OCT image changes. When the difference between the optical path lengths of the measurement light beam and reference light is larger than a scanning width A within which the optical path length scanning mechanism 13a included in the optical path length scanning unit 13 can irradiate reference light, the light signal representing coherence is nullified and no image is superposed in an OCT image.

FIG. 9A shows an OCT image 30a produced by normally performing radial scanning with the optical path length of measurement light beam agreed with the optical path length of reference light. A circle in the center of the OCT image 30a represents a sheath image 55a of the optical probe 9, a figure at the left-hand represents an image 56a of an object a, and a figure at the right-hand represents an image 57a of an object b.

FIG. 9B shows an OCT image 30b produced by performing radial scanning with the optical path length of measurement light beam propagated from the living-body tissue 12 made larger than the one of reference light. In this case, the OCT image 30b is enlarged compared with the one shown in FIG. 9A. The image 55b of the sheath of the optical probe 9 in the center of the image is larger than that shown in FIG. 9A. The image 56a of the object a at the left-hand and the image 57b of the object b at the right-hand are larger than those shown in FIG. 9A, and are partly excluded from the image field of the OCT image 30b.

As mentioned above, when the optical probes 9 whose optical fibers 10 have different lengths are employed, even if the sheaths of the optical probes 9 have the same diameter, the sheath images superposed on OCT images have different sizes, and the images of the same object have different positions and sizes. This brings about a drawback that comparison function deteriorates. It is therefore necessary to adjust the optical path length of reference light so that the optical path length thereof will agree with the optical path length of measurement light beam propagated from the optical probe 9. Incidentally, the display situation shown in FIG. 9B must be adjusted in order to attain the display shown in FIG. 9A.

According to the related arts (for example, the Japanese Unexamined Patent Application Publication No. 11-148897), an optical path length adjusting mechanism is included in order to correct a difference of the length of an optical probe from a reference value. It is a human being who discerns the difference of the length of an optical probe. Besides, an optical path length is adjusted manually in order to correct the length. This leads to the drawback that it is time-consuming to discern the difference of the length of an optical probe and adjusting an optical path length.

According to the present embodiment, as shown in FIG. 8, the optical path length scanning unit 13 for dealing with reference light includes the optical path length adjusting mechanism 13b that adjusts the optical path length of reference light (automatically based on probe information). In the optical path length adjusting mechanism 13b, the distal end of the fiber 5b and the lens 14, which converges reference light, are held in a movable lens holder 49. A screw hole member included in the lens holder 49 is fixed to a rectilinear driving screw mechanism 51 mounted on the rotation shaft of a motor 50.

Moreover, the motor 50 has the number of rotations thereof controlled by a motor rotation control circuit 52. Moreover, the motor 50 has the number of rotations thereof detected by a rotary encoder 53. An encoding signal representing the number of rotations is transmitted to the motor rotation control circuit 52.

When the motor 50 is rotated, the lens 14 held in the lens holder 49 advances in a direction of propagation of reference light, or withdraws.

Thus, the optical path length of the reference light can be adjusted. Moreover, a magnitude of movement by which the lens 14 is moved by the motor 50 is detected precisely using the encoding signal sent from the encoder 53. The position of the lens 14 can therefore be precisely controlled and identified.

Moreover, the motor control circuit 52 is connected to the computer 18 and actuated under the control of the computer 18. When the optical probe 9 is connected to the observing device 6 included in the optical imaging system 1, the computer 18 detects and acquires probe feature information, which specifies the length of the optical probe 9, by means of a probe information automatic detecting means. The computer 18 then controls the motor 50 according to the length of the optical probe 9 by means of the motor rotation control circuit 52. Thus, the optical path length of reference light is adjusted to agree with the optical path length of measurement light beam.

FIG. 10 to FIG. 14 are concerned with different types of optical probes whose sheaths have different diameters. Herein, by adjusting the optical path length of reference light using the optical path length adjusting mechanism 13b shown in FIG. 8, the size of an image of a sheath superposed on an OCT image is adjusted so that the reading on a scale of the diameter of the sheath image delineated on the image will correspond to the actual diameter of the probe.

FIG. 10 and FIG. 11 show an optical probe 61 whose sheath has a diameter d1, and an optical probe 62 whose sheath has a diameter d2. An OCT image produced by employing the optical probe 61 is shown in FIG. 12.

Referring to FIG. 12, an image 63 of the sheath of the optical probe 61 has a diameter d1 corresponding to the diameter d1 of the sheath of the optical probe 61. An image of a region of interest 64a has a size in proportion to the diameter d1 of the sheath image. Moreover, a scale 65 is delineated on an OCT image 30c.

In this state, assume that the optical probe 62 whose optical path length is identical to the optical path length of the optical probe 61 and whose sheath has the diameter d2 is substituted for the optical probe 61. A produced OCT image 30d is shown in FIG. 13. Incidentally, an image 66a of the sheath of the optical probe 62 has the same diameter as the diameter d1 of the image 63 of the sheath of the optical probe 61 shown in FIG. 12. The image of the region of interest 64a shown in FIG. 12 is changed to the image of a region of interest 64b whose size is smaller as shown in FIG. 13. Thus, when the diameter of the sheath of an optical probe varies, the magnification of the OCT image 30c or 30d changes.

In efforts to solve the above problem, the present embodiment uses a probe feature information detecting means to acquire the diameter of the sheath of an optical probe connected to the optical imaging system 1. The optical path length adjusting mechanism 13b shown in FIG. 8 is used to automatically adjust the optical path length of reference light. The diameter of the image of the sheath of the optical probe superposed on an OCT image is matched with the reading on the scale corresponding to the actual diameter of the optical probe. Thus, the magnification of the OCT image is matched with the reading on a scale.

For example, assume that the optical probe 62 whose sheath has the diameter d2 is connected. In this case, the computer 18 recognizes the diameter d2 of the sheath of the optical probe 62 by means of the probe feature information detecting means. The computer 18 then automatically adjusts the optical path length of reference light using the optical path length adjusting mechanism 13b shown in FIG. 8. Consequently, as shown in FIG. 14, the diameter of the representation of the sheath of the optical probe 6 which is superposed on an image is set to a value d2.

Consequently, the OCT image 30e produced using the optical probe 62 (FIG. 14) and the OCT image 30c produced using the optical probe 61 (FIG. 12) share the same magnification. The diameter of the image 66b of the sheath of the optical probe 62 is d2/d1 times larger than the diameter of the representation 63 of the sheath of the optical probe 61. The sizes of the representations of the region of interest 64a of the same object shown in FIG. 14 and FIG. 12 are the same as each other.

FIG. 15 is an explanatory diagram concerning a method of delineating a focal position or focal range offered by an optical probe in an OCT image according to feature information specifying the focal position or focal range offered by an optical probe.

In an OCT image, a focal point and its surroundings are visualized as images having high-definition and higher directional resolution. Points farther than the focal point are visualized with lower directional resolutions. An operator who is observing an object must operate the optical imaging system so that a region of interest will coincide with the focal point offered by the imaging system. However, in the conventional optical imaging systems, it is not easy to find a focal point. The above operation must be achieved through visual observation, and therefore requires too much time.

Moreover, when a plurality of types of optical probes is employed, since the focal points offered by the probes are different from one another, it is quite hard to determine a focal point.

In efforts to solve the above problem, the present embodiment uses the probe feature information detecting means to acquire focal point information or focal range information concerning the optical probe 9 included in the optical imaging system 1. Consequently, a focal point or focal range offered by the optical probe 9 can be delineated in an OCT image.

FIG. 15 shows the structure of the optical probe 9 and also shows a focal point 72 of a measurement light beam 71 and a focal range 73 thereof. Assuming that the optical probe 9 is used for diagnosis, when a region of interest coincides with the focal point 72, the region of interest is delineated in an OCT image with a high resolution.

The focal point 72 of the measurement light beam 71 refers to a point at which the measurement light beam 71 becomes thinnest. Depending on the structure of the optical probe 9, the numerical aperture (NA) for the measurement light beam 71 may be large. In this case, the focal point 72 is located near the sheath 31 of the optical probe 9, and is spatially one point.

When the numerical aperture NA for the measurement light beam 71 is small, the focal point 72 is located far away from the sheath of the optical probe 9. The thinnest portion of the measurement light beam extends over a certain range but does not spatially converge at a point. In this case, the measurement light beam 71 is dealt with as light that converges over the focal range 73.

When the focal point 72 of the measurement light beam 71 is a point, if radial scanning is implemented, a focal point mark 75 is delineated in an OCT radial-scan image 74*a*. The focal point mark 75 indicates the focal point of the measurement light beam 71 propagated from the optical probe 9. When radial scanning is implemented, the focal point mark 75 is circular. The optical imaging system offers high resolutions at and around the focal point 72.

Probe feature information concerning the optical probe 9 connected to the observing device 6 is transmitted to the computer 18. The computer 18 extracts information concerning the focal point 72 offered by the optical probe 9, and displays the focal point mark 75 representing the focal point 72 on the monitor 23 as shown in FIG. 16.

Consequently, when an operator manipulates the optical probe 9 so that an image of a region of interest 76*a*, in which the operator is especially interested, will appear over the focal point mark 75, the region of interest 76*a* is visualized with the best resolution.

When linear scanning is implemented, a focal point mark 80 is delineated as a straight line in a linear image 81*a*. When the representation of the region of interest 76*a* appears over or near the focal point mark 80, it means that the region of interest 76*a* is visualized with the best resolution.

When the focus of the measurement light beam 71 extends over a certain range, if radial scanning is implemented, the computer 18 extends control so that two focal range marks 82 defining the focal range of the measurement light beam 71 propagated from the optical probe 9 will be, as shown in FIG. 18, delineated in an OCT radial image 74*b*.

Consequently, when an operator manipulates the optical probe 9 so that the image of the region of interest 76*c*, in which the operator is especially interested, will appear between the two focal point marks 82, the region of interest 76*c* is visualized with the best resolution.

When a linear scanning is implemented, focal point markers 83 are, as shown in FIG. 19, delineated as two straight lines in a linear-scan image 81*b*. When the image of the region of interest 76*d* appears between the two focal point marks 83, it means that the region of interest 76*d* is visualized with the best resolution.

As mentioned above, in the present embodiment, the attachment 10 of each optical probe (9 and the like) includes the probe information holding means 39 that holds probe information which specifies a scanning method implemented in the optical probe, an optical path length (diameter of the sheath) of the optical probe, the diameter of the sheath as display parameters for an OCT image and a focal point or range. When an optical probe is connected to the observing device 6, the probe information held in the probe information holding means 39 is automatically detected or checked in order to designate the scanning method implemented in the actually connected optical probe, adjust the optical path length of reference light, or designate the display parameters. Consequently, a user is relieved from time-consuming work of switching or adjustment, and can easily and quickly perform an examination to produce an OCT image. Thus, the present embodiment has succeeded in improving user-friendliness and maneuverability.

Consequently, the present embodiment provides the advantages described below.

Information concerning the optical probe 9 connected to the observing device 6 can be automatically detected so that the detection does not depend on human being's discernment.

Moreover, information (whether linear scanning or radial scanning is implemented) concerning the optical probe 9 is acquired, and linear scanning, radial scanning, or both of them is automatically carried out according to a control sequence associated with the optical probe 9. This results in the improved maneuverability of the system.

Moreover, automatic adjustment of an optical path length based on automatic detection of probe information contributes to improved maneuverability and accuracy compared with conventional human being's discernment and manual adjustment.

Moreover, a representation of the sheath of a probe produced through automatic adjustment of an optical path length based on automatic detection of probe information is displayed with the diameter thereof equal to the actual diameter of the sheath of the probe. Consequently, when different types of optical probes (whose sheaths have different diameters) are employed, OCT images can be displayed at the same magnification. This means that comparison of images can be acquired.

Furthermore, a focal point or focal range of measurement light beam is delineated in an OCT image, whereby the focal point or focal range can be learnt accurately. When the optical probe is manipulated so that a region of interest will coincide with the focal point, the region of interest can be visualized with the best resolution.

SECOND EMBODIMENT

A second embodiment of the present invention will be described below.

Figure 20:
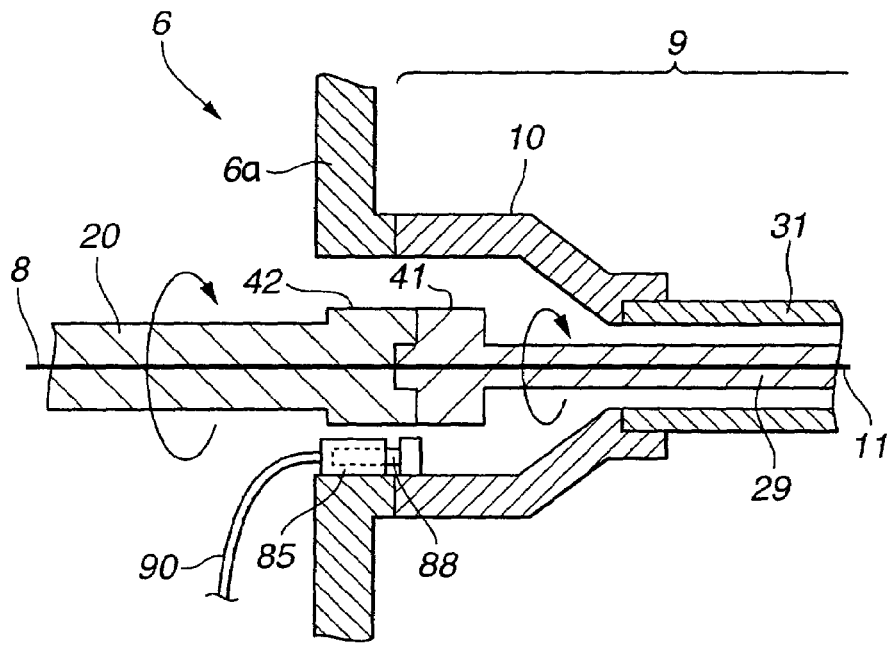
FIG. 20 shows the structure of an optical coupler-inclusive probe information detecting mechanism included in a second embodiment of the present invention.
Figure 21:
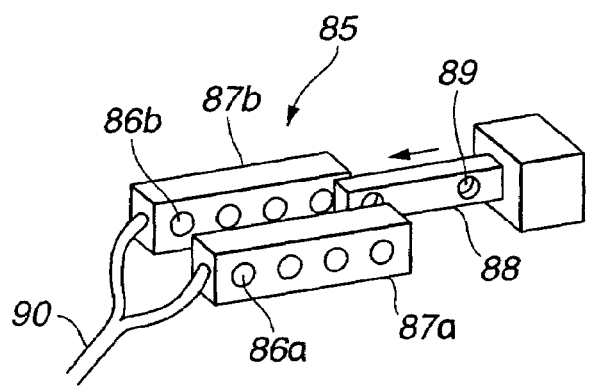
FIG. 21 is a perspective view showing the major portion of the mechanism shown in FIG. 20.
Figure 22:
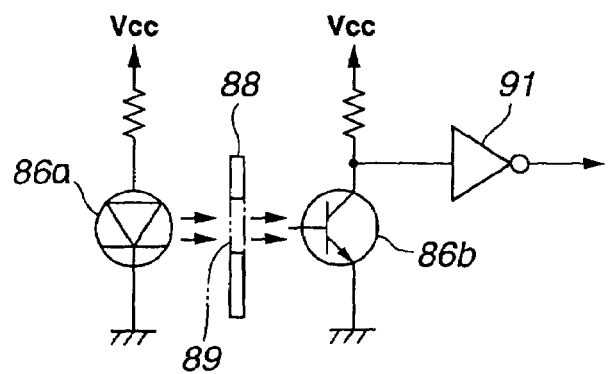
FIG. 22 is an explanatory diagram concerning the principles of operation based on an optical coupler-dependent detecting method.

FIG. 20 to FIG. 22 show a major portion of the second embodiment of the present invention. A photo-sensor assemblage 85 is used as a probe information detecting means, which is disposed in both the joint members included in the optical probe 9 and observing device 6 respectively, in place of a micro-switch-inclusive probe detecting means employed in the first embodiment.

The photo-sensor assemblage 85 composed of a plurality of photo-sensors is incorporated in the joint member 6a included in the observing device 6. Specifically, the photo-sensor assemblage 85 includes a light-emitting element plate 87a on which a plurality of light-emitting elements 86a is mounted, and a light-receiving element plate 87b on which a plurality of light-receiving elements 86b is mounted to face the plurality of light-emitting elements 86a.

Moreover, a light interceptor 88 is included in the attachment 10 of the optical probe 9. When the optical probe 9 is attached to the observing device 6, the light interceptor 88 is, as shown in FIG. 21, interposed between the light-emitting element plate 87a and light-receiving element plate 87b.

The light interceptor 88 has through holes 89 that face in a direction of light emission in which the plurality of light-emitting elements 87a emit light. The light receiving elements 86b communicating with the light-emitting elements 86a by way of the through holes 89 can receive light from the light-emitting elements 86a (on state). The light-receiving elements 86b not facing the through holes 89 cannot receive light from the light-emitting elements 86a (off state).

The light-receiving elements 86b and light-emitting elements 86a are interconnected over a cable 90. The cable 90 is routed to a detection circuit incorporated in the computer 18. The computer 18 detects the situation of the photo-sensor assemblage 85 receiving light, and thus acquires feature information concerning the optical probe 9.

FIG. 22 shows the electrical circuitry including a pair of light-emitting element 86a and light-receiving element 86b. Light emanating from the light-emitting element 86a is intercepted by the light interceptor 88 but does not enter in the light-receiving element 86b, for example, a photo-transistor. In this case, the photo-transistor becomes non-conducting, and the collector output inverted by an inverter 91 is driven to an off-state (low) level.

On the other hand, when the light interceptor 88 has the through hole 89 opposed to the pair of light-emitting element 86a and light-receiving element 96b, light emanating from the light-emitting element 86a passes through the through hole 89 and enters in the light-receiving element 86b. In this case, the output inverted by the inverter 91 is driven to an on-state (high) level.

The arrangement pattern of the through holes 89 in the light interceptor 88 is corresponding to a type of the optical probe 9. A square of the number of photo-sensors included in the photo-sensor assemblage 85 corresponds to the number of detectable types of the optical probes 9. For example, as shown in FIG. 21, if the number of photo-sensors is four, the number of detectable types of probes is 16. The present embodiment adopts a method of intercepting light that emanates from the light-emitting elements 86a. Alternatively, a method of reflecting the light may be adopted.

The present embodiment provides the advantages described below.

According to the second embodiment, compared with the first embodiment, a more inexpensive and compact optical imaging system can be realized due to adoption of a photo-sensor.

In the present embodiment, a plurality of photo-sensors juxtaposed in the axial direction can be disposed at one position on the circumference. This contributes to simplification of the system configuration.

THIRD EMBODIMENT

Figure 23:
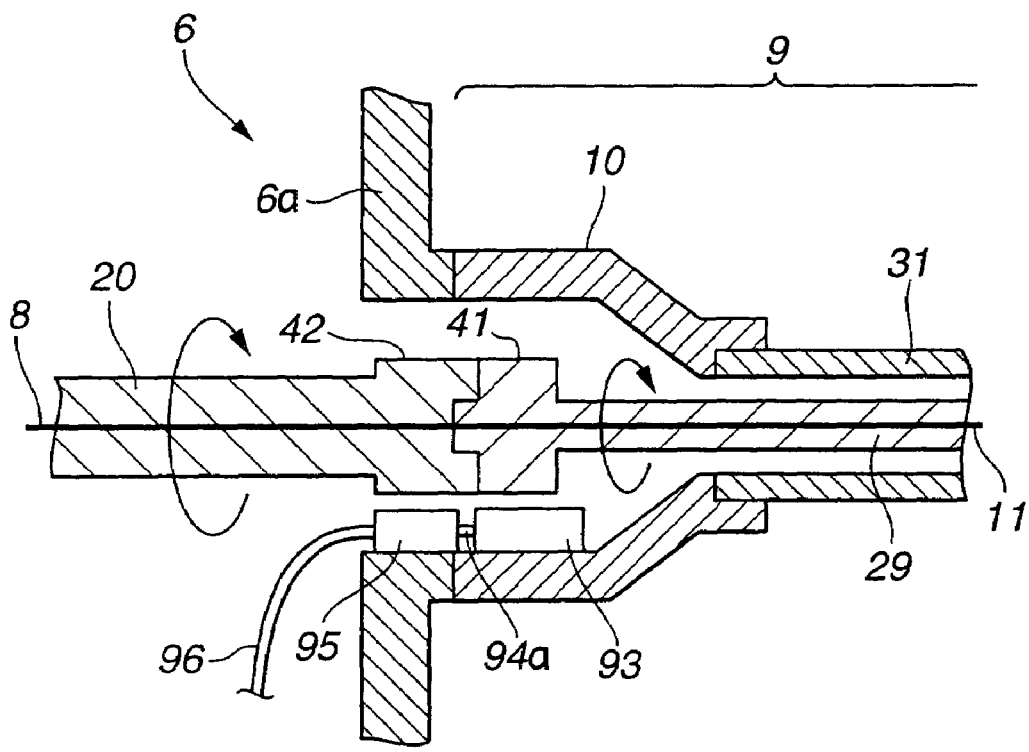
FIG. 23 shows the structure of a memory-inclusive probe information detecting mechanism included in a third embodiment of the present invention.
Figure 24:
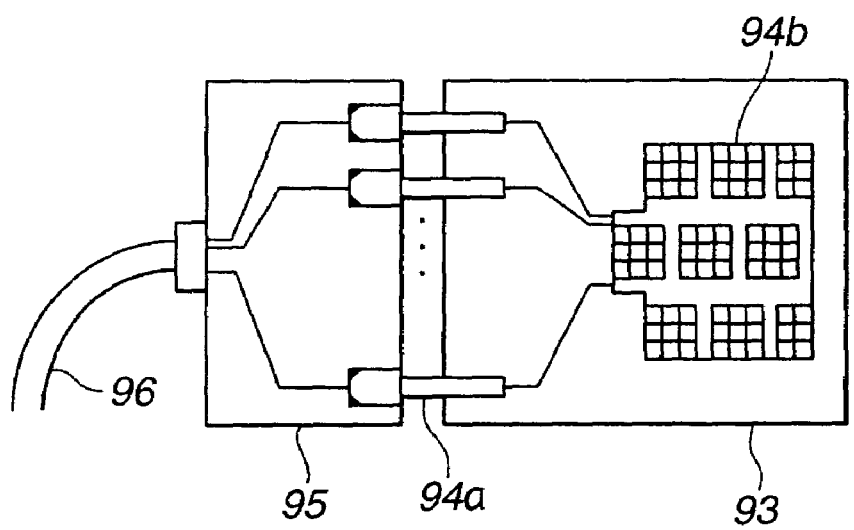
FIG. 24 is an explanatory diagram concerning the principles of operation based on a memory-dependent detecting method to be implemented in the mechanism shown in FIG. 23.

FIG. 23 and FIG. 24 show a major portion of a third embodiment of the present invention. In this embodiment, a memory module 93 is adopted as a probe information detecting means that links both the joint members included in the optical probe 9 and observing device 6 respectively.

The memory module 93 is incorporated inside the attachment 10 of the optical probe 9, and connected to a cable connector 95 disposed in the joint member 6a of the observing device 6 through memory connector members 94a connected to the memory module 93.

The memory connector members 94a have pins thereof coupled to a power line or signal lines, and are connected to the computer 18 over a cable 96 that is coupled to pin receptacles included in the cable connector 95.

Power required by the memory module 93 is supplied from the computer 18 over the power line. Probe information recorded in advance in the memory module 93 is in turn read into the computer 18 over the signal lines.

FIG. 24 shows the relationship among the connections. Referring to FIG. 24, memory cells 94b are sealed inside the memory module 93.

As a variant of the memory module 93, a matrix (or array) of electronic elements such as resistors may be substituted for the memory module 93. A power line and signal lines needed to connect the matrix of electric elements (to detect the electric characteristics thereof) are passed through the joint connector and routed to the computer 18. The values indicating the electric characteristics of the electronic elements constituting the matrix are detected as probe feature information. For example, when the electronic elements are resistors, the resistances of the resistors themselves are detected as probe information by the computer 18.

According to the present embodiment, compared with the first and second embodiments, a larger amount of data or information can be recorded or detected.

FOURTH EMBODIMENT

A fourth embodiment of the present invention employs a direct-vision optical probe so as to produce a two-dimensionally observed image (image produced by optical imaging).

Figure 25:
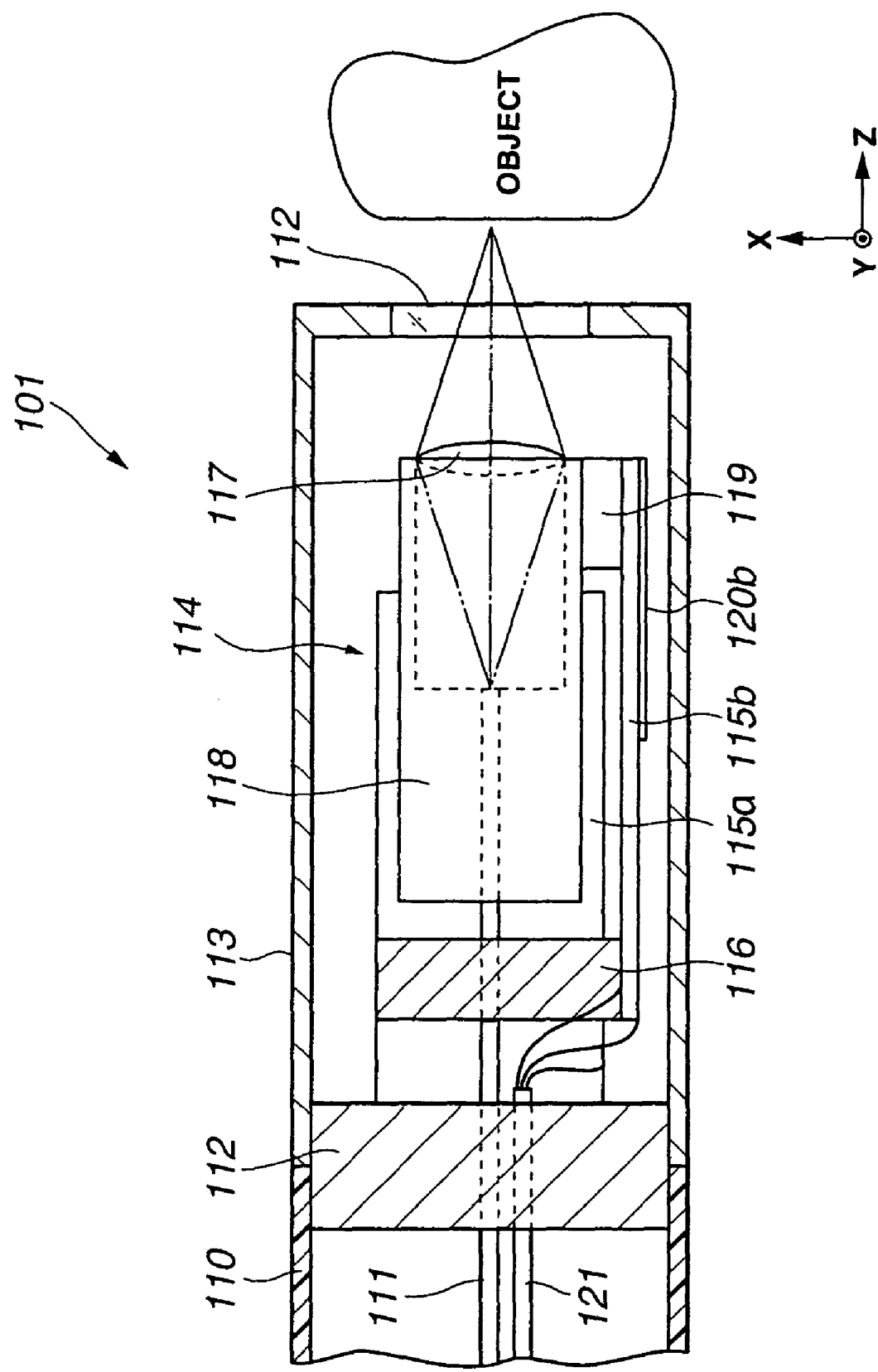
FIG. 25 schematically shows the structure of an optical probe included in an optical imaging system of a fourth embodiment.
Figure 26:
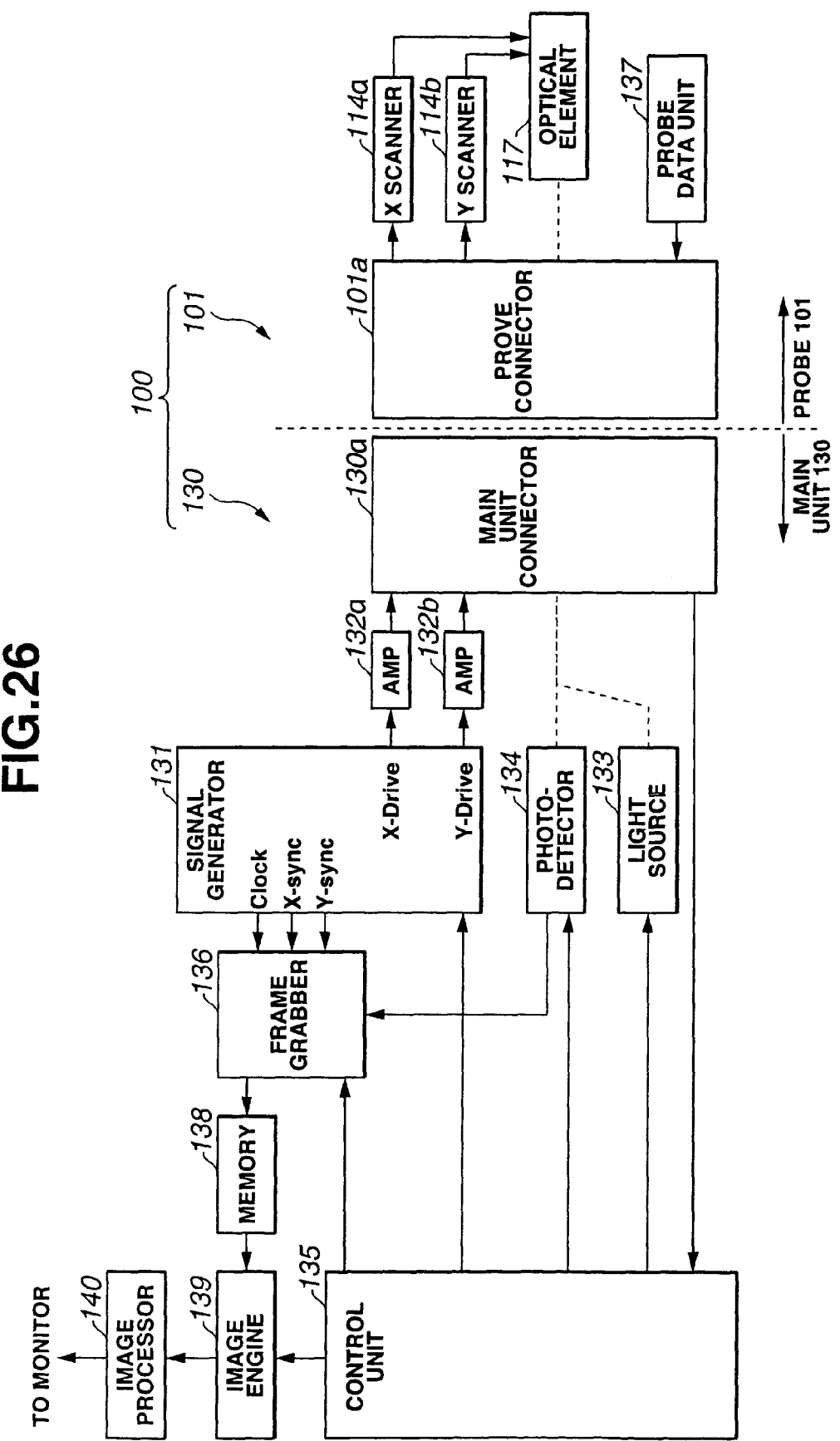
FIG. 26 is a circuit block diagram schematically showing the configuration of the optical imaging system of the fourth embodiment.
Figure 27:
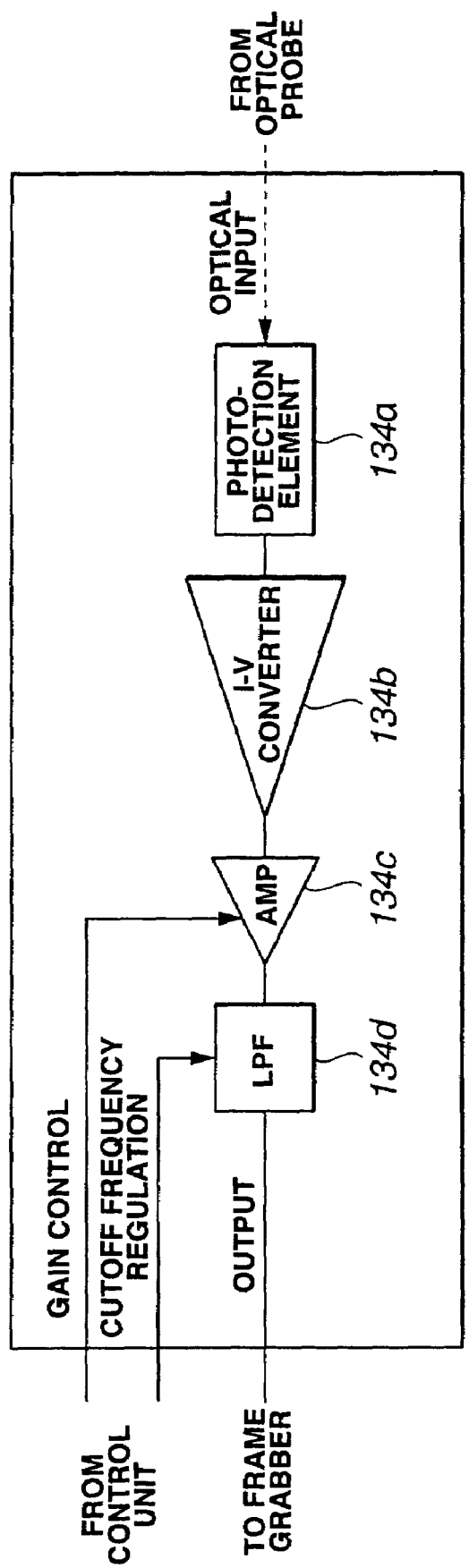
FIG. 27 is a circuit block diagram schematically showing the circuitry of a photo-detector shown in FIG. 26.
Figure 28B:
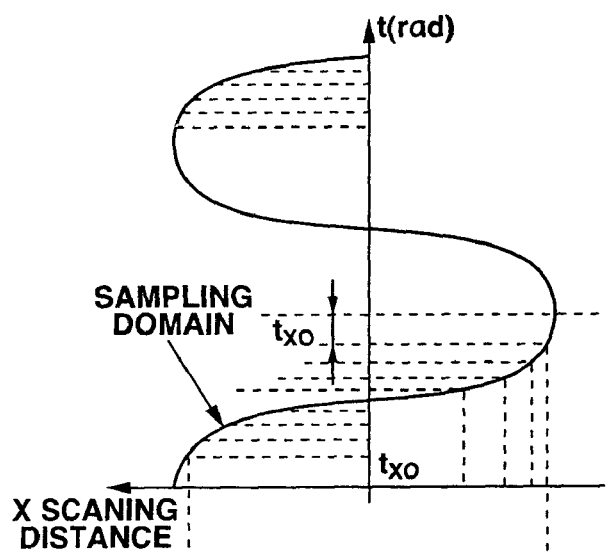
FIG. 28A is an explanatory diagram concerning X and Y scanning of an optical element in X and Y directions; FIG.
FIG. 28C is a graph indicating a driven frequency at which a Y scanner is driven.
FIG. 28D is an explanatory diagram showing sampled image data items that are rearranged in a real space.
Figure 28A:
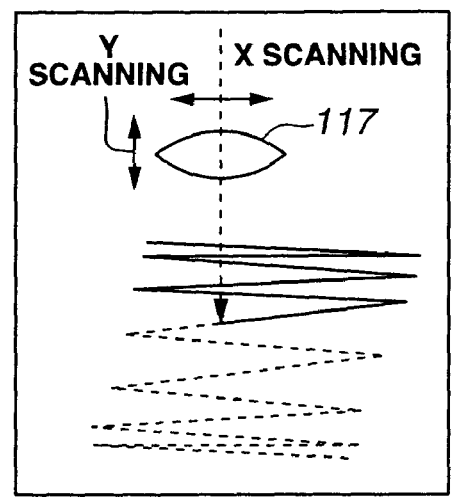
Figure 28D:
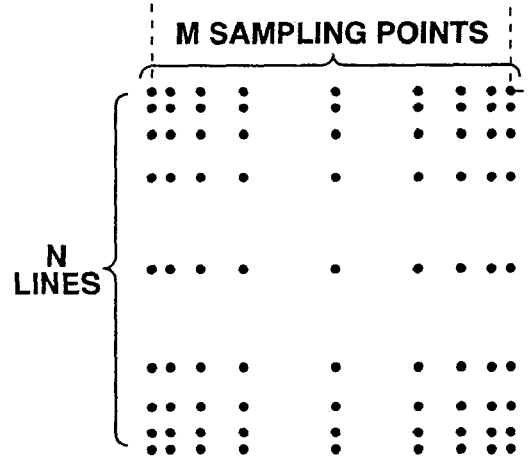
Figure 28C:
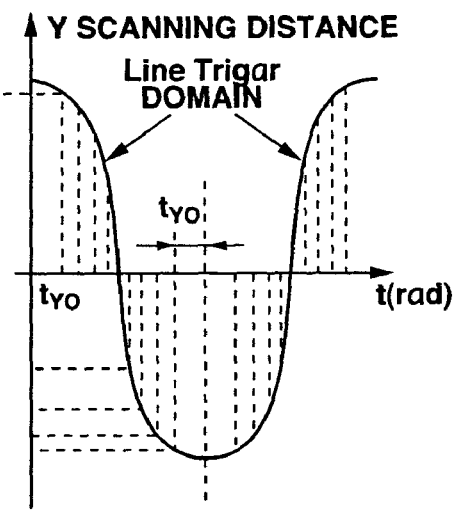
Figure 29:
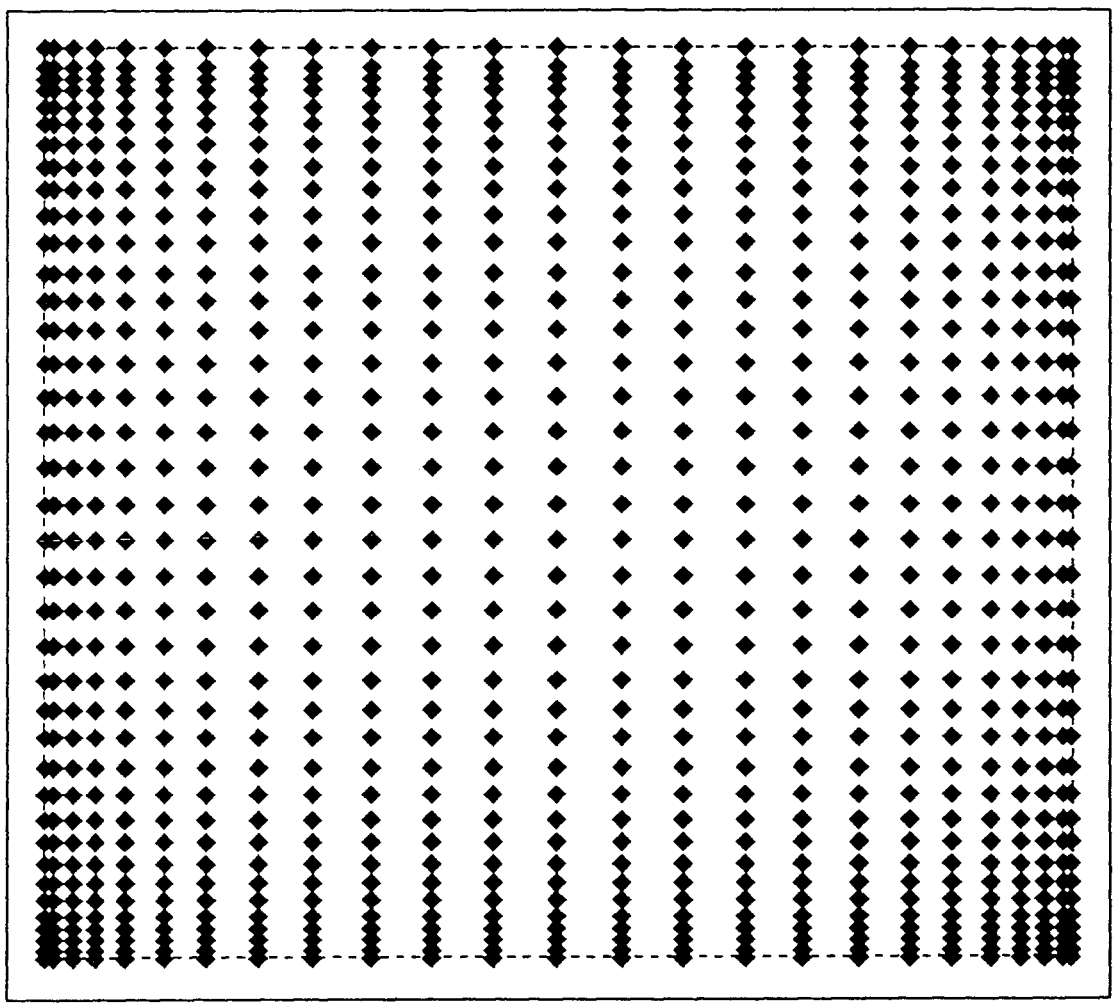
FIG. 29 is an explanatory diagram showing a display image produced by drawing dots at regular intervals according to the image data shown in FIG. 28D.
Figure 31:
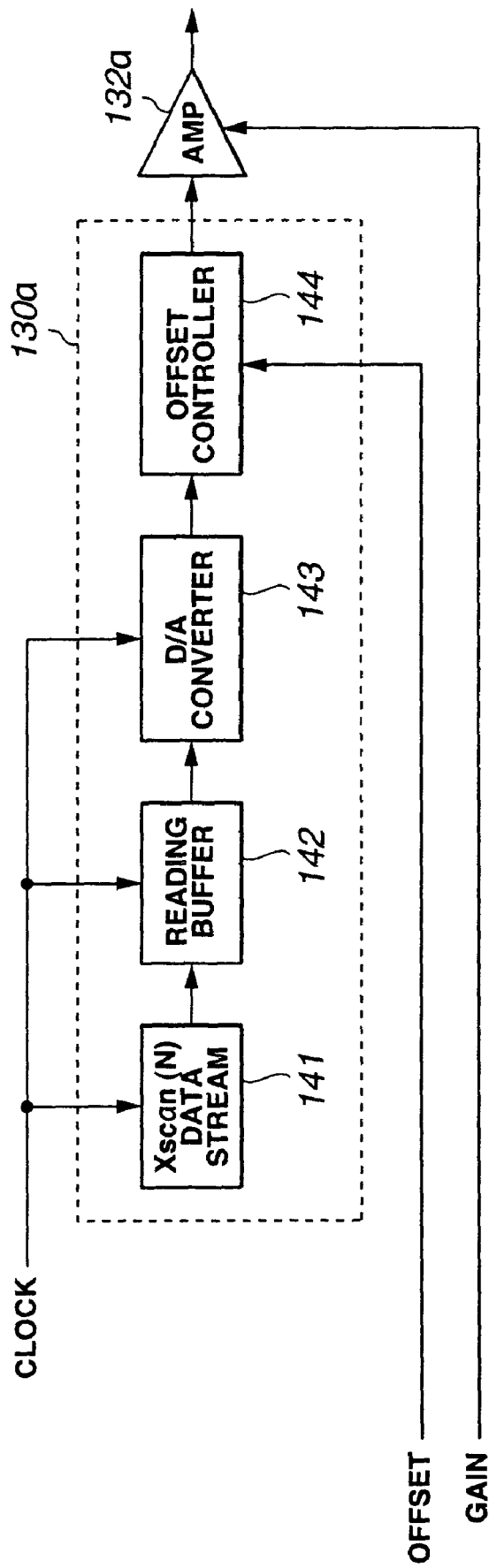
FIG. 31 is a circuit block diagram schematically showing the configuration of an X driver included in a signal generator.
Figure 32:
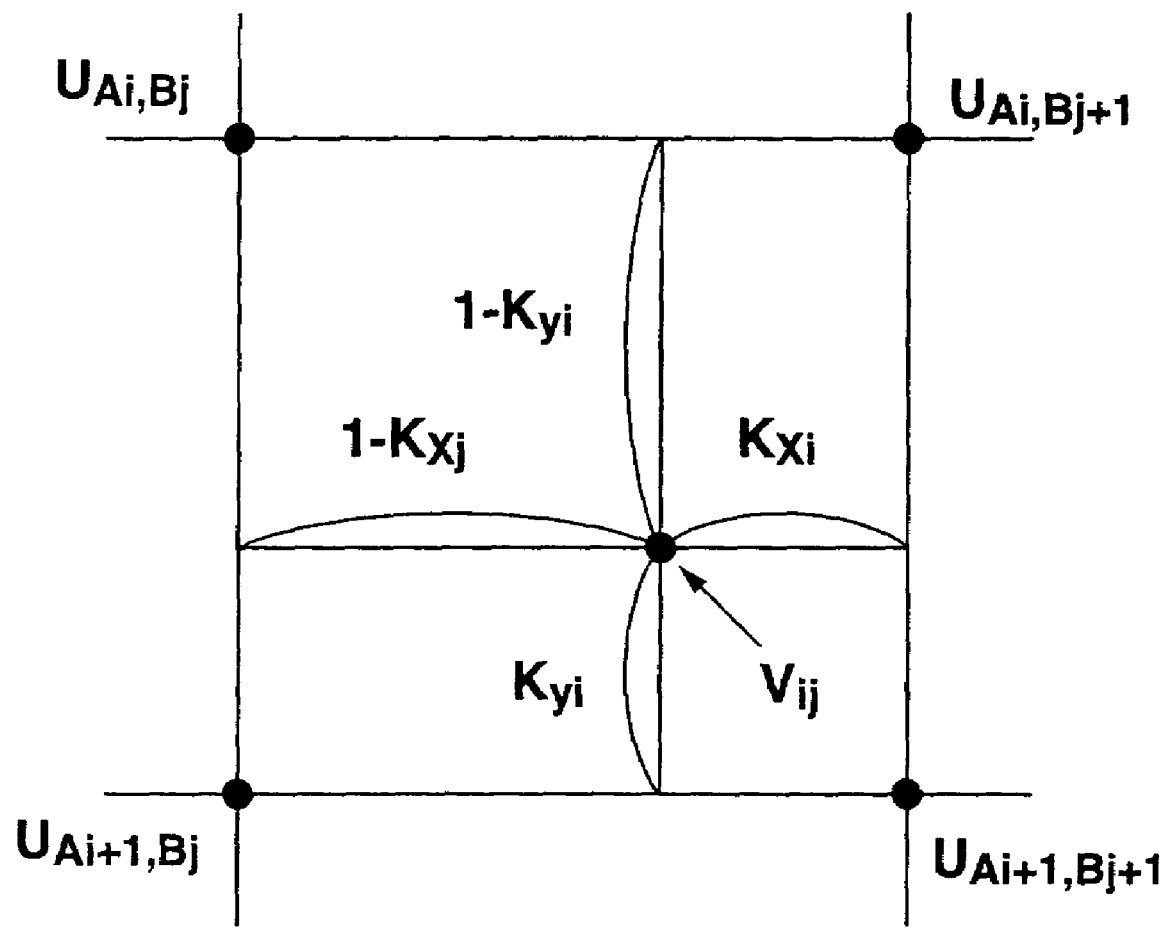
FIG. 32 is a graph for explaining bi-linear interpolation.
Figure 33:
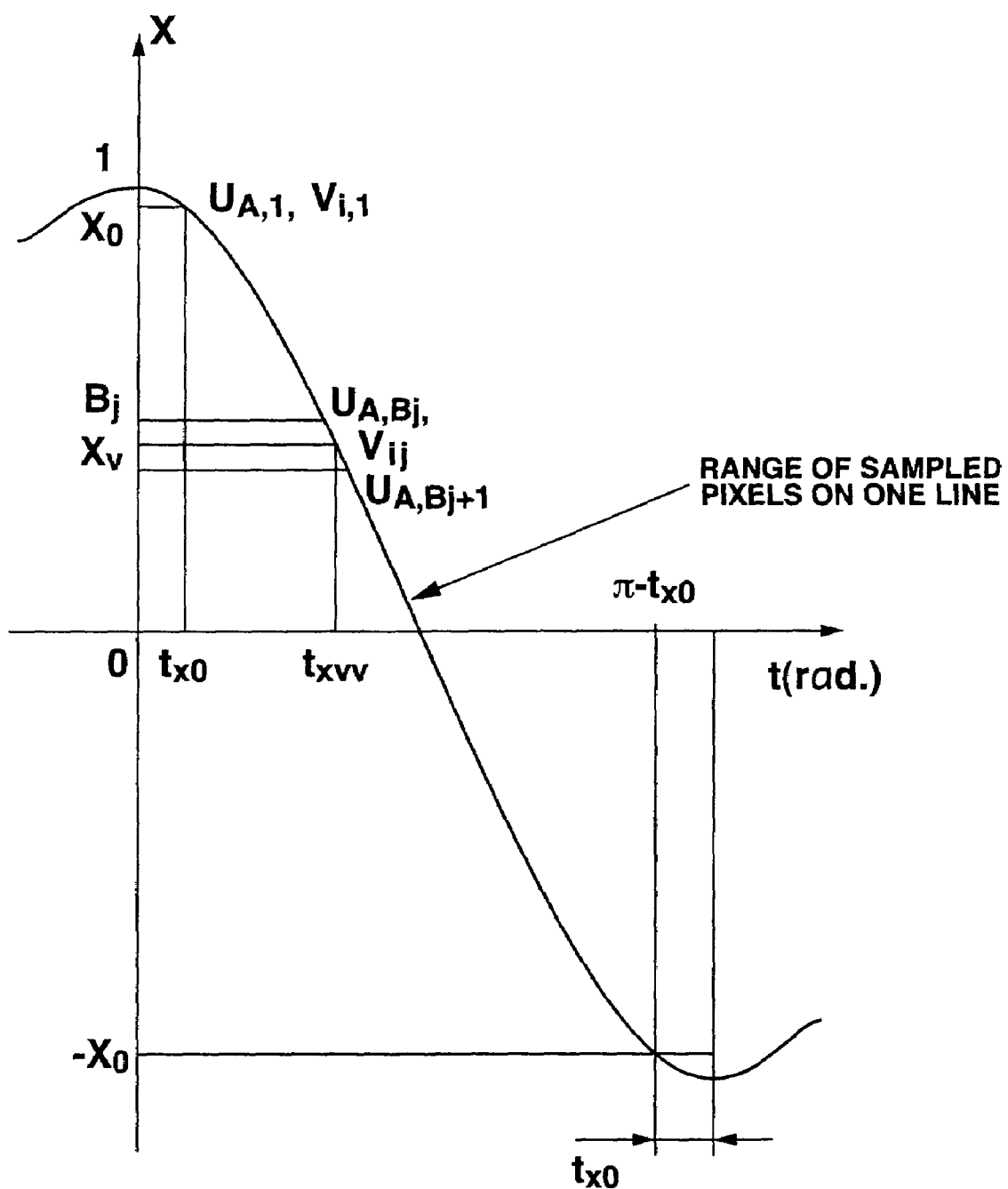
FIG. 33 is a graph indicating the relationship between a data column number Bj and an X-direction interpolation coefficient $Kx_j$.
Figure 34:
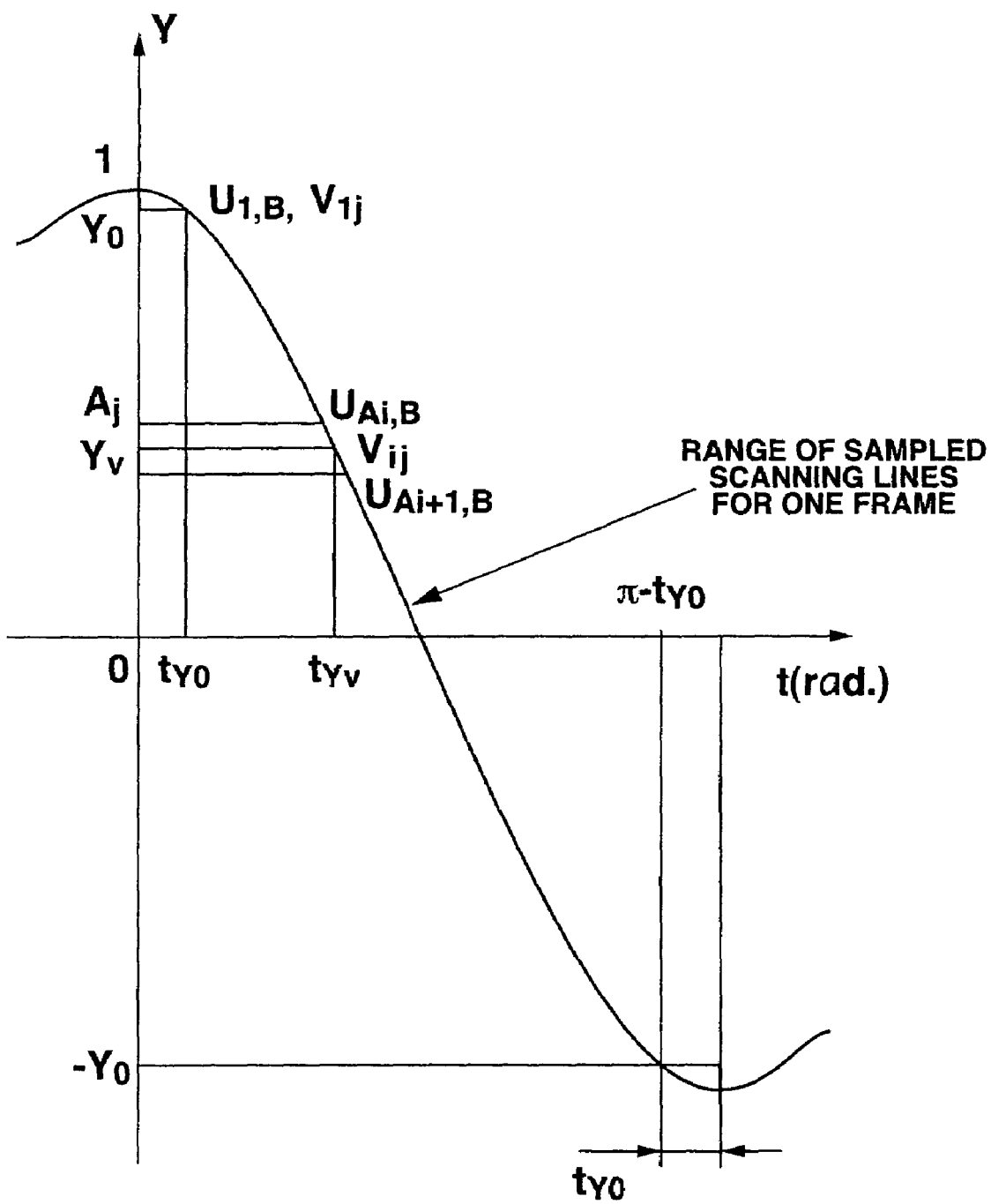
FIG. 34 is a graph indicating the relationship between a data column number Ai and a Y-direction interpolation coefficient Kyi.
Figure 43:
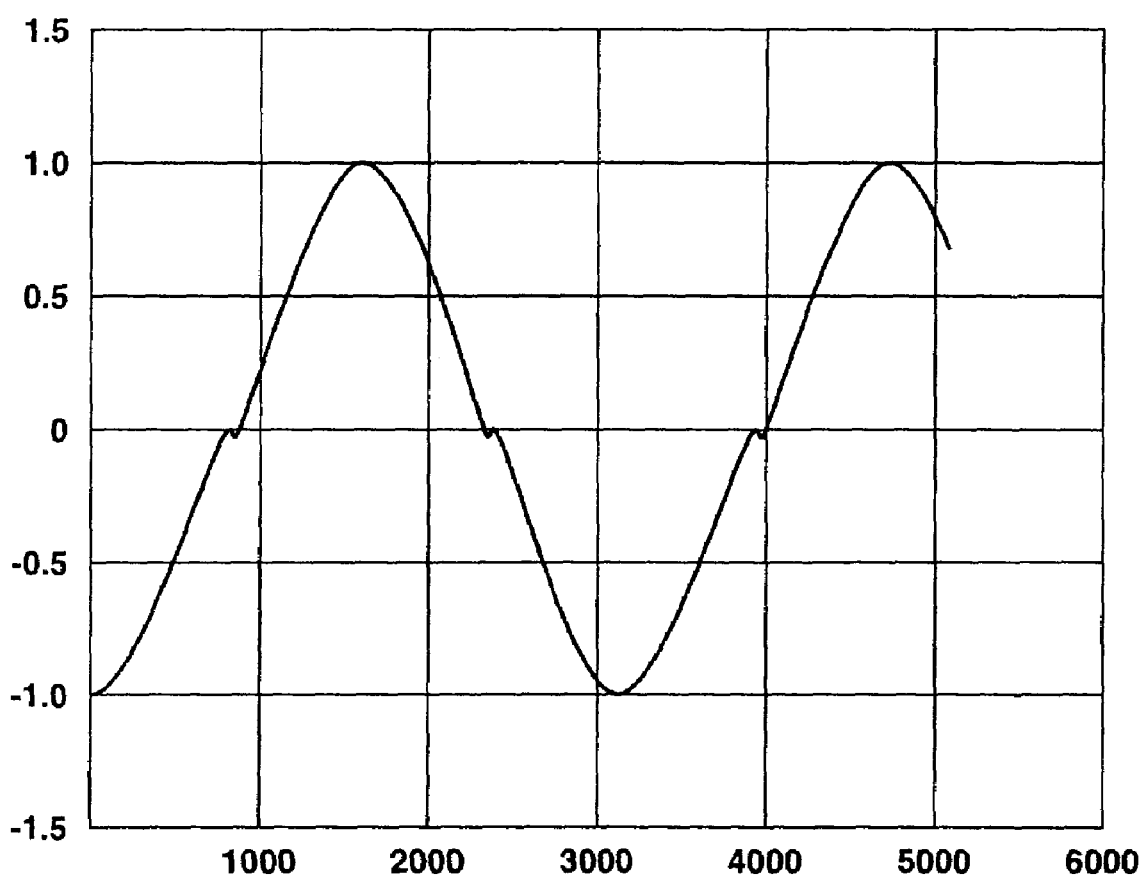
FIG. 43 shows the waveform of a driving signal having a distortion.

FIG. 25 to FIG. 43 are concerned with the fourth embodiment of the present invention. FIG. 25 schematically shows the structure of an optical probe employed in the optical imaging system of the fourth embodiment. FIG. 26 is a circuit block diagram schematically showing the configuration of the optical imaging system of the fourth embodiment. FIG. 27 is a circuit block diagram schematically showing the configuration of a photo-detector shown in FIG. 26. FIGS. 28A–28D include explanatory diagrams concerning sampling of image data acquired by an optical element and scanned by a scanner. FIG. 28A is an explanatory diagram concerning X and Y scanning of the optical elements in X and Y directions. FIG. 28B is a graph indicating a driving frequency at which an X scanner is driven. FIG. 28C is a graph indicating a driving frequency at which a Y scanner is driven. FIG. 28D is an explanatory diagram showing sampled image data items that are rearranged in a real space. FIG. 29 is an explanatory diagram showing a display image that is composed of dots drawn at regular intervals in order to represent the image data items shown in FIG. 28D. FIGS. 30A–30C include data tables to be stored in a probe data unit. FIG. 30A is a data table specifying a type of probe, an optical path length and others. FIG. 30B is a data table specifying the conditions for driving an X scanner. FIG. 30C is a data table specifying the conditions for driving a Y scanner. FIG. 31 is a circuit block diagram schematically showing the configuration of an X drive unit included in a signal generator. FIG. 32 is a graph for explaining a bi-linear interpolation. FIG. 33 and FIG. 34 are graphs concerning the bi-linear interpolation explained in conjunction with FIG. 32 and adapted to the present embodiment. FIG. 33 is a graph used to detect the relationship between a data column number Bj and an X-direction interpolation coefficient $Kx_j$. FIG. 34 is a graph used to detect the relationship between a data column number Ai and a Y-direction interpolation coefficient $Ky_j$. FIGS. 35A–35B include explanatory diagrams concerning interpolation of image data. FIG. 35A is an explanatory diagram showing sampled image data items rearranged in the real space. FIG. 35B is an explanatory diagram concerning an interpolation extraction, performed in an odd frame using the bi-linear interpolation method in the state shown in FIG. 35A. FIG. 35C is an explanatory diagram concerning aliasing of data, performed in an even frame, in the state shown in FIG. 35B. FIG. 36 to FIGS. 42A–42G are timing charts each including graphs that indicate the timings of signals produced by a signal generator. FIGS. 36A–36E include a timing chart including graphs that indicate the timings of signals produced by the signal generator in a steady state. FIG. 36A is a graph showing the waveform of a Y driving signal that is a driving signal with which a Y scanner is driven. FIG. 36B is a graph showing the waveform of a Y-U/D signal with which it is discriminated whether the Y scanner driven with the Y driving signal shown in FIG. 36A is on the outward sweep or homeward sweep. FIG. 36C is a graph showing the waveform of a Y triggering signal (Y-Sync). FIG. 36D is a graph showing the waveform of an X triggering signal (X-Sync). FIG. 36E is a graph showing the waveform of a signal having a clock frequency fs. FIGS. 37A–37G include a timing chart including graphs that indicate the timings of signals produced when the Y driving signal assumes a maximum positive value. FIG. 37A is a graph showing the waveform of the Y driving signal that is a driving signal with which the Y scanner is driven. FIG. 37B is a graph showing the waveform of the (Y-U/D) signal with which it is discriminated whether the Y scanner driven with the Y driving signal shown in FIG. 37A is on the outward sweep or homeward sweep. FIG. 37C is a graph showing the waveform of the Y triggering signal (Y-Sync). FIG. 37D is a graph showing the waveform of the X triggering signal (X-Sync). FIG. 37E is a graph showing the waveform of a signal having the clock frequency fs. FIG. 37F is a graph showing the waveform of an X driving signal that is a driving signal with which the X scanner is driven. FIG. 37G is a graph showing an angle by which an optical element whose input is scanned by the X scanner is driven in an X direction. FIGS. 38A–38G include a timing chart including graphs that indicate the timings of signals produced when the Y triggering signal (Y-Sync) is produced in order to initiate a (homeward) sweep for producing the first frame. FIG. 38A is a graph indicating the waveform of the Y driving signal that is a driving signal with which the Y scanner is driven. FIG. 38B is a graph indicating the waveform of the (Y-U/D) signal with which it is discriminated whether the Y scanner driven with the Y driving signal shown in FIG. 38A is on the outward sweep or homeward sweep. FIG. 38C is a graph indicating the waveform of the Y triggering signal (Y-Sync). FIG. 38D is a graph indicating the waveform of the X triggering signal (X-Sync). FIG. 38E is a graph indicating the waveform of a signal having the clock frequency fs. FIG. 38F is a graph indicating the waveform of the X driving signal that is a driving signal with which the X scanner is driven. FIG. 38G is a graph indicating an angle by which the optical element whose input is scanned by the X scanner is driven in the X direction. FIGS. 39A–39G include a timing chart including graphs that indicate the timings of signals produced immediately before sampling of data representing one frame is completed. FIG. 39A is a graph indicating the waveform of the Y driving signal that is a driving signal with which the Y scanner is driven. FIG. 39B is a graph indicating the waveform of the (Y-U/D) signal with which it is discriminated whether the Y scanner driven with the Y driving signal shown in FIG. 39A is on the outward sweep or homeward sweep. FIG. 39C is a graph indicating the waveform of the Y triggering signal (Y-Sync). FIG. 39D is a graph indicating the waveform of the X triggering signal (X-Sync). FIG. 39E is a graph indicating the waveform of a signal having the clock frequency fs. FIG. 39F is a graph indicating the waveform of the X driving signal that is a driving signal with which the X scanner is driven. FIG. 39G is a graph indicating an angle by which the optical element whose input is scanned by the X scanner is driven in the X direction. FIGS. 40A–40G include a timing chart including graphs that indicate the timings of signals produced when the Y driving signal assumes a maximum negative value. FIG. 40A is a graph indicating the waveform of the Y driving signal that is a driving signal with which the Y scanner is driven. FIG. 40B is a graph indicating the waveform of the (Y-U/D) signal with which it is discriminated whether the Y scanner driven with the Y driving signal shown in FIG. 40A is on the outward sweep or homeward sweep. FIG. 40C is a graph indicating the waveform of the Y triggering signal (Y-Sync). FIG. 40D is a graph indicating the waveform of the X triggering signal (X-Sync). FIG. 40E is a graph indicating the waveform of a signal having the clock frequency fs. FIG. 40F is a graph indicating the waveform of the X driving signal that is a driving signal with which the X scanner is driven. FIG. 40G is a graph indicating an angle by which the optical element whose input is scanned by the X scanner is driven in the X direction. FIGS. 41A–41G include a timing chart including graphs that indicate the timings of signals produced when the Y triggering signal (Y-Sync) is produced in order to initiate a (homeward) sweep for producing the second frame. FIG. 41A is a graph indicating the waveform of the Y driving signal that is a driving signal with which the Y scanner is driven. FIG. 41B is a graph indicating the waveform of the (Y-U/D) signal with which it is discriminated whether the Y scanner driven with the Y driving signal shown in FIG. 41A is on the outward sweep or homeward sweep. FIG. 41C is a graph indicating the waveform of the Y triggering signal (Y-Sync). FIG. 41D is a graph indicating the X triggering signal (X-Sync). FIG. 41E is a graph indicating the waveform of a signal having the clock frequency fs. FIG. 41F is a graph indicating the waveform of the X driving signal that is a driving signal with which the X scanner is driven. FIG. 41G is a graph indicating an angle by which the optical element whose input is scanned by the X scanner is driven in the X direction. FIGS. 42A–42G include a timing chart including graphs that indicate the timings of signals produced immediately before sampling data that represents the second frame is completed. FIG. 42A is a graph indicating the waveform of the Y driving signal that is a driving signal with which the Y scanner is driven. FIG. 42B is a graph indicating the waveform of the (Y-U/D) signal with which it is discriminated whether the Y scanner driven with the Y driving signal shown in FIG. 42A is on the outward sweep or homeward sweep. FIG. 42C is a graph indicating the waveform of the Y triggering signal (Y-Sync). FIG. 42D is a graph indicating the waveform of the X triggering signal (X-Sync). FIG. 42E is a graph indicating the waveform of a signal having the clock frequency fs. FIG. 42F is a graph indicating the waveform of the X driving signal that is a driving signal with which the X scanner is driven. FIG. 42G is a graph indicating an angle by which the optical element whose input is scanned by the X scanner is driven in the X direction. FIG. 43 is a graph indicating the waveform of a driving signal having a distortion.

Now, the conventional optical imaging systems have not taken measures to correct an individual difference of an optical probe that is freely detachably attached to a device main body. According to the present embodiment, the settings of an optical imaging system dependent on the characteristics of an optical probe can be determined easily. In short, according to an optical imaging system and an optical imaging detection method in accordance with the present embodiment, the characteristics of an optical probe are detected, and designating means is used to designate the conditions for operation on the basis of the detected information.

Moreover, the conventional optical imaging systems include scanning means realized with a scanner but is not designed to control image producing means in consideration of the characteristics of an optical probe. According to the present embodiment, based on the characteristics of an optical probe, the settings for producing an image that is scaled accurately and is devoid of a distortion can be easily determined, and an image devoid of a distortion can be easily produced. An optical imaging system in accordance with the present embodiment includes interpolating means. Consequently, even when data is sampled at irregular intervals, an image scaled accurately and devoid of a distortion can be displayed. Moreover, the settings of the interpolating means can be determined based on the characteristic information concerning an optical probe. Thus, the settings optimal to the optical probe can be determined easily.

As shown in FIG. 25, a direct-vision type optical scanning probe (hereinafter abbreviated to an optical probe) 101 employed in an optical imaging system 100 of the present embodiment has a fiber 111 such as a single-mode fiber or a multi-mode filter passed through a sheath 110 thereof.

The sheath 110 has the distal end thereof joined with a cylindrical hard distal cover 113 by way of a hard base member 112. The base member 112 has a first sheet 115a that can deform and is included in a scanner 114. The first sheet 115a is disposed so that the back end of a second sheet 115b capable of deforming freely will cross the first sheet 115a at right angles via a relay member 116. The second sheet 115b has a holder 118, which includes an optical element 117 serving as a convergent optical system, held at the distal end thereof via a coupling member 119.

Moreover, the first sheet 115a has a flat first piezoelectric element mounted on the surface thereof. The second sheet 115b has a flat second piezoelectric element 120b mounted on the surface thereof. The first piezoelectric element and second piezoelectric element 120b (electrodes mounted on the surfaces thereof) are connected to the main body, which will be described later, over a driving cable 121. The first piezoelectric element and second piezoelectric element 120b (electrodes mounted on the surfaces thereof) are driven with application of an ac driving signal under the control of the main body. Consequently, the optical element 117 can be driven in a direction orthogonal to the direction of the piezoelectric element.

For example, when the optical probe 101 has the second piezoelectric element 120b driven, the optical element 117 is driven vertically (in an X direction in the coordinate system shown in FIG. 25) together with the holder 118. In other words, the second piezoelectric element 120b and second sheet 115b constitute an X scanner that will be described later. When the optical probe 101 has the first piezoelectric element driven, the relay member 116 is driven in a direction perpendicular to the sheet of paper of FIG. 25. With the driving, the optical element 117 is driven in the direction perpendicular to the sheet of paper (in a Y direction in the coordinate system shown in FIG. 25). That is to say, the first piezoelectric element and first sheet 115a constitute a Y scanner that will be described later.

Specifically, in the optical probe 101, the scanner 114 composed of the X scanner and Y scanner scans light emitted from the optical element 117 two-dimensionally on the XY plane. The optical probe 101 is not limited to the one whose scanner 114 has the structure shown in FIG. 25. Various structures shown in the drawings shown, for example, in Japanese Unexamined Patent Application Publication No. 2001-174744 may be adopted as the structure of the scanner 114. Moreover, the optical probe 101 has an opening formed in the distal end face of the cover 37 and opposed to the optical element 117. The opening is blocked with a protective cover glass 122.

The direct-vision optical probe 101 is, as shown in FIG. 26, connected to a main body 130 with a probe connector 101a freely detachably attached to a main body connector 130a formed in the main body 130, whereby the optical imaging system 100 is constructed.

As shown in FIG. 26, the optical probe 101 includes the X scanner 114a and Y scanner 114b that constitute the scanner 114. The X scanner 114a and Y scanner 114b are driven in order to scan the optical element 117 two-dimensionally on the XY plane.

The X scanner 114a and Y scanner 114b are connected to a signal generator 131 incorporated in the main body 130 through the probe connector 101a and main body connector 130a. Driving signals produced by the signal generator 131 are amplified by amplifiers 132a and 132b, and transmitted for the purpose of driving and control.

Measurement light beam emanating from a light source 133 included in the main body 130 is propagated to the optical element 117 through the probe connector 101a and main body connector 130a over a fiber such as a single-mode fiber.

The optical element 117 irradiates the measurement light beam to an object while being scanned two-dimensionally on the XY plane by the scanner 114. The optical element 117 picks up light returned from the object. The picked up return light is propagated to the main body 130 by reversely tracing the path traced by the measurement light beam. A photo-detector 134 incorporated in the main body 130 receives the return light and converts it into an electric signal. The photo-detector 134 adjusts a gain to be given to the electric signal or filters the electric signal.

As shown in FIG. 27, in the photo-detector 134, a photo-detection element 134a realized with a photo-diode (PD) or a photomultiplier tube (PMT) receives return light and converts it into an electric signal. The electric signal transmitted from the photo-detection element 134a is I-V (current-to-voltage) converted by an I-V converter 134b, and amplified by an amplifier (AMP) 134c. At this time, a gain to be given by the amplifier 133c is controlled based on a gain control signal sent from a control unit 135.

The amplified electric signal has low-frequency components thereof cut off by a low-pass filter (LPF) 134d according to a cutoff frequency adjustment signal sent from the control unit 135, and has thus a noise removed therefrom. The resultant signal is transmitted to a frame grabber 136. The control unit 135 transmits the control signals to the amplifier 134c and low-pass filter 134d respectively on the basis of data stored in a probe data unit 137.

Referring back to FIG. 26, the frame grabber 136 is a frame memory board including a frame memory in which sampling of an electric signal received from the photodetector 134, which are acquired based on a signal generated by the signal generator 131, are stored as image data representing one frame, and an A/D converter that analog-to-digital (A/D) converts image data. The frame grabber 136 temporarily stores the analog-to-digital converted image data, frame by frame, in a memory 138 of the next stage. The image data is then outputted to an image engine 139.

The image engine 139 interpolates the image data to rearrange the data items, and then outputs the resultant data items to an image processor 140 (see FIGS. 35A–35C). The image processor 140 performs signal processing including DIB conversion, gain/contrast control, gamma correction, resizing, and displaying/transferring, and outputs the resultant signal to a monitor that is not shown. Eventually, an observed image (image produced by optical imaging) is displayed on the display surface of the monitor.

Herein, according to the present embodiment, the optical element 117 is, as shown in FIG. 28A to FIG. 28C, X-scanned and Y-scanned in X directions and Y directions by the X scanner 114a and Y scanner 114b respectively. If image data items sampled at regular temporal intervals by the frame grabber 136 are rearranged in the real space, they look like, as shown in FIG. 28D, being sampled at unequal spatial intervals.

If the image data items shown in FIG. 28D are, as shown in FIG. 29, expressed with dots arranged at equal temporal intervals, the resultant image suffers a distortion. Moreover, the positions of the dots disagree with the sampling points of the image data items.

In efforts to solve the above problem, image data must be corrected so that a resultant image will not suffer a distortion before an image represented by the image data is displayed.

According to the present embodiment, as described later in relation to the image engine 139, image data items are interpolated in order to rearrange them (see FIGS. 35A–35C).

Moreover, according to the present embodiment, the optical probe 101 includes the probe data unit 137 in which driving information inherent to the probe is stored. The control unit 135 reads the information in the probe data unit 137. Based on the read driving information, the control unit 135 predefines a range of adjustable values or the like within which each setting can be adjusted and which is needed to optimize the optical characteristics of the optical scanner probe 2. Compared with a case where the driving information is not read, the optical characteristics of the optical probe can be optimized quickly.

The control unit 135 is connected to the light source 133, photo-detector 134, and image engine 139, and controls them according to the information read from the probe data unit 137. Moreover, the control unit 135 is connected to the signal generator 131 that produces signals with which the X scanner 114a, Y scanner 114b, and frame grabber 136 are driven and controlled. The X scanner 114a, Y scanner 114b, frame grabber 136, and image engine 139 are driven and controlled with the signals which are produced by the signal generator 131 under the control of the control unit 135.

The signal generator 131 produces driving signals of, for example, sine waves with which the X scanner 114a and Y scanner 114b are driven. The produced driving signals are transmitted through an X-driving terminal (X-Drive) and a Y-driving terminal (Y-Drive).

Moreover, the signal generator 131 produces a clock signal, synchronously, with which image data inputted to the frame grabber 136 is sampled at equal temporal intervals, while being interlocked with the X scanner 114a and Y scanner 114b. Moreover, the signal generator 131 produces an X triggering signal (X-Sync) and a Y triggering signal (Y-Sync) synchronously with the clock signal.

The signal generator 131 transmits the produced clock signal through a clock terminal thereof, and transmits the produced triggering signals through an X trigger (X-sync) terminal and Y trigger (Y-sync) terminal thereof respectively. Thus, sampling of data in the frame grabber 136 is controlled.

The probe data unit 137 is realized with a nonvolatile memory device such as an EEPROM or a flash memory. Data stored in the probe data unit 137 specifies, for example, parameters listed in FIGS. 30A–30C.

As shown in FIG. 30A, the data stored in the probe data unit 137 specifies a type of probe (serial number), an amount of return light (return ratio), an optical path length, a numerical aperture (NA) offered by the optical element 117 (lens), a focal length, a (optical) resolution, an appropriate wavelength of light emanating from a light source, a noise level (a signal-to-noise ratio offered by the probe), and a diameter of a light spot.

Moreover, the data stored in the probe data unit 137 specifies, as shown in FIG. 30B and FIG. 30C, the conditions for driving the X scanner 114a and Y scanner 114b.

The conditions for driving the X scanner 114a include, as listed in FIG. 30B, a correction coefficient for an X positional phase ($\theta_X$), an X driving frequency ($V_X$), an X offset voltage ($V_{XO}$), an X field of view ($l_X$), a type of X driving waveform (type of driving waveform), an X image range ($P_X$), and an X scanning technique (X=. . . ; driving waveform). The conditions for driving the Y scanner 114b are, as listed in FIG. 30C, the same as the conditions for driving the X scanner 114a, though the letter X is changed to the letter Y.

When the optical probe 101 is freely detachably attached to the main body 130, the probe data unit 137 is connected to the control unit 135. The foregoing data is then read into the control unit 135 in response to a reading signal sent from the control unit 135.

Next, data stored in the probe data unit 137 will be detailed below.

The data stored in the probe data unit 137 is concerned with the optical characteristics of a scanning optical system including the optical element 117, photo-detector 134, and light source 133, such as, a diameter of a light spot and a resolution or an appropriate wavelength of light emanating from the light source.

A spatial resolution offered by the scanning optical system is determined with a (optical) resolution r, a scanning velocity, and a sampling rate. In order to effectively improve the (optical) resolution r, a constant set in the low-pass filter (LPF) included in the photo-detector 134 of the scanning optical system must be determined to satisfy each set of conditions.

If the passband of the filter included in the photo-detector 134 is made wide, many noises are contained in an image.

According to the present embodiment, the cutoff frequency of the low-pass filter is set to a value calculated as follows:

Cutoff frequency=0.441×maximum scanning velocity/resolution where the coefficient 0.441 is variable depending on the degree of weighting performed on an image.

Moreover, an amount of return light incident on the photo-detection element 134a varies depending on a difference in assembling of the components of the optical probe 101 or a difference in the design thereof. When unnecessary return light falls on the photo-detection element 134a, it is detected as a noise.

According to the present embodiment, in the optical probe 101, signal components whose levels are lower than the lowest level of noises that are derived from unnecessary return light will not be picked up to determine a resolution of data. Signal levels to be passed or cut off are determined with a range of signal levels which the A/D converter included in the frame grabber 136 can convert. The control unit 135 determines the foregoing settings and controls the photo-detector 134.

Moreover, the data stored in the probe data unit 137 is concerned with the conditions for driving the scanners; such as, an X positional phase correction coefficient ($\theta_X$) and an X driving frequency ($V_X$). By taking the X scanner 114 as an example, a description will proceed.

The X scanner 114a is driven at its resonant frequency so that it will be driven on a stable basis to oscillate with a large amplitude. The resonant frequency is determined with the mechanical structure of the scanner and the characteristics of a resonator, and may be varied in the course of assembling. The resonant frequency value is specified as the X driving frequency fx in the probe data. Likewise, the field of view in an X scanning direction is specified as the X field of view lx.

In order to effectively utilize the (optical) resolution r of the optical system for display of an image, the number of display pixels (number of columns of interpolated data items) L should be equal to or larger than the value calculated as follows:

$$L = lx/d \times 2$$

According to the present embodiment, the frame grabber 136 is designed so that the above value will be attained in the center of an angle of imaging view and a space between sampling points in the frame grabber will be the longest at the sampling positions near the center of an image.

Assuming that the X scanner 114a is driven with a sine waveform, when the scanner oscillates with the maximum amplitude, the scanning velocity becomes approximately 0. If the frame grabber 136 samples stored data at this time, the number of sampling points gets too large for a display image range. This makes it necessary to greatly increase the size of the image memory included in the grabber, and is therefore not cost-efficient.

According to the present embodiment, therefore, a range of data to be sampled in the frame grabber 136 is limited to the center of the frame grabber and its surroundings (up to 92.5%). Consequently, an unnecessarily large amount of data will not be acquired but sampling can be achieved efficiently. The sampled range is stored as the X image range Px in the probe data unit 137.

The scanning velocity $V_{XMAX}$ attained in the center of the angle of imaging view is provided as follows:

$$V_{XMAX} = \pi \times lx/(Px \times fx) \tag{1}$$

The sampling frequency is provided as follows:

$$fs = V_{XMAX}/d \times 2 \tag{2}$$

The sampling frequency fs shall be adopted as the clock frequency at which the signal generator 131 operates.

Consequently, the number of sampling points per line M is provided as follows:

$$M = (fs/(2 \times fx)) \times \sin^{-1}(2\pi \cdot Px) \tag{3}$$

Moreover, the number of clock pulses required for each cycle, Nxc, is provided as follows:

$$Nxc = fs/fx \tag{4}$$

The signal generator 131 is constituted so as to produce a waveform, which is designated as a type of X driving waveform, so that the waveform will alternate in response to the clock pulses.

The waveform is expressed as follows:

$$Xscan(N) = (2\pi \times n/Nxc + \theta x) \tag{5}$$

where n denotes 0, 1, 2, etc., or Nxc−1.

Herein, as shown in FIG. 31, an Xscan(N) data string 141 is read by the X driving terminal (X-Drive) 130a of the signal generator 131 into a reading buffer 142 in response to each clock pulse. Then, a D/A converter 143 performs a digital-to-analog (D/A) conversion for the read column of data. The resultant data is then outputted. Moreover, an offset controller 144 and an amplifier 132a of the X driving terminal 130a control a gain represented by an X driving voltage Vx and an offset represented by an X offset voltage Vxo respectively. Consequently, a driving voltage is transmitted to the X scanner 114a through the X driving terminal 130a.

Moreover, the signal generator 131 provides a produced x triggering signal (X-Sync) at the timing deviated by the duration of a subsequent clock pulse from a reference point of a driving waveform (a point at which the amplitude of the driving waveform becomes maximum).

The X triggering point Ntx is provided as follows:

$$Ntx = [(Nxc/2) \times (1 - Px/100)]/2 \tag{6}$$
$$= [Nxc/2] - M/2$$

The signal generator 131 is constructed so as to provide the X triggering signal at the timing of the X triggering point Ntx. The X triggering signal (X-Sync) may be provided by the number of lines on which data is acquired after the production of the Y triggering signal (Y-Sync).

The settings of the Y scanner 114b are determined basically in the same manner as the settings of the X scanner 114a. The settings of the Y scanner 114b, that is, the number of sampling points M, the number of sampling lines N, and the clock frequency fs are provided by reading fx=fy in the foregoing expressions.

The control unit 135 performs the aforesaid calculations, that is, solves the aforesaid expressions. Calculated are the number of columns of interpolated data L, the number of rows of interpolated data W, the number of sampling points per line M, the number of sampling lines N, the clock frequency fs, the numbers of clock pulses required per cycle Nxc and Nyc, the waveforms Xscan and Yscan, the X and Y triggering points Ntx and Nty, the start position of the X scanner 114a in an X direction $t_{XO}$, and the start position of the Y scanner 114b in a Y direction $t_{YO}$.

The calculated values are inputted to the signal generator 131 and set therein. Consequently, the components can be driven according to the timings shown in the timing chart to be described below.

The calculated values are also outputted to the frame grabber 136 and image engine 139 and used for sampling and interpolation.

Data required by the image engine 139 are the above-mentioned L, M, W, N, $t_{XO}$, $t_{YO}$ and the formulas of driving waveforms used to drive the X scanner 114a and Y scanner 114b respectively.

The formulas of driving waveforms are as follows:

$$X=\cos(t) \quad (7a)$$

$$Y=\cos(t) \quad (7b)$$

where t denotes a positional phase.

$$t_{XO}=(\pi/Nxc)\times(Nxc/2-M) \quad (8a)$$

$$t_{YO}=(\pi/Nyc)\times(Nyc/2-N) \quad (8b)$$

The image engine 139 produces a transformation table on the basis of the foregoing data, and interpolates image data items to rearrange the data items as mentioned previously.

Next, interpolation to be performed by the image engine 139 will be described below.

The image engine 139 interpolates image data items, which represent one frame and are temporarily stored in the memory 138, according to, for example, the nearest neighbor interpolation technique or the like, and thus rearranges the data items. Consequently, the positions of dots constituting an image coincide with the positions of sampling points.

Herein, interpolation is a kind of processing used to deform or enlarge an image by producing new dots among dots constituting a raw image. The interpolation technique includes, aside from the nearest neighbor interpolation, the bi-linear interpolation and the cubic convolution interpolation.

The nearest neighbor interpolation is an interpolation technique of adopting a color value exhibited by a dot located nearest to an interpolation dot as a color value of the interpolation dot. The bi-linear interpolation is an interpolation technique of adopting an average of color values, which are exhibited by four dots located around an interpolation point, as a color value of the interpolation dot. The cubic convolution interpolation is an interpolation technique of interpolating sixteen dots located around the interpolation dot according to the cubic spline technique and adopting the result of interpolation as a color value of the interpolation dot.

According to the present embodiment, the bi-linear interpolation is adopted for interpolation.

When the bi-linear interpolation is adopted, an average of color values of four dots $u_{Ai,Bj}$, which are contained in an original image and located nearest to an interpolation dot $v_{ij}$, is adopted as a color value of the interpolation dot $v_{ij}$ as shown in FIG. 32.

Consequently, the color value of the interpolation dot or new dot $v_{ij}$ is calculated according to expression (11). where i=1, 2, 3, . . . , L, and j=1, 2, 3, . . . , or W.

$$v_{ij}=K_{yi}[K_{xj}\times u_{Ai,Bj}+(1-K_{xj})\times u_{Ai,Bj+1}]+(1-K_{yi})[K_{xj}\times u_{Ai+1,Bj}+(1-K_{xj})\times u_{Ai+1,Bj+1}] \quad (11)$$

In order to calculate the value of one interpolation dot $v_{ij}$ using the expression (11), the requirements described below must be attained first.

(1) The four raw image component dots nearest to the interpolation dot $v_{ij}$ must include the left upper dot $u_{Ai,Bj}$ in FIG. 32 that expresses data Ai,Bj on a data column.

(2) The interpolation coefficients $K_{xj}$ and $K_{yio}$ for the X- and Y-direction values of the upper left dot $u_{Ai,Bj}$ in FIG. 32 must be determined.

Next, a procedure of calculating the value of the interpolation dot $v_{ij}$ will be described below.

As mentioned above, both the X scanner 114a and Y scanner 114b are driven with sine waveforms. Assume that L denotes the number of columns of interpolated data, W denotes the number of rows of interpolated data, $t_{xo}$ denotes the positional phase of the X scanner 114a at the start position thereof, and $t_{YO}$ denotes the positional phase of the Y scanner 114b at the start position thereof.

Moreover, $X_0$ denotes the start position in an X direction of the X scanner 114a, $Y_0$ denotes the start position in a Y direction of the Y scanner 114b, $\Delta X_v$ denotes a positional interval in the X direction between interpolated data items, and $\Delta Y_v$ denotes a positional interval in the Y direction between interpolated data items.

The position in the X direction of the X scanner 114a, the position in the Y direction of the Y scanner 114b, the positions of interpolated data items scanned by the X scanner 114a and Y scanner 114b are expressed as the formulas (12) below.

First, the relationship between the data column number Bj $$f(t)=\cos(t) \quad (12a)$$

$$Xv(t)=\cos(t_{xv}) \quad (12b)$$

$$Yv(t)=\cos(t_{yu}) \quad (12c)$$

on which data expressed as the left upper dot $u_{Ai,Bj}$ is present and the interpolation coefficient $Kx_j$ for the X-direction value will be sought.

As shown in FIG. 33, the position in the X direction (on a column) of the interpolation dot $v_{ij}$ is calculated as follows:

$$X_v=X_0-\Delta X_v(j-1) \quad (13)$$

Moreover, the positional phase $t_{xv}$ in the X direction of the dot $v_{ij}$ is provided as follows:

$$t_{Xv}=\arccos(X_v) \quad (14)$$

A positional phase amount $\Delta t_x$ occurring during a data sampling time $\Delta t$ is expressed as follows:

$$\Delta t_x=(\pi-2t_{x0})/(M-1) \quad (15)$$

The data column number Bj is expressed as follows:
The position $X_u$ in the X direction of the dot $u_{Ai,Bj}$, and $$Bj=int[(t_{Xv}-t_{X0})/\Delta t_X]+1 \quad (16)$$

the position $X_{u+1}$ in the X direction of the dot $u_{Ai,Bj+1}$, are expressed as follows:

$$X_u=\cos[(Bj-1)\Delta t_X+t_{X0}] \quad (17a)$$

$$X_{u+1}=\cos[(Bj)\Delta t_X+t_{X0}] \quad (17b)$$

The interpolation coefficient $Kx_j$ for the X-direction value of the interpolation dot $v_{ij}$ that is applied to the value of the dot $u_{Ai,Bj}$ is expressed as follows:

$$Kx_j=|(X_{u+1}-Xv)/(X_{u+1}-X_u)| \quad (18)$$

Next, the relationship between the data column number Ai on which data expressed as the upper left dot $u_{Ai,Bj}$ is present and the interpolation coefficient $Ky_j$ for the Y-direction value of the interpolation dot $v_{ij}$ will be sought.

As shown in FIG. 34, the position $Y_\upsilon$ in the Y direction of the interpolation dot $v_{ij}$ is calculated as follows:

$$Y\upsilon = Y_0 - \Delta Y_\upsilon(i-1) \qquad (18)'$$

The positional phase $t_{Y\upsilon}$ in the Y direction of the dot $v_{ij}$ is provided as follows:

$$t_{Y\upsilon} = \arccos(Y_\upsilon) \qquad (19)$$

A positional phase amount $\Delta t_Y$ occurring in the Y direction during a data sampling time $\Delta t_y$ is calculated as follows:

$$\Delta t_Y = (\pi - 2t_{Y0})/(N-1) \qquad (20)$$

Consequently, the data column number Ai is expressed as follows:

$$Ai = int[(t_{Y\upsilon} - t_{Y0})/\Delta t_Y] + 1 \qquad (21)$$

The position $Y_u$ in the Y direction of the dot $u_{Ai,Bj}$ and the position $Y_{u+1}$ in the Y direction of a dot $u_{Ai+1,Bj}$ are expressed as follows:

$$Y_u = \cos[(Ai-1)\Delta t_Y + t_{Y0}] \qquad (22a)$$

$$Y_{u+1} = \cos[(Ai\Delta t_Y + t_{Y0}] \qquad (22b)$$

The interpolation coefficient $Ky_j$ for the Y-direction value of the dot $v_{ij}$ that is applied to the value of the dot $$Kyi = |(Y_{u+1} - Y\upsilon)/(Y_{u+1} - Y_u)| \qquad (23)$$

$u_{Ai, Bj}$ is expressed as follows:
Consequently,

1. Four dots around an interpolation dot are determined by where j denotes 1, 2, etc., or L. Moreover, $t_{X\upsilon} = \arccos(X\upsilon)$, $$Bj = int[(t_{X\upsilon} - t_{X0})/\Delta t_X] + 1 \qquad (16)$$

$X\upsilon = X0 - \Delta X_\upsilon(j-1)$, and $\Delta t_X = (\pi - 2t_{X0})/(M-1)$.

$$Ai = int[(t_{Y\upsilon} - t_{Y0})/\Delta t_Y] + 1 \qquad (21)$$

where i denotes 1, 2, etc., or W. Moreover, $t_{Y\upsilon} = \arccos(Y\upsilon)$, $Y\upsilon = Y_0 - \Delta Y_\upsilon(i-1)$, and $\Delta t_Y = (\pi - 2t_{Y0})/(N-1)$.

2. Interpolation coefficients $Kx_j$ and $Kyi$ are determined . . .

$$Kx_j = |(X_{u+1} - X\upsilon)/(X_{u+1} - X_u)| \qquad (18)$$

where j denotes 1, 2, etc. or L. Moreover, $X_u = \cos[(Bj-1)\Delta t_X + t_{X0}]$, and $X_{u+1} = \cos[(Bj\Delta t_x + t_{X0})$.

$$Kyi = |(Y_{u+1} - Y\upsilon)/(Y_{u+1} - Y_u)| \qquad (23)$$

where i denotes 1, 2, etc., or W. Moreover, $Y_u = \cos[(Ai-1)\Delta t_Y + t_{Y0}]$, and $Y_{u+1} = \cos[(Ai\Delta t_Y + t_{Y0}]$.

Consequently, the interpolation dot $v_{ij}$ is expressed as follows:

$$V_{ij} = Ky_i[Kx_j \times u_{Ai,Bj} + (1-Kx_j) \times u_{Ai,Bj+1}] + (1-Ky_i)[Kx_j \times u_{Ai+1,Bj} + (1-Kx_j) \times u_{Ai+1,Bj+1}] \qquad (24)$$

where i denotes 1, 2, etc., or L and j denotes 1, 2, etc., or W.

Based on the calculated values, the image engine 139 interpolates image data items according to the bi-linear interpolation. The image engine 139 thus rearranges the image data items, which are sampled at unequal spatial intervals as shown in FIG. 35A, in the form shown in FIG. 35B or FIG. 35C. Thereafter, the image engine 139 performs STC processing such as attenuation correction.

Concerning with the interpolation, in an odd frame, image data items sampled at unequal spatial intervals are, as shown in FIG. 35B, interpolated according to the bi-linear interpolation. In an even frame, after interpolation is performed in the same manner as when an odd frame is dealt with, aliasing is performed as shown in FIG. 35C.

In the optical imaging system 100 having the aforesaid configuration, the direct-vision optical probe 101 is freely detachably attached to the main body 130 and can be replaced with another. The optical imaging system 100 irradiates measurement light beam, which emanates from the light source, to an object, and constructs an observed image, which renders the inside of the object, from the information of return light.

At this time, the optical imaging system 100 has the probe data unit 137, which is included in the optical probe 101, connected to the control unit 135. Data in the probe data unit 137 is read into the control unit 135. The control unit 135 performs necessary calculations on the read data, and drives and controls the components of the optical imaging system. Thus, the control unit 135 extends control depending on the connected optical probe 101.

In the optical imaging system 100, the signal generator 131 produces signals according to the timings shown in any of FIG. 36 to FIGS. 42A–42G under the control of the control unit 135. Thus, the X scanner 114a and Y scanner 114b included in the optical probe 101 are controlled and driven.

FIGS. 36A–36E include a timing chart indicating the timings of signals produced by the signal generator 131 in a steady state.

FIG. 36A is a graph showing the waveform of a Y driving signal that is a driving signal with which the Y scanner 114b is driven. The Y driving signal is generated based on the aforesaid waveform data Yscan(N). With output of the Y driving signal, the Y scanner 114b is driven with a sine waveform. Incidentally, one cycle of the Y driving signal corresponds to the sum of the durations of Nyc clock pulses.

FIG. 36B is a graph showing the waveform of an on/off (Y-U/D) signal. The on/off (Y-U/D) signal assumes an on (Up)state level to indicate that the Y scanner 114b driven with the Y driving signal shown in FIG. 36A scans data representing an odd frame or assumes an off (Down)-state level to indicate that the Y scanner 114b scans data representing an even frame. In other words, the Y-U/D signal is driven to the on-state level (driven high) when the Y scanner 114b scans data representing an odd frame, subjected to aliasing, and then driven to the off-state level (driven low) when the Y scanner 114b scans data representing an even frame.

Synchronously with the Y driving signal used to drive the Y scanner 114b, the X scanner 114a is, as shown in FIG. 36C to FIG. 36E, driven with a sine waveform whose cycle corresponds to a time interval A to F indicated in FIG. 36.

Image data acquired by driving the X scanner 114a and Y scanner 114b is sampled synchronously with the driving signals, which are used to drive the scanners, within the frame grabber 136. The Y triggering signal (Y-Sync) and X triggering signal (X-Sync) that initiate the sampling, and a signal having the clock frequency fs are outputted according to the timings shown in FIG. 36C to FIG. 36E.

The Y triggering signal (Y-Sync) shown in FIG. 36C is outputted at the timing deviated by the duration of the next clock pulse Nty from the timing of the Y driving signal assuming the highest level. Likewise, the X triggering signal (X-Sync) shown in FIG. 36D is outputted at the timing deviated by the duration of the next clock pulse Ntx from the timing of the X driving signal assuming the highest level.

Data representing one frame is sampled during a period from outputting of the Y triggering signal (Y-Sync) to the next outputting such that the number of sampling lines will be N. The signal having the clock frequency fs shown in FIG. 36E is constituted of successive clock pulses, and is synchronized with the X driving positional phase nπ (where n denotes 0, ±1, ±2, etc.). The signal having the clock frequency fs need not be synchronized with the X driving positional phase of π/2+nπ (n denotes 0, ±1, ±2, etc.).

Next, the timings of the signals will be detailed in conjunction with FIGS. 37A–37E to FIGS. 42A–42G that show the waveforms of the signals attained during the period from time instant A to time instant F indicated in FIG. 36.

FIGS. 37A–37G include a timing chart indicating the timings of signals outputted when the Y driving signal assumes the maximum positive level. FIGS. 38A–38E include a timing chart indicating the timings of the signals outputted when the Y triggering signal (Y-Sync) is outputted in order to initiate scanning of data representing a first frame (an outward sweep). FIGS. 39A–39E include a timing chart indicating the timings of the signals outputted immediately before sampling of data representing one frame is completed. FIGS. 40A–40G include a timing chart indicating the timings of the signals outputted when the Y driving signal assumes the maximum negative level. FIGS. 41A–41G include a timing chart indicating the timings of the signals transmitted when the Y triggering signal (Y-Sync) is outputted in order to initiate scanning of data representing the second frame (a homeward sweep). FIGS. 42A–42G include a timing chart indicating the timings of the signals outputted immediately before sampling of data representing the second frame is completed.

FIG. 37A to FIG. 42A show the waveforms of the Y driving signal. FIG. 37B to FIG. 42B show the waveforms of the Y-U/D signal. FIG. 37C to FIG. 42C show the waveforms of the Y triggering signal (Y-Sync). FIG. 37D to FIG. 42D show the waveforms of the X triggering signal (X-Sync). FIG. 37E to FIG. 42E show the waveforms of the signal having the clock frequency fs.

FIG. 37F to FIG. 42F are graphs showing the waveforms of the X driving signal that is a driving signal used to drive the X scanner 114a. The X driving signal is generated based on the aforesaid waveform data Xscan(N). With generation of the X driving signal, the X scanner 114a is driven with a sine waveform. One cycle of the X driving signal corresponds to the sum of the durations of Nxc clock pulses. FIG. 37G to FIG. 42G are graphs showing angles at which the optical element 117 scanned by the X scanner 114a is driven in an X direction.

When the Y driving signal assumes the maximum positive level, the Y-U/D signal is driven to the on-state level. Since the amplitude with which the Y scanner 114b oscillates falls outside an observable range, neither the Y triggering signal (Y-Sync) nor the X triggering signal (X-Sync) is outputted. In other words, a period from the instant the Y driving signal assumes the maximum positive level to the instant the Y triggering signal (Y-Sync) is outputted is a pause period.

The Y-U/D signal is driven to the on-state level, and Nty clock pulses are transmitted. Thereafter, the Y driving signal assumes a level causing the amplitude with which the Y scanner 114b oscillates to fall within the observable range, the Y triggering signal (Y-Sync) is outputted. Synchronously with the Y triggering signal (Y-Sync), Ntx clock pulses are transmitted and the X triggering signal (X-Sync) is then outputted.

The signal generator 131 outputs a signal to the frame grabber 136 so that data on the first to N-th lines representing the first (1) frame will be sampled within an effective data domain, which is defined with the sampling rate of M sampling points per line, until the Y driving signal approaches to the maximum negative level and the amplitude with which the Y scanner 114b oscillates falls outside the observable range. When the Y driving signal approaches to the maximum negative level and the amplitude of the Y scanner 114b falls outside the observable range, the X triggering signal (X-Sync) is not outputted any more. The pause period starts.

When the Y driving signal assumes the maximum negative level and the Y scanner 114b makes a turn to scan data representing an even frame, similar to when the Y driving signal assumes the maximum positive value, neither the Y triggering signal (Y-Sync) nor X triggering signal (X-Sync) is outputted. The pause period lasts from the instant the Y driving signal assumes the maximum negative value to the instant the Y triggering signal (Y-Sync) is transmitted.

After the Y-U/D signal is driven to the on-state level and Nty clock pulses are outputted, the Y driving signal assumes a level causing the amplitude of the Y scanner 114b to fall within the observable range. Consequently, the Y triggering signal (Y-Sync) is outputted. The X triggering signal (X-Sync) is outputted synchronously with the Y triggering signal (Y-Sync). Outputting of the X triggering signal (X-Sync) does not lag behind outputting of the Y triggering signal (Y-Sync) by the sum of the durations of Ntx clock pulses but lags behind the outputting by a half-waveform length.

The foregoing control sequence can nullify the difference between the sampling points regarding an odd frame and the sampling points regarding an even frame.

The signal generator 131 transmits a signal to the frame grabber 136 so that data on the first to N-th line representing the second frame (2) will be sampled within the effective data domain, which is defined with the sampling rate of M sampling points per line, until the Y driving signal approaches to the maximum positive level and the amplitude of the Y scanner 114b falls outside the observable range.

When the Y driving signal approaches to the maximum positive value and the amplitude of the Y scanner 114b falls outside the observable range, the X triggering signal (X-Sync) is not outputted any more. The pause period starts. Thereafter, the aforesaid actions are repeated.

As mentioned above, when the X scanner 114a and Y scanner 114b are driven, image data picked up by the optical element 114 is sampled and arranged as shown with dots in FIG. 35A. The image engine 139 interpolates the image data as mentioned above in conjunction with FIG. 35A to FIG. 35C, and then outputs the resultant data to the image processor 140. The image processor 140 performs signal processing such as display and transfer, and outputs the resultant signal to the monitor. Consequently, an observed image (image produced by optical imaging) is displayed on the display surface of the monitor.

Consequently, the optical imaging system 100 of the present embodiment can produce an ideal image devoid of a distortion. Moreover, the optical imaging system 100 of the present embodiment can operate on a stable basis because actions are all performed synchronously.

The optical imaging system 100 of the present embodiment has been described on the assumption that a display scanner is included for scanning the optical element 117 in X and Y directions. A three-dimensional display scanner that includes, in addition to the X and Y scanners, a Z scanner for scanning the optical element in Z directions (optical-axis directions) may be adopted. It goes without saying that the present embodiment can implement the three-dimensional scanner in the same manner with the two-dimensional scanner.

Moreover, in the optical imaging system 100 of the present embodiment, if restrictions are imposed on pixels of an image displayed on the monitor or the like, the conditions for scanning and sampling may be calculated based on the L value (number of columns of interpolated data items) and the W value (number of rows of interpolated data items).

If an optical imaging system is designed to be able to set the clock frequency fs to any of finely determined values, the optical imaging system becomes expensive. Therefore, the clock frequency fs may be set to a value closest to the value calculated according to the expression (1), and the subsequent calculations may be carried out.

Moreover, an optical imaging system may have the Nxc and Nyc values predetermined. The clock frequency fs may then be determined based on the relationship thereof to the Nxc value. In this case, the signal generator 131 in the optical imaging system can be simplified.

According to the timing charts referred to in relation to the first embodiment, the X scanner 114a and Y scanner 114b are driven with a distinct sine waveform. Depending on the characteristics of the scanners, the scanners may be, as shown in FIG. 43, driven at a driving frequency at which the scanners do not oscillate ideally and image signals scanned by the scanners contain a distortion.

In this case, in the optical imaging system 100, the scanning characteristics of the scanners are recorded in the form of approximate expressions in the probe data unit 137.

For example, the approximate expressions are fifth-order approximate expressions.

$$X = a_1 t^5 + a_2 t^4 + a_3 t^3 + a_4 t^1 + a_5 t^6 \quad (25a)$$

$$Y = b_1 t^5 + b_2 t^4 + b_3 t^3 + b_4 t^1 + b_5 t^6 \quad (25b)$$

where X denotes the direction of a field of view, t denotes a positional phase attained within a scanning cycle, and $a_1$ to $a_6$ denote approximation coefficients.

In the optical imaging system 100, the interpolation expressions are replaced with the approximate expressions. This enables calculation of the interpolation coefficients.

Consequently, according to the present variant, even when the scanners move in such a manner that scanning is not performed ideally but data containing a distortion is acquired, an image devoid of a distortion can be produced.

Moreover, in the optical imaging system 100, the X scanner 114a is driven with a sine waveform and scans data by performing a one-way sweep. Alternatively, the X scanner 114a may scan data by performing two sweeps of outward and homeward during one cycle of the sine waveform.

In this case, the optical imaging system 100 should merely generate two X triggering signals (X-Sync) (that are out of positional phase with each other by $\pi$) during one cycle of an X driving signal.

In the optical imaging system 100, the control unit 135 solves a determinant presented below, and the frame grabber 136 rearranges in advance even rows of data to be scanned.

The resultant data is then outputted to the image engine 139.

$$\begin{pmatrix} N'_{21} \\ N'_{22} \\ N'_{23} \\ \vdots \\ N'_{2M} \end{pmatrix} = \begin{pmatrix} 0,0,0, & \cdots & 0,0,1 \\ 0,0,0, & \cdots & 0,1,0 \\ 0,0,0, & \cdots & 1,0,0 \\ \vdots & \ddots & \vdots \\ 1,0,0, & \cdots & 0,0,0 \end{pmatrix} \begin{pmatrix} N_{21} \\ N_{22} \\ N_{23} \\ \vdots \\ N_{2M} \end{pmatrix} \quad (26)$$

where $N_{21}$, etc., and $N_{2M}$ denotes the second row of input data values, $N'_{21}$, etc., and $N'_{2M}$ denote transformed data values. M denotes the number of sampling points per line.

Consequently, according to the present embodiment, the time during which sampling can be made longer than the time during which data is scanned. This results in fast scanning.

FIFTH EMBODIMENT

Figure 44:
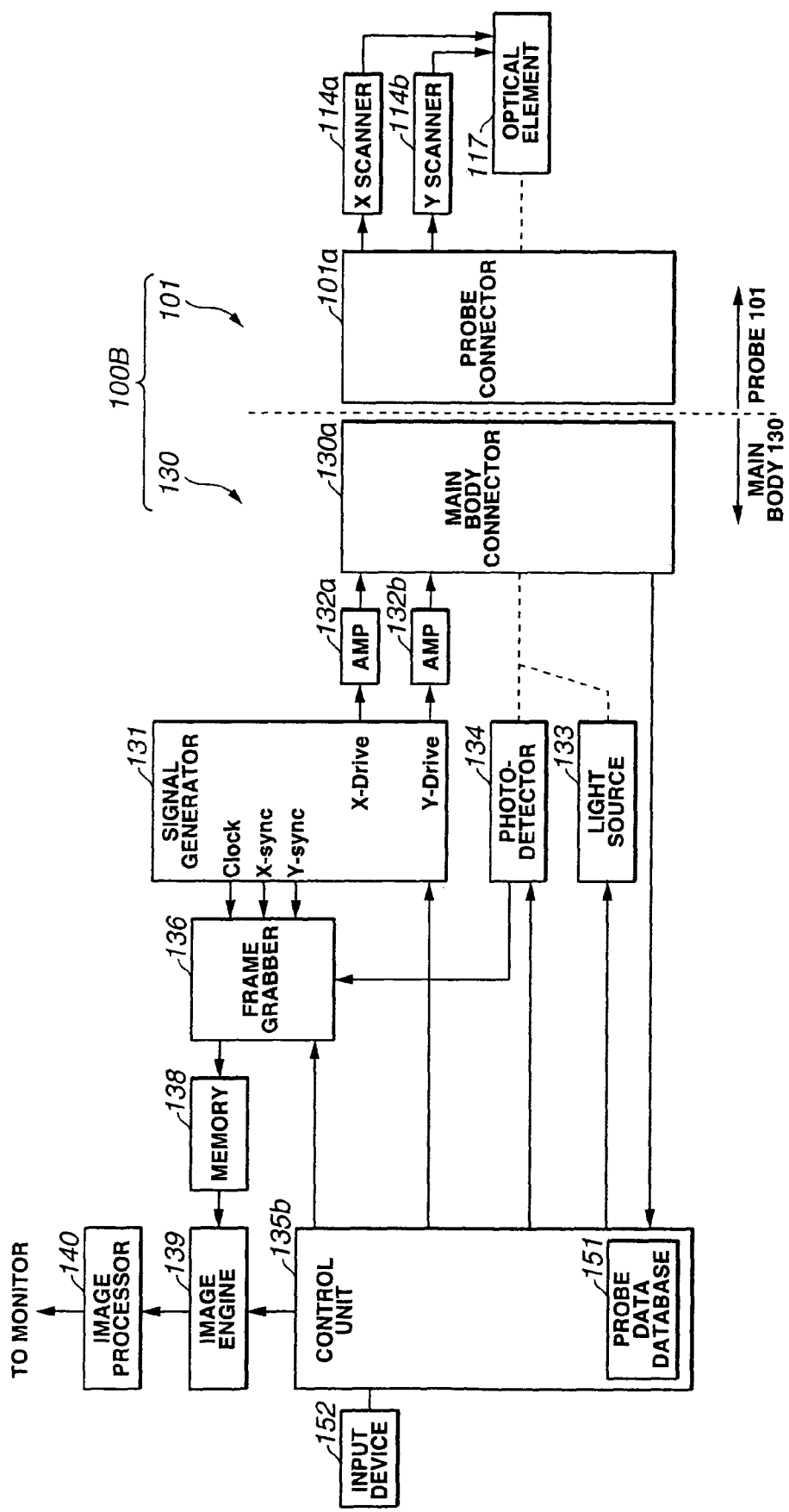
FIG. 44 is a circuit block diagram schematically showing the configuration of an optical imaging system in accordance with a fifth embodiment.
Figure 45:
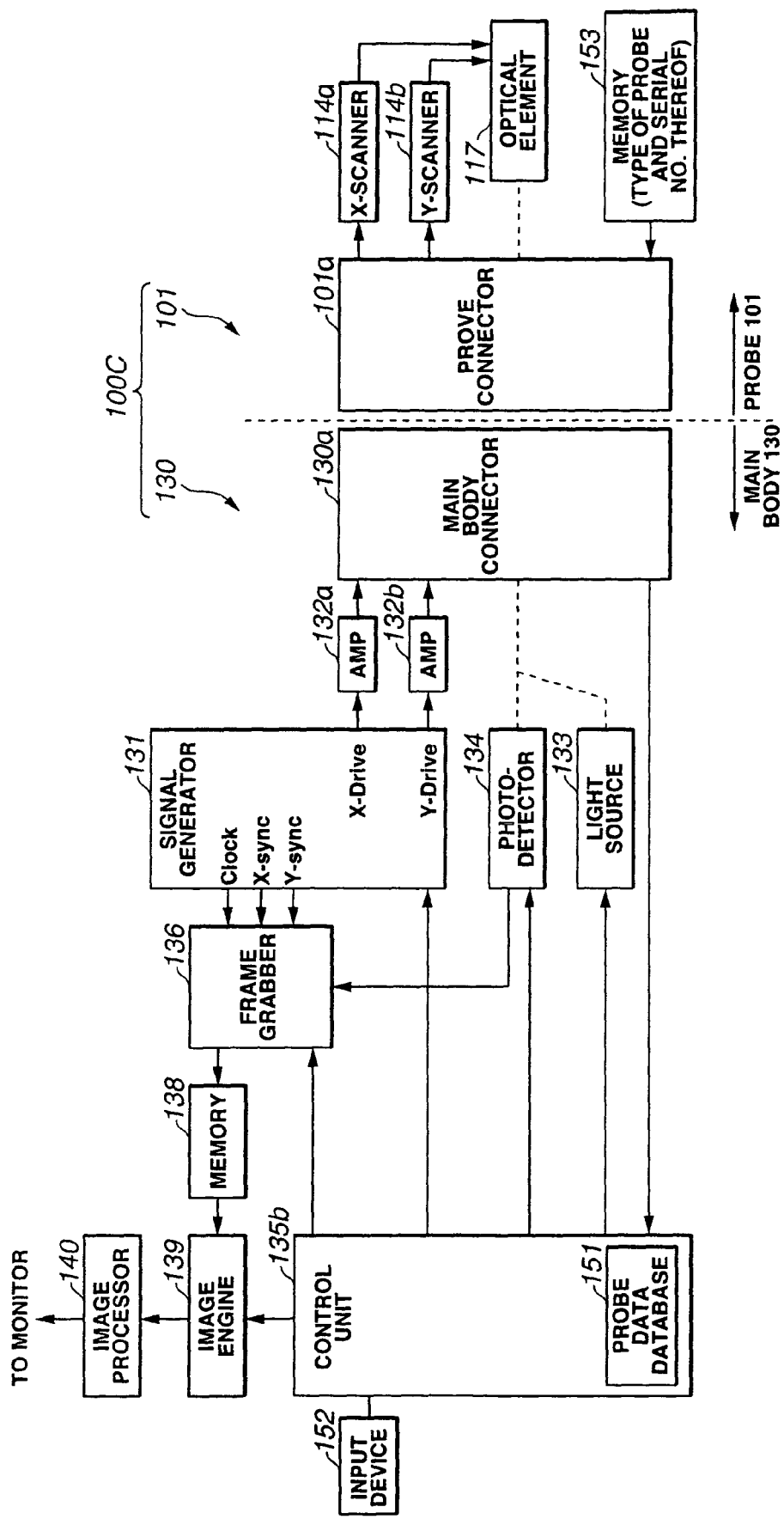
FIG. 45 is a circuit block diagram showing a variant of the optical imaging system shown in FIG. 44.

FIG. 44 and FIG. 45 are concerned with a fifth embodiment of the present invention. FIG. 44 is a circuit block diagram schematically showing the configuration of an optical imaging system in accordance with the fifth embodiment. FIG. 45 is a circuit block diagram showing a variant of the optical imaging system shown in FIG. 44.

According to the fourth embodiment, the optical probe 101 includes the probe data unit in which inherent data is held. According to the fifth embodiment, data concerning probes employed is held in the control unit 135. The other characteristics are identical to those of the fourth embodiment, and the description thereof will therefore be omitted. The components identical to those of the fourth embodiment will be described with the same reference numerals assigned thereto.

Specifically, as shown in FIG. 44, an optical imaging system 100B of the fifth embodiment has a probe data database 151, which is constituted of a nonvolatile memory such as a hard disk drive (HDD), included in a control unit 135b. The probe data database 151 receives data concerning optical probes employed and saves it. When an input device 152 such as a keyboard is used to enter a numerical value, the data concerning the optical probe 101 is saved. Incidentally, data may be copied from any other storage means such as a floppy disk into the probe data database 151.

In the optical imaging system 100B having the above components, an operator handles the input device 152 based on the attached optical probe 101. Thus, data of a desired probe is read from the probe data database 151. The control unit 135 then outputs set values to the image engine 139, signal generator 131, and frame grabber 136 in the same manner as it is in the fourth embodiment, and thus establishes an observable state.

Thereafter, the operator operates the optical imaging system 100B to start scanning and observation.

Similarly to the fourth embodiment, the optical imaging system 100B operates to produce an image devoid of a distortion.

Consequently, in the optical imaging system 100B of the fifth embodiment, even when the optical probe 101 includes no memory, optimal conditions for driving can be easily designated.

The optical imaging system may have the configuration shown in FIG. 45.

As shown in FIG. 45, an optical imaging system 100C has a memory 153, in which a type of probe and a serial number thereof are recorded, included in an optical probe 101C.

In the optical imaging system 100C having the foregoing components, when the optical probe 101C is attached to the main body, the control unit 135 reads the type of probe and serial number thereof from the memory 153 included in the optical probe 101. Thereafter, the control unit 135 selects setting information concerning the probe from the probe data database 151, and calculates set values to be set in the image engine 139, frame grabber 136, signal generator 131, and photo-detector 134. The calculated set values are outputted, and the conditions for operation are designated. Thereafter, the operator operates the optical imaging system 100C to start scanning and observation.

Consequently, in the optical imaging system 100C of the present variant, the memory included in the optical probe is small in size. Nevertheless, automatic designation is achieved. This leads to improved maneuverability.

SIXTH EMBODIMENT

Figure 46:
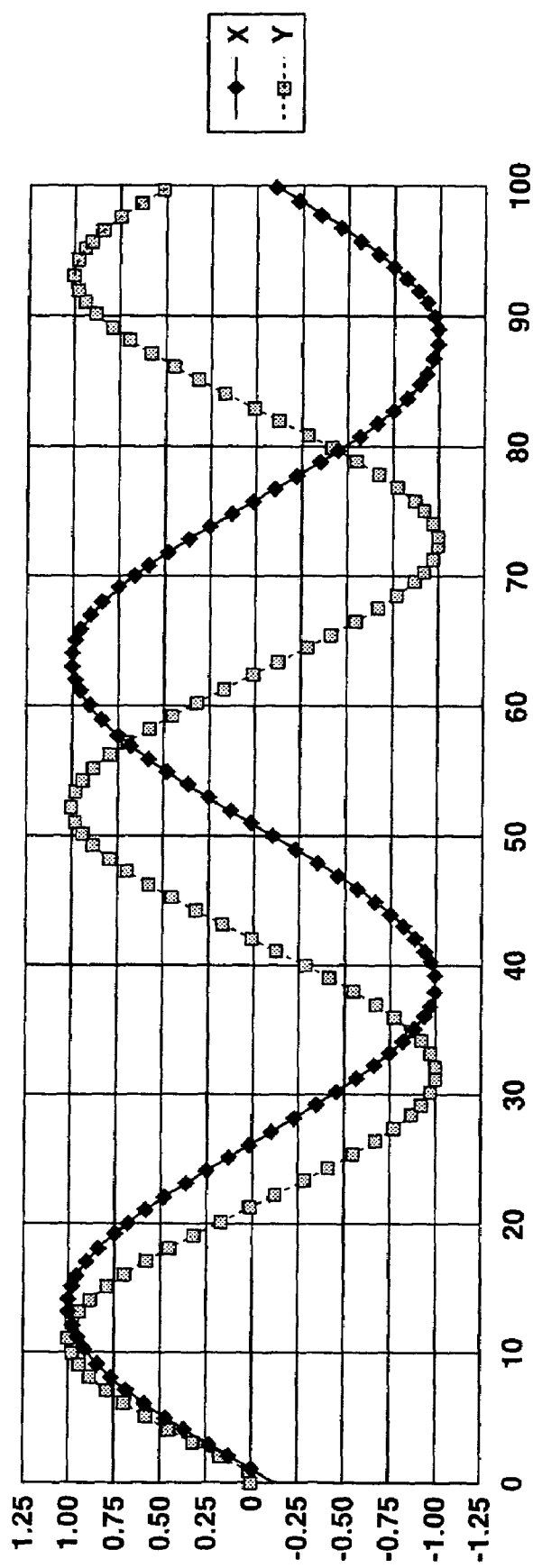
FIG. 46 is a graph showing the waveforms of driving signals with which an X scanner and a Y scanner are driven at nearly the same resonance frequencies.
Figure 47:
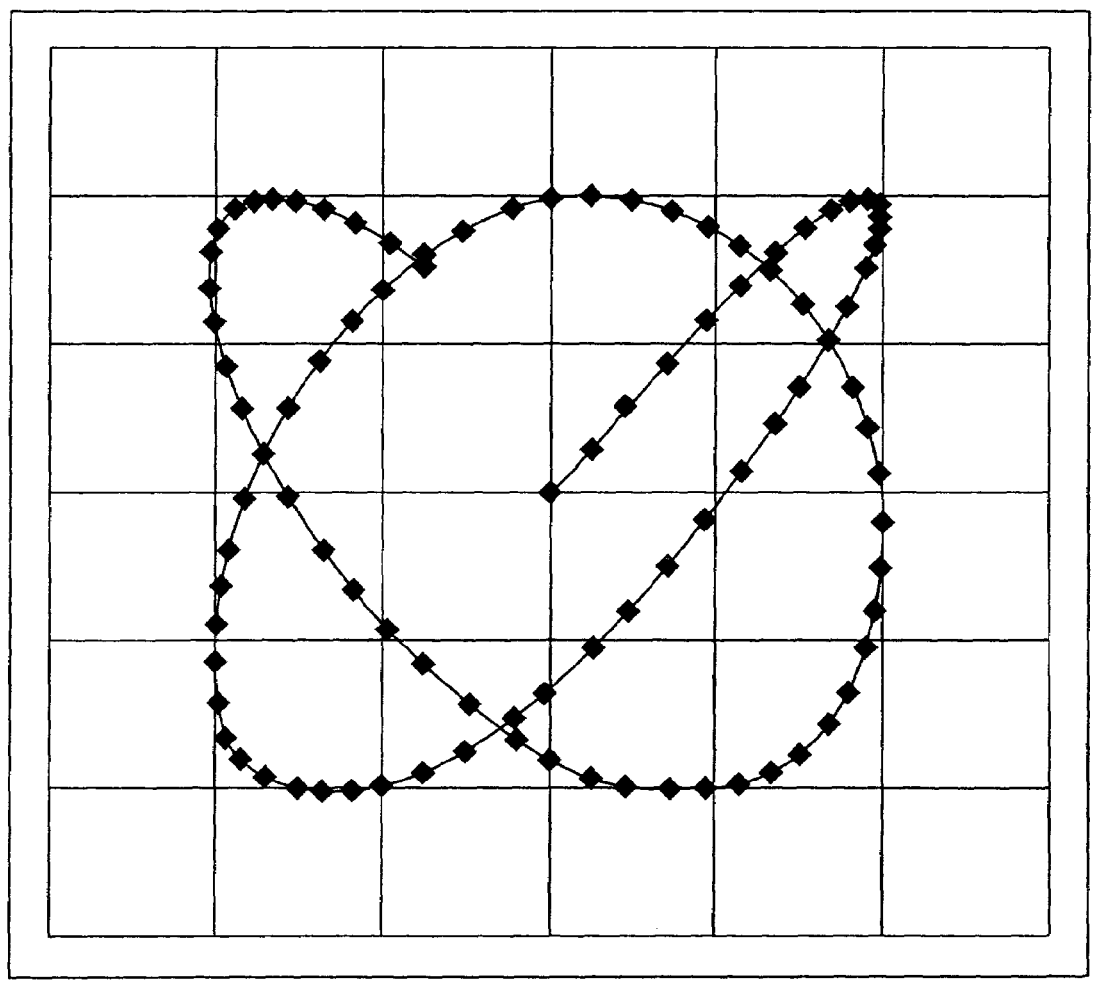
FIG. 47 is a graph showing scanning patterns to be traced by the X and Y scanners that are driven with the driving signals shown in FIG. 46.
Figure 48:
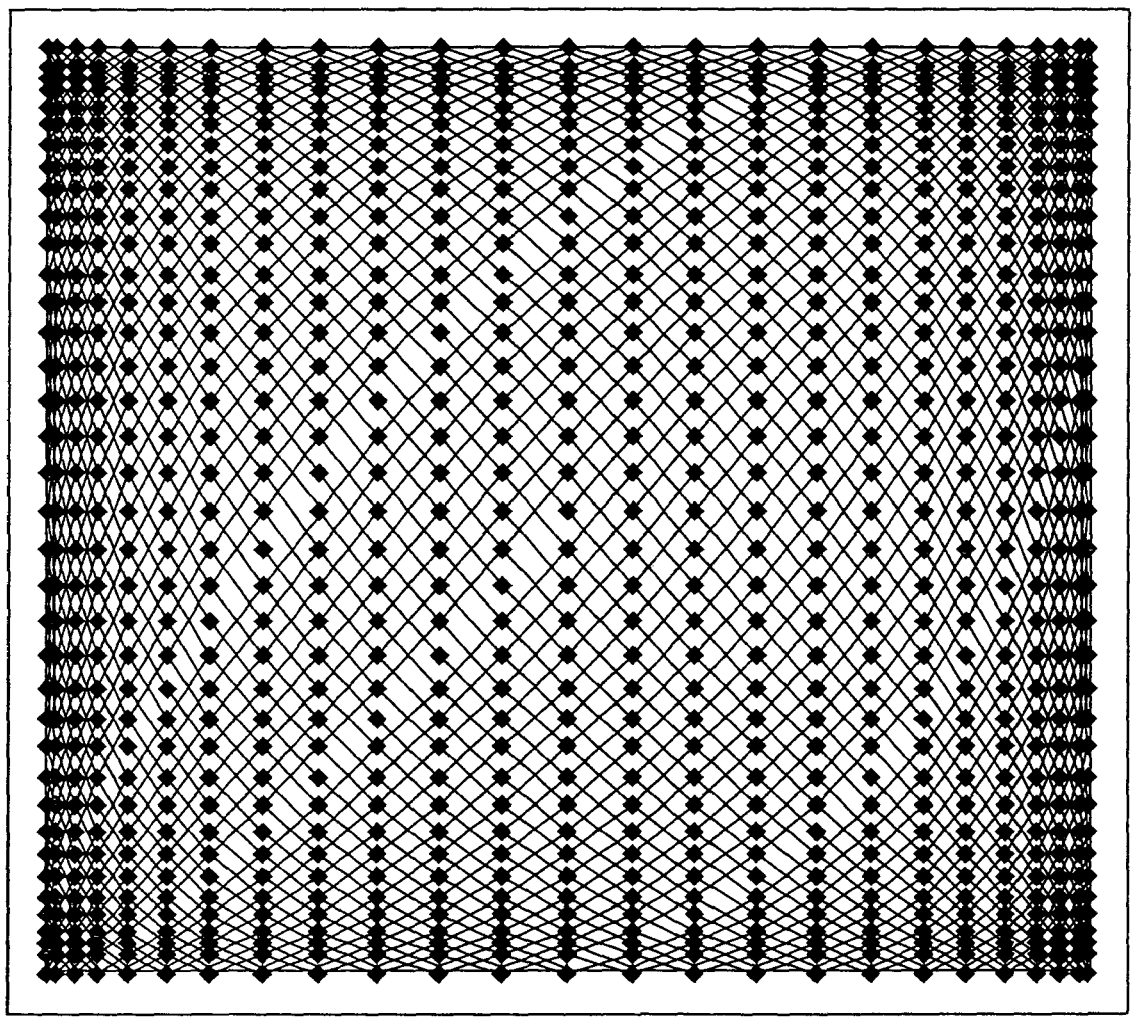
FIG. 48 is a graph showing sampling points that result from the scanning performed by continuously tracing the scanning patterns shown in FIG. 47.

FIG. 46 to FIG. 48 are concerned with a sixth embodiment of the present invention. FIG. 46 is a graph showing the waveforms of driving signals used to drive the X scanner and Y scanner at nearly identical resonant frequencies. FIG. 47 is a graph showing a pattern of scanning spots explored by the X scanner and Y scanner that are driven with the driving signals shown in FIG. 46. FIG. 48 is a graph showing sampling points attained by continuing scanning as the one shown in FIG. 47.

Conventional optical imaging systems include the one disclosed in, for example, Japanese Unexamined Patent Application Publication No. 2000-75210 and designed to use two scanners to scan Lissajous figures. However, the proposed optical imaging system has not been described about the conditions for driving scanners, the details of an operating procedure, and imaging. The present embodiment attempts to lower driving voltages by driving a plurality of scanners at resonant frequencies. Moreover, a field of view for observation is widened. The conditions for driving are designated based on characteristic information of an optical probe. Consequently, driving positional phases at which the scanners are driven can be accurately matched, and scanning can be achieved without a deviation.

According to the sixth embodiment, the X scanner 114a and Y scanner 114b are driven at nearly identical resonant frequencies. The other characteristics are identical to those of the fourth embodiment, and the description thereof will therefore be omitted. Identical components will be described with the same reference numerals assigned thereto.

Specifically, in an optical imaging system of the sixth embodiment, the driving frequency fy at which the Y scanner 114b is driven is set to a value close to but a bit different from the driving frequency fx at which the X scanner 114a is driven. For example, as shown in FIG. 46, the X scanner 114a is driven at the driving frequency of 10 kHz, and the Y scanner 114b is driven at the driving frequency of 11 kHz. In this case, the scanners make a wavy movement with every attainment of a frequency of 1 kHz.

When the positional relationship between the X scanner 114a and Y scanner 114b is traced time-sequentially, the scanners scan data to draw a scanning pattern like the one shown in FIG. 47. When, because of the wavy movements, the scanning is performed with every attainment of the frequency of 1 kHz, image data is acquired from sampling points shown in FIG. 48. The relationship between the scanning and sampling points is identical to the one described in relation to the fourth embodiment.

The control unit 135 sets the driving frequency fy of the Y scanner 114b, which is close to but a bit different from the driving frequency fx of the X scanner 114a, to a value fy0. The control unit 135 then references positional phase difference information concerning the Y scanner 114b, determines the positional phase of the driving waveform, and sets the frame rate to fx−fy.

Consequently, the number of sampling points per cycle is calculated as (fx−fy)/fs. Data items present in a range defined with an X image range Px and a Y image range Py should be acquired. Based on the data items present in the range defined with the X image range P and Y image range Py, the control unit 135 outputs a triggering signal, with which image data is acquired, to the frame grabber 136. The data is sampled only for the portion where a clock pulse is enabled.

The frame grabber 136 temporarily stores frame by frame the sampled time-sequential image data in the memory 138 on the next stage, and then outputs the data to the image engine 139. The image engine 139 uses a transformation table to transform the image data read from the memory 138 into spatially mapped data from the time-sequential data.

Thereafter, the image data transformed using the table is interpolated by the image engine 139 in the same manner as it is in the fourth embodiment, and processed for display by an image processor 140. Eventually, the resultant data is outputted to a monitor that is not shown.

Consequently, the optical imaging system of the sixth embodiment drives the Y scanner 114b at a resonant frequency close to the resonant frequency of the X scanner 114a. Therefore, the Y scanner also can acquire a high scanning amplitude in response to a low driving voltage. This means that the system can be driven with a low voltage. This results in a high frame rate and permits scanning over a wide range.

SEVENTH EMBODIMENT

Figure 49:
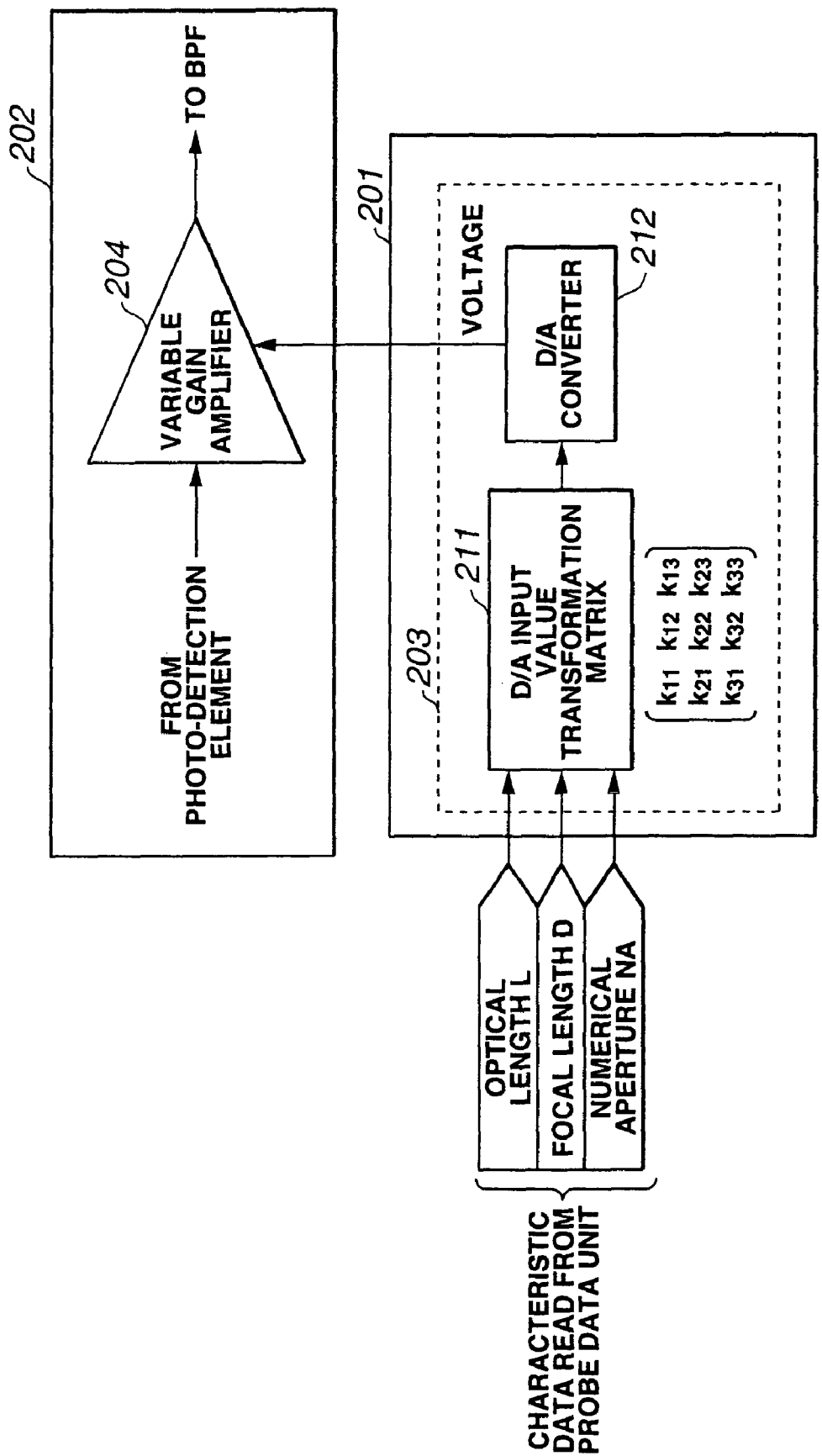
FIG. 49 is a circuit block diagram schematically showing the major portion of an optical imaging system in accordance with a seventh embodiment.
Figure 50C:
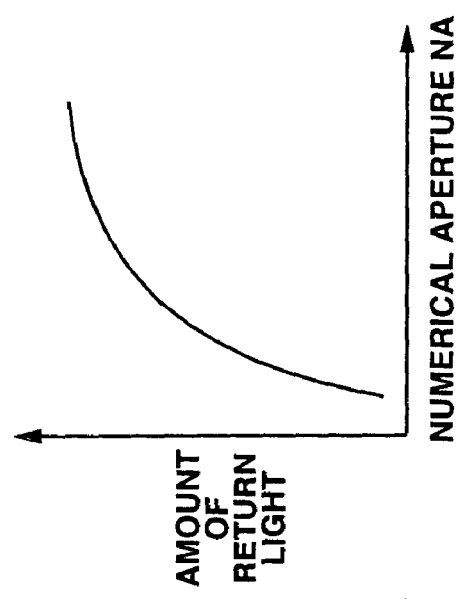
FIG. 50C is a graph showing a characteristic curve indicating an amount of return light with respect to a numerical aperture NA.
Figure 50B:
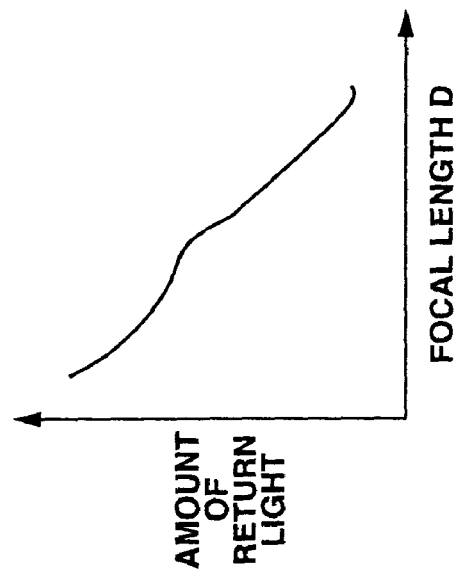
FIG. 50B is a graph showing a characteristic curve indicating an amount of return light with respect to a focal length D.
Figure 50A:
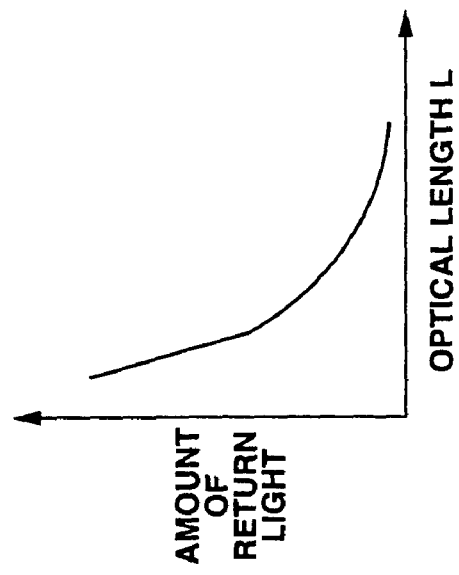
FIG. 50A is a graph showing a characteristic curve indicating an amount of return light with respect to an optical path length L.
Figure 51:
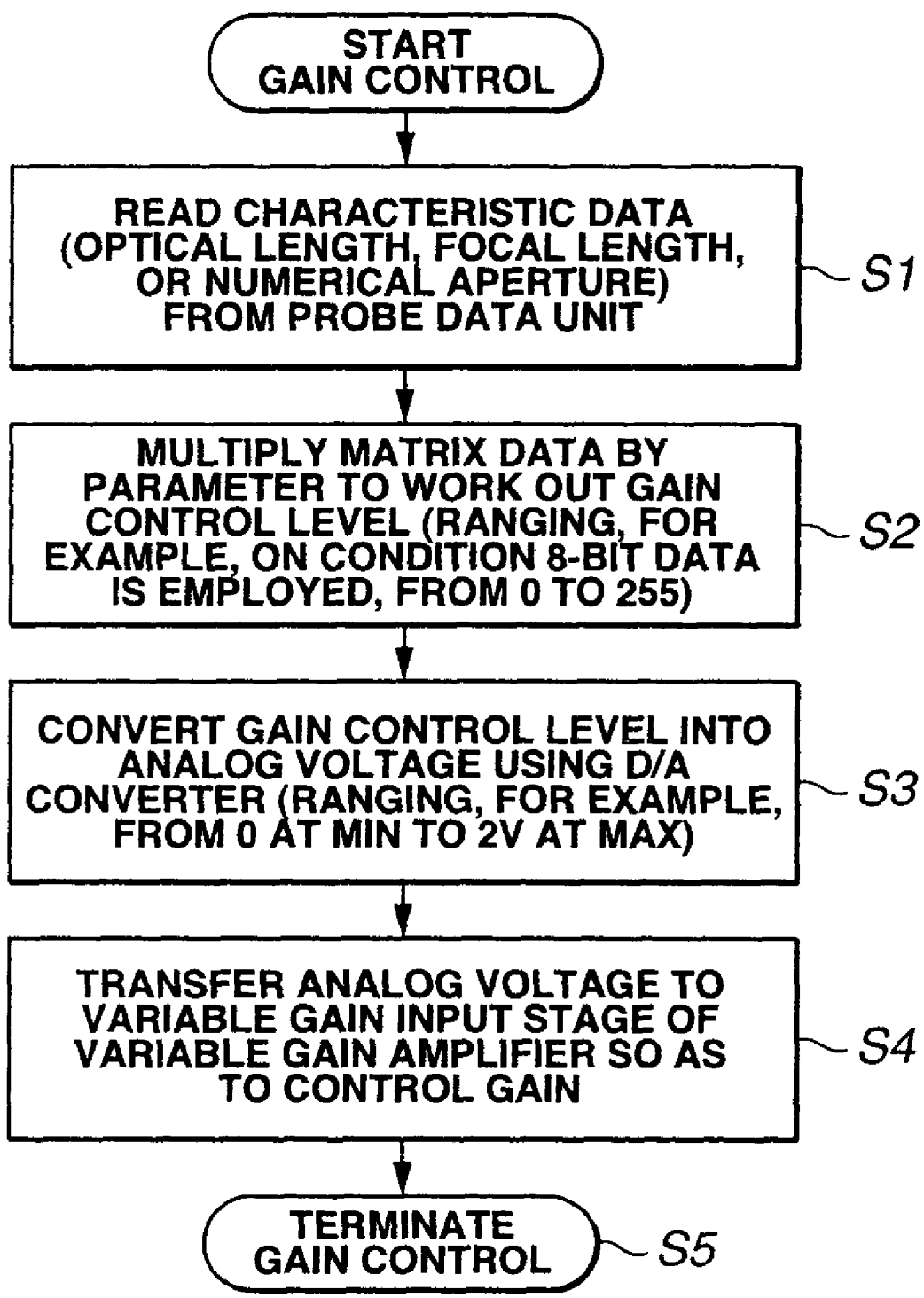
FIG. 51 is a flowchart describing gain control.
Figure 52:
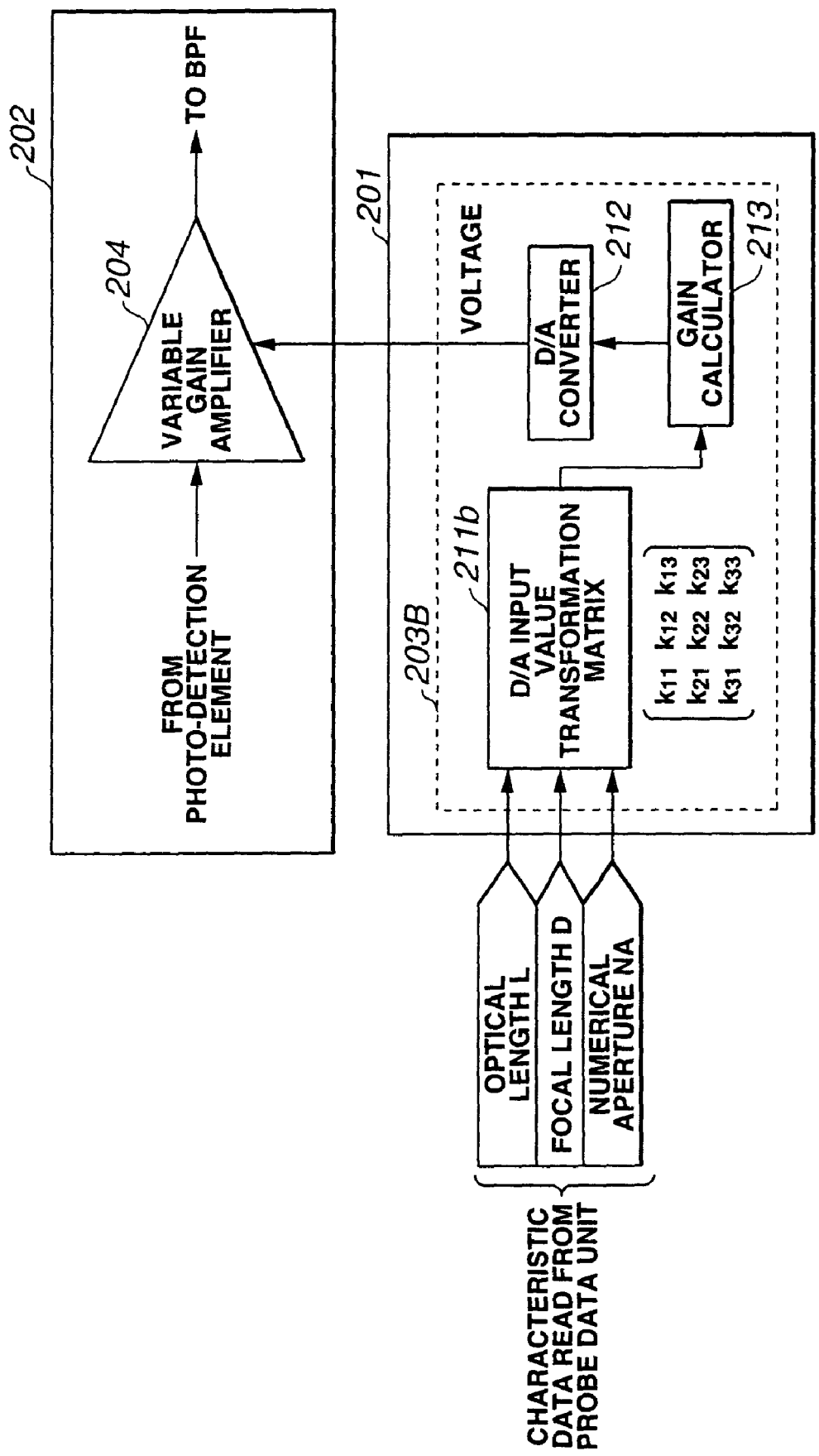
FIG. 52 is a circuit block diagram showing a variant of the optical imaging system shown in FIG. 49.
Figure 53A:
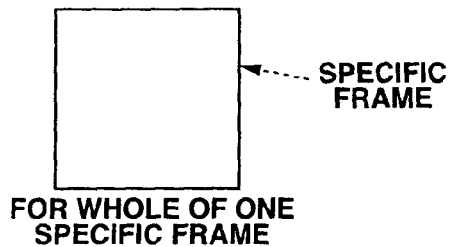
FIG. 53A is an explanatory diagram concerning a calculation mode of calculating a gain control level to be applied to data representing the whole of a specific frame.
Figure 53B:
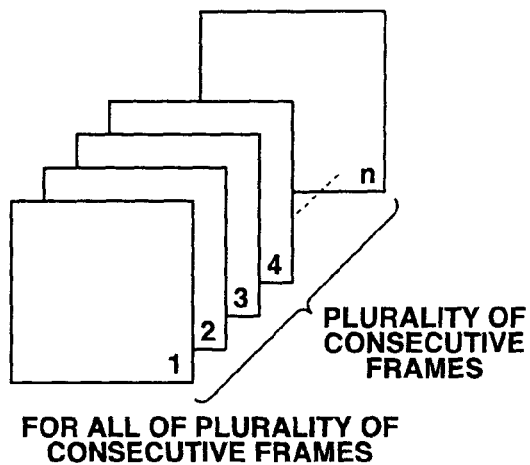
FIG. 53B is an explanatory diagram concerning a calculation mode of calculating a gain control level to be applied to data representing all of a plurality of successive frames.
Figure 53C:
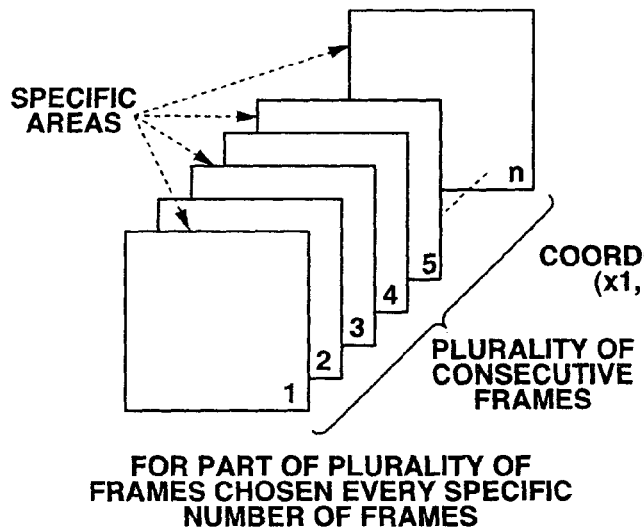
FIG. 53C is an explanatory diagram showing a calculation mode of calculating a gain control level to be applied to data representing the whole area of each frame of a plurality of frames that is chosen by every specific number of frames.
Figure 53D:
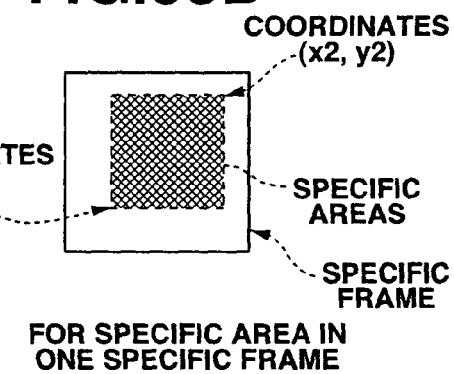
FIG. 53D is an explanatory diagram concerning a calculating mode of calculating a gain control level to be applied to data representing a specific area in a specific frame.
Figure 53E:
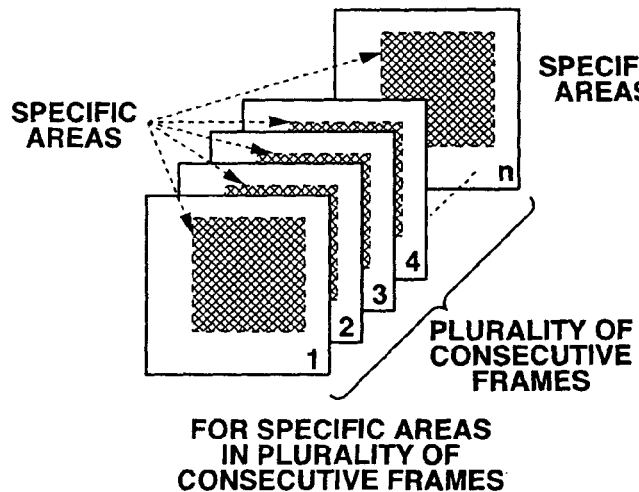
FIG. 53E is an explanatory diagram concerning a calculating mode of calculating a gain control level to be applied to data representing the specific areas in a plurality of successive frames.
Figure 53F:
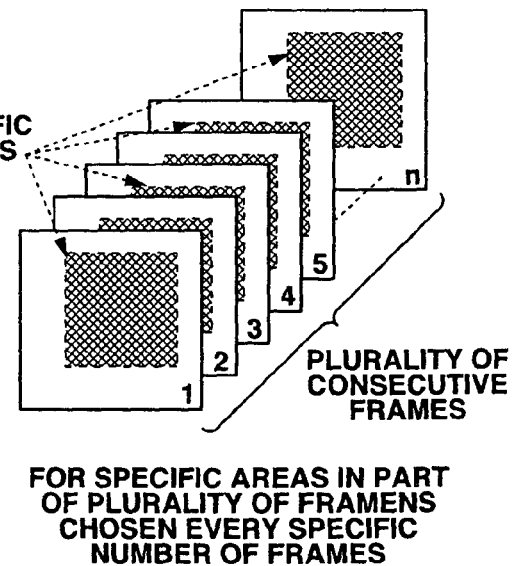
FIG. 53F is an explanatory diagram concerning a calculation mode of calculating a gain control level to be applied to data representing the specific area in every frame of a plurality of frames that is chosen by every specific number of frames.
Figure 54:
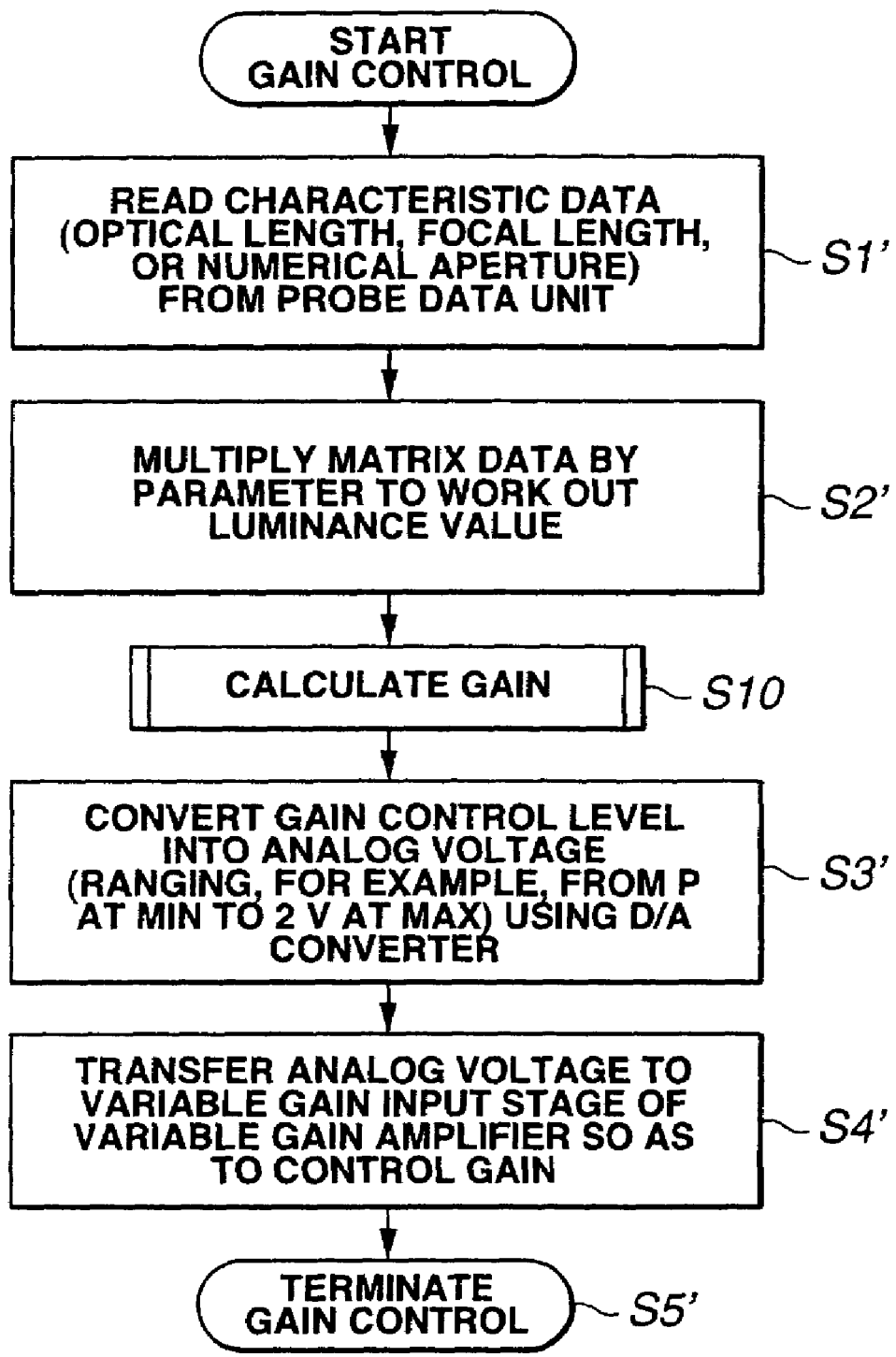
FIG. 54 is a flowchart describing gain control.
Figure 55:
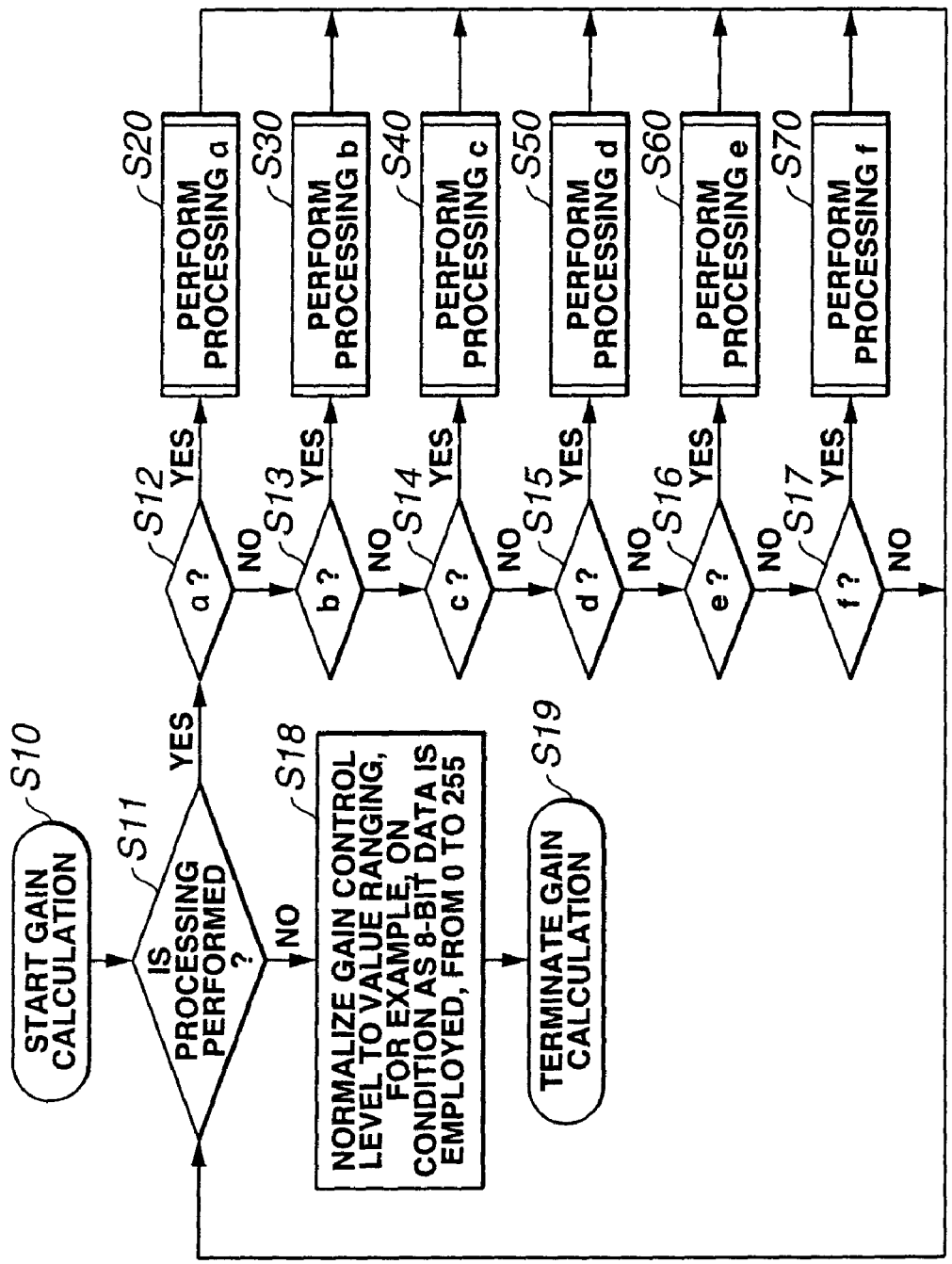
FIG. 55 is a flowchart describing gain calculation mentioned in FIG. 54.
Figure 56:
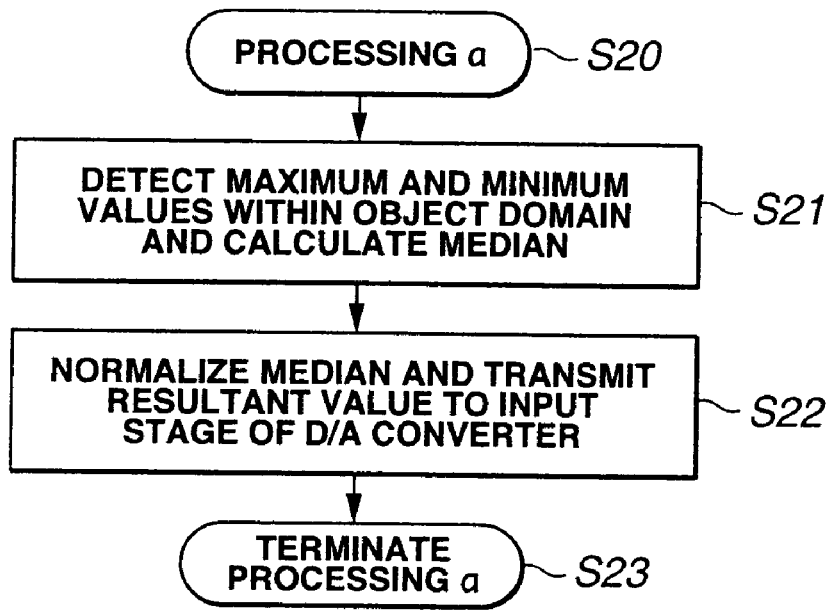
FIG. 56 is a flowchart describing processing a mentioned in FIG. 55.
Figure 57:
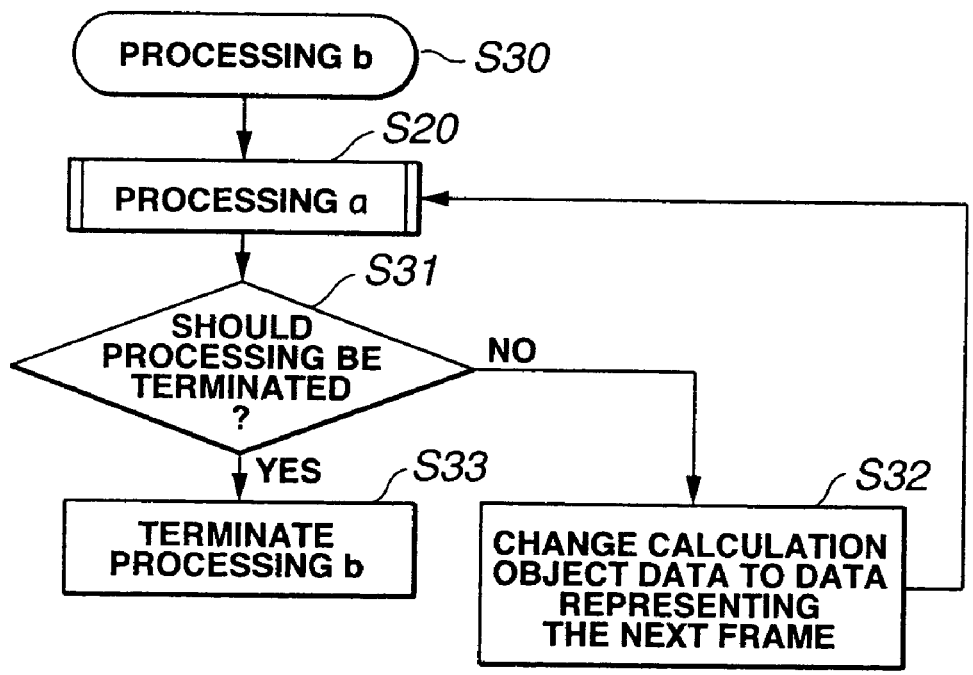
FIG. 57 is a flowchart describing processing b mentioned in FIG. 55.
Figure 58:
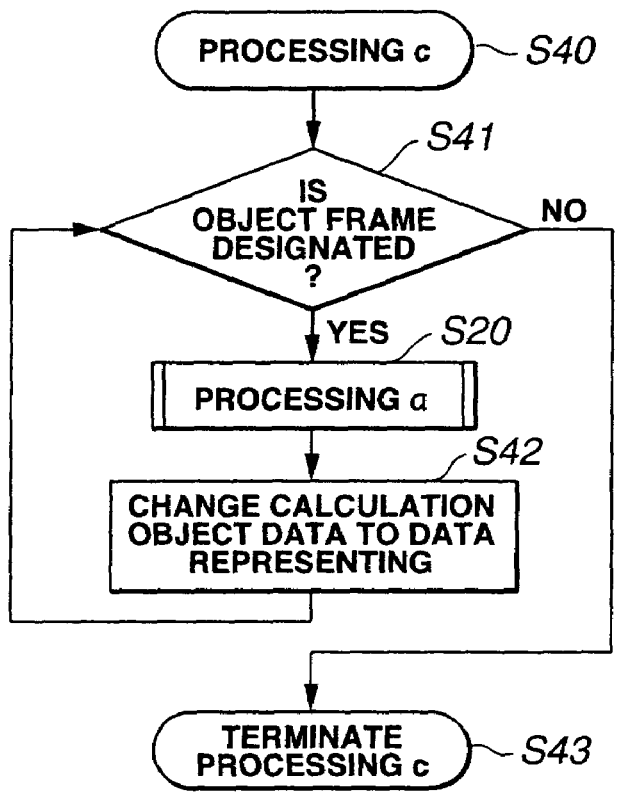
FIG. 58 is a flowchart describing processing c mentioned in FIG. 55.
Figure 59:
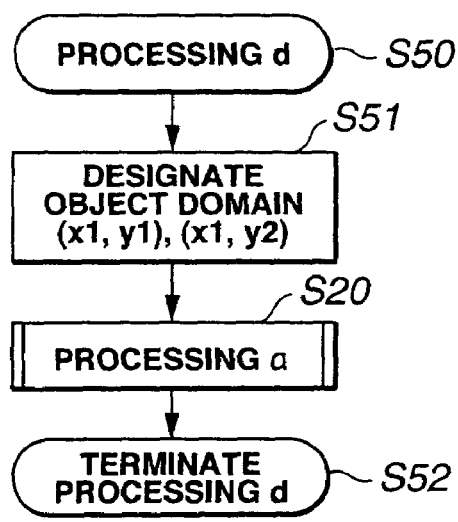
FIG. 59 is a flowchart describing processing d mentioned in FIG. 55.
Figure 60:
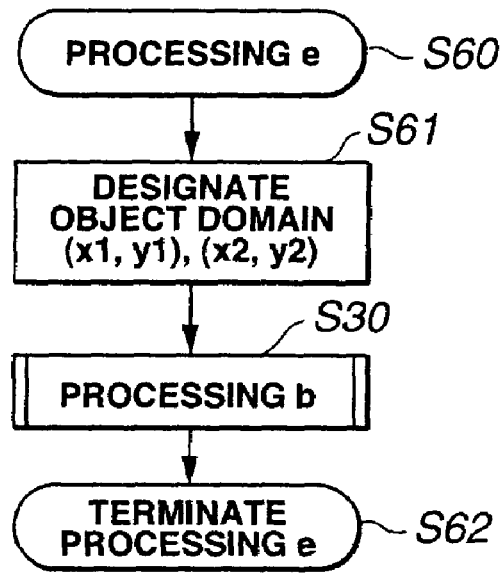
FIG. 60 is a flowchart describing processing e mentioned in FIG. 55.
Figure 61:
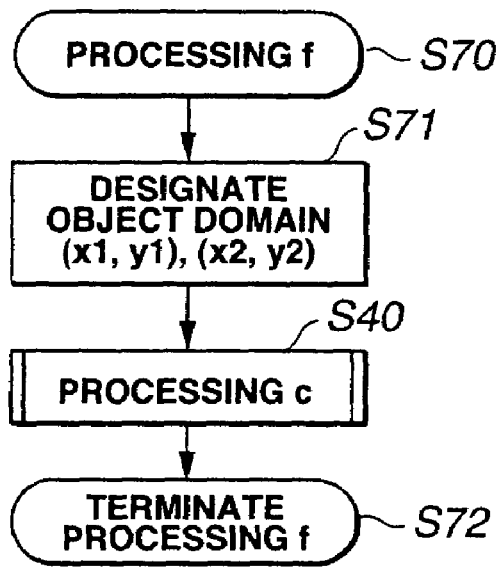
FIG. 61 is a flowchart describing processing f mentioned in FIG. 55.

FIG. 49 to FIG. 61 are concerned with a seventh embodiment of the present invention. FIG. 49 is a circuit block diagram schematically showing a major portion of an optical imaging system in accordance with the seventh embodiment. FIGS. 50A–50C include graphs showing characteristic curves that are inputted to a D/A input value transformation matrix shown in FIG. 49. FIG. 50A is a graph showing a characteristic curve indicating an amount of return light with respect to an optical path length L. FIG. 50B is a graph showing a characteristic curve indicating an amount of return light with respect to a focal length D. FIG. 50C is a graph showing a characteristic curve indicating an amount of return light versus a numerical aperture NA. FIG. 51 is a flowchart describing gain control. FIG. 52 is a circuit block diagram showing a variant of the optical imaging system shown in FIG. 49. FIGS. 53A–53F include explanatory diagrams concerning a calculation mode of calculating a gain control level. FIG. 53A is an explanatory diagram concerning a calculation mode of calculating a gain control level to be applied to data representing the whole of a specific frame. FIG. 53B is an explanatory diagram concerning a calculation mode of calculating a gain control level to be applied to data representing all of a plurality of successive frames. FIG. 53C is an explanatory diagram showing a calculation mode of calculating a gain control level to be applied to data representing the whole area of each frame of a plurality of frames that is chosen by every specific number of frames. FIG. 53D is an explanatory diagram concerning a calculation mode of calculating a gain control level to be applied to data representing a specific area in a specific frame. FIG. 53E is an explanatory diagram concerning a calculation mode of calculating a gain control level to be applied to data representing the specific areas in a plurality of successive frames. FIG. 53F is an explanatory diagram concerning a calculation mode of calculating a gain control level to be applied to data representing the specific areas in every frame of a plurality of frames that is chosen by every specific number of frames. FIG. 54 is a flowchart describing gain control. FIG. 55 is a flowchart describing gain calculation. FIG. 56 is a flowchart describing processing "a" mentioned in FIG. 55. FIG. 57 is a flowchart describing processing "b" mentioned in FIG. 55. FIG. 58 is a flowchart describing processing "c" mentioned in FIG. 55. FIG. 59 is a flowchart describing processing "d" mentioned in FIG. 55. FIG. 60 is a flowchart describing processing "e" mentioned in FIG. 55. FIG. 61 is a flowchart describing processing "f" mentioned in FIG. 55.

In the conventional optical imaging systems, the properties of return light coming from an object of observation are measured in advance, and a gain is controlled based on the properties. In the conventional optical imaging systems, the properties of return light must be measured for each optical probe whose optical characteristics are different from references. Gain control is thus labor-intensive. According to the present embodiment, even if optical probes are switched, a gain can be controlled based on information inherent to each optical probe.

According to a seventh embodiment, gain control means is included for controlling the sensitivity of a photo-detector to received light. The other characteristics are identical to those of the fourth embodiment and the description of the identical characteristics will be omitted. Components identical to those of the fourth embodiment will be described with the same reference numerals assigned thereto.

As shown in FIG. 49, the optical imaging system of the seventh embodiment has a gain controller 203, which controls the sensitivity of a photo-detector 202 to received light, incorporated in a control unit 201.

The photo-detector 202 photoelectrically converts return light propagated from the optical probe 101 to an electric signal. A variable gain amplifier 204 controls a gain to be given to the electric signal. A band-pass filter (BPF) that is not shown passes frequency components that falls within a predetermined band, and outputs the resultant signal to the frame grabber 136.

The gain controller 203 includes a D/A input value transformation matrix 211 and a D/A converter 212. The D/A input value transformation matrix 211 transforms characteristic data such as an optical path length L, a focal length D, a numerical aperture NA, or the like that are received from the probe data unit 137, into matrix data. Moreover, the D/A input value transformation matrix 211 multiplies the matrix data by a parameter to work out a gain control level that is a coefficient correction value used for gain control. The D/A converter 212 digital-to-analog (D/A) converts the gain control level calculated by the D/A input value transformation matrix 211, and outputs the resultant value as a voltage value to an input stage of the variable gain amplifier 204 included in the photo-detector.

The characteristic data received by the D/A input value transformation matrix 211 is a numerical value representing an amount of return light relevant to the optical path length L, focal length D, or numerical aperture NA as indicated with any of the graphs of FIG. 50A to FIG. 50C.

The graph shown in FIG. 50A indicates an amount of return light propagated from the optical probe 101 relative to the optical path length L. The graph shown in FIG. 50B indicates an amount of return light propagated from the optical probe 101 relative to the focal length D. The graph shown in FIG. 50C indicates an amount of return light propagated from the optical probe 101 relative to the numerical aperture (NA).

In the optical imaging system having the foregoing components, similarly to the one of the fourth embodiment, when the optical probe 101 is freely detachably attached to the main body, the probe data unit 137 is connected to the control unit 201. The control unit 201 reads data from the probe data unit 137. The control unit 201 then controls a gain to be given by the photo-detector as described in the flowchart of FIG. 51.

As described in FIG. 51, the control unit 201 reads characteristic data (specifying the optical path length L, focal length D, or numerical aperture (NA)) from the probe data unit 137 at the D/A input value transformation matrix 211 (step S1).

The control unit 201 uses the D/A input value transformation matrix 211 to transform the characteristic data into matrix data, multiplies the matrix data by a parameter, and then works out a gain control level (step S2).

The control unit 201 uses the D/A converter 212 to convert the gain control level into an analog voltage value ranging from, for example, 0 to 2 V (step S3).

Thereafter, the control unit 201 outputs the analog voltage to the variable gain input stage of the variable gain amplifier 204 included in the photo-detector, uses the variable gain amplifier 204 to control a gain (step S4), and then terminates the gain control (step S5).

Consequently, in the optical imaging system of the seventh embodiment, a gain to be given by the photo-detector can be controlled. Even when optical probes 101 are changed and the optical characteristics including the optical path length are varied, the sensitivity of the photo-detector to received light can be optimized.

In the optical imaging system of the present embodiment, the D/A converter 212 employed is of a voltage output type. Alternatively, a D/A converter 212 of a current output type or an I-V converter may be employed.

Moreover, in the optical imaging system of the present embodiment, an analog switch may be substituted for the D/A converter 212. In this case, the analog switch is used to switch resistance values, whereby an input value to the variable gain input stage of the variable gain amplifier 204 is determined.

Moreover, in the optical imaging system of the present embodiment, a general-purpose amplifier may be substituted for the variable gain amplifier 204 and designed to have a ratio of feedback resistances thereof made variable.

Incidentally, the optical imaging system may have the components shown in FIG. 52.

As shown in FIG. 52, the optical imaging system includes a D/A input value transformation matrix 211b and a gain controller 203B. The D/A input value transformation matrix 211b transforms characteristic data such as an optical path length L, a focal length D, a numerical aperture (NA), or the like that are read from the probe data unit 137, into matrix data. The D/A input value transformation matrix 211b then multiplies the matrix data by a parameter, and thus works out a luminance value. The gain controller 203B includes a gain calculator 213 that uses the obtained luminance value to work out a gain control level according to a calculation mode dependent on the number of frames or the like, and that outputs the gain control level to the D/A converter 212.

The calculation mode includes those indicated in FIG. 53A to FIG. 53F.

A calculation mode indicated in FIG. 53A is a mode of calculating a gain control level to be applied to data representing the whole area of a specific frame. A calculation mode indicated in FIG. 53B is a mode of calculating a gain control level to be applied to data representing all of a plurality of consecutive frames. A calculation mode indicated in FIG. 53C is a mode of calculating a gain control level to be applied to data representing the whole area of each frame of a plurality of frames that is chosen by every specific number of frames.

A calculation mode indicated in FIG. 53D is a mode of calculating a gain control level to be applied to data representing a specific area in a specific frame. A calculation mode indicated in FIG. 53E is a mode of calculating a gain control level to be applied to data representing specific areas in a plurality of consecutive frames. A calculation mode indicated in FIG. 53F is a mode of calculating a gain control level to be applied to data representing specific areas in each frame of a plurality of frames that is chosen by every specific number of frames.

The control unit 201 controls a gain to be given by the photo-detector by calculating a gain control level according to a calculation mode indicated in any of FIG. 53A to FIG. 53F as described in the flowchart of FIG. 54.

As described in FIG. 54, the control unit 201 reads characteristic data (an optical path length L, focal length D, or numerical aperture (NA)) from the probe data unit 137 at the data to the D/A input value transformation matrix 211b (step S1').

The control unit 201 uses the D/A input value transformation matrix 211b to transform the characteristic data into matrix data, and multiplies the matrix data by a parameter to work out a luminance value (step S2'). The control unit 201 calculates a gain as described in FIG. 55 (step S10). Thereafter, the control unit 201 uses the D/A converter 212 to convert a gain control level into an analog voltage value ranging from, for example, 0 to 2 V (step S3').

Thereafter, the control unit 201 outputs the analog voltage to the variable gain input stage of the variable gain amplifier 204 included in the photo-detector, and thus controls a gain to be given by the variable gain amplifier 204 (step S4'). The gain control is then terminated (step S5').

Next, gain calculation (step S10) to be performed by the gain calculator 213 will be described using the flowchart of FIG. 55.

As described in FIG. 55, the gain calculator 213 judges whether gain calculation is performed according to a calculation mode (step S11). If gain calculation is performed, it is judged whichever of the calculation modes is selected (step S12 to S17).

Herein, if gain calculation is not performed or none of the calculation modes is employed, the gain calculator 213 normalizes a gain control level to a value ranging, for example, on condition 8-bit data is employed, from 0 to 255 (step S18). Gain calculation is then terminated (step S19).

On the other hand, if any of the calculation modes is adopted, the gain calculator 213 performs processings "a" to "f" (steps S20 to S70) according to the adopted calculation mode. Control is then returned to step S11.

The processings "a" to "f" (steps S20 to S70) are described in the flowcharts of FIG. 56 to FIG. 61.

As described in FIG. 56, the processing "a" is to detect maximum and minimum luminance values within an object domain that corresponds to data representing the whole area of one specific frame, and calculates a median (step S21).

Thereafter, the gain calculator 213 transmits the calculated median to the D/A converter 212 (step S22), and terminates the processing a (step S23). Incidentally, the gain calculation may result in an average or a value calculated based on a luminance characteristic instead of the median. The same applies to the subsequent flowcharts.

As described in FIG. 57, the gain calculator 213 performs the processing "a", as the processing "b", on an object domain which corresponds to data representing the whole area of one specific frame (step S20). It is then judged whether the processing should be terminated (step S31). If the processing should not be terminated, calculation object data is changed to data representing the next frame-(step S32) and control is then returned to step S20. If the processing should be terminated, the gain calculator 213 terminates the processing "b" (step S33).

As described in FIG. 58, the gain calculator 213 judges as the processing "c" whether an object frame is designated (step S41). If so, the processing "a" is performed on data representing the whole area of the specific frame (step S20). Thereafter, calculation object data is changed to data representing the next frame (step S42) and control is then returned to step S20. If no object frame is specified, the gain calculator 213 terminates the processing "c" (step S43).

As described in FIG. 59, the gain calculator 213 designates as the processing "d" an object domain (x1, y1), (x2, y2) as a specific domain within data representing a specific frame (step S51), and performs the processing "a" on the designated object domain (step S20). The gain calculator 213 then terminates the processing "d" (step S52).

Moreover, as described in FIG. 60, the gain calculator 213 designates as the processing "e" an object domain (x1, y1), (x2, y2) as a specific domain within data representing one specific frame (step S61), and performs the processing "b" on the specified object domain within the data representing one frame (step S30). The gain calculator 213 then terminates the processing "e" (step S62).

As described in FIG. 61, the gain calculator 213 designates as the processing "f" an object domain (x1, y1), (x2, y2) as a specific domain within data representing a specific frame (step S71), and then performs the processing "c" on the specified object domain within the data representing the specific frame (step S40). The gain calculator 213 then terminates the processing "f" (step S72).

Consequently, the optical imaging system of the present variant provides the same advantages as the one of the seventh embodiment. In addition, gain calculation is performed according to a calculation mode dependent on the number of frames or the like. Eventually, the sensitivity of the photo-detector to received light can be optimized.

EIGHTH EMBODIMENT

Figure 62:
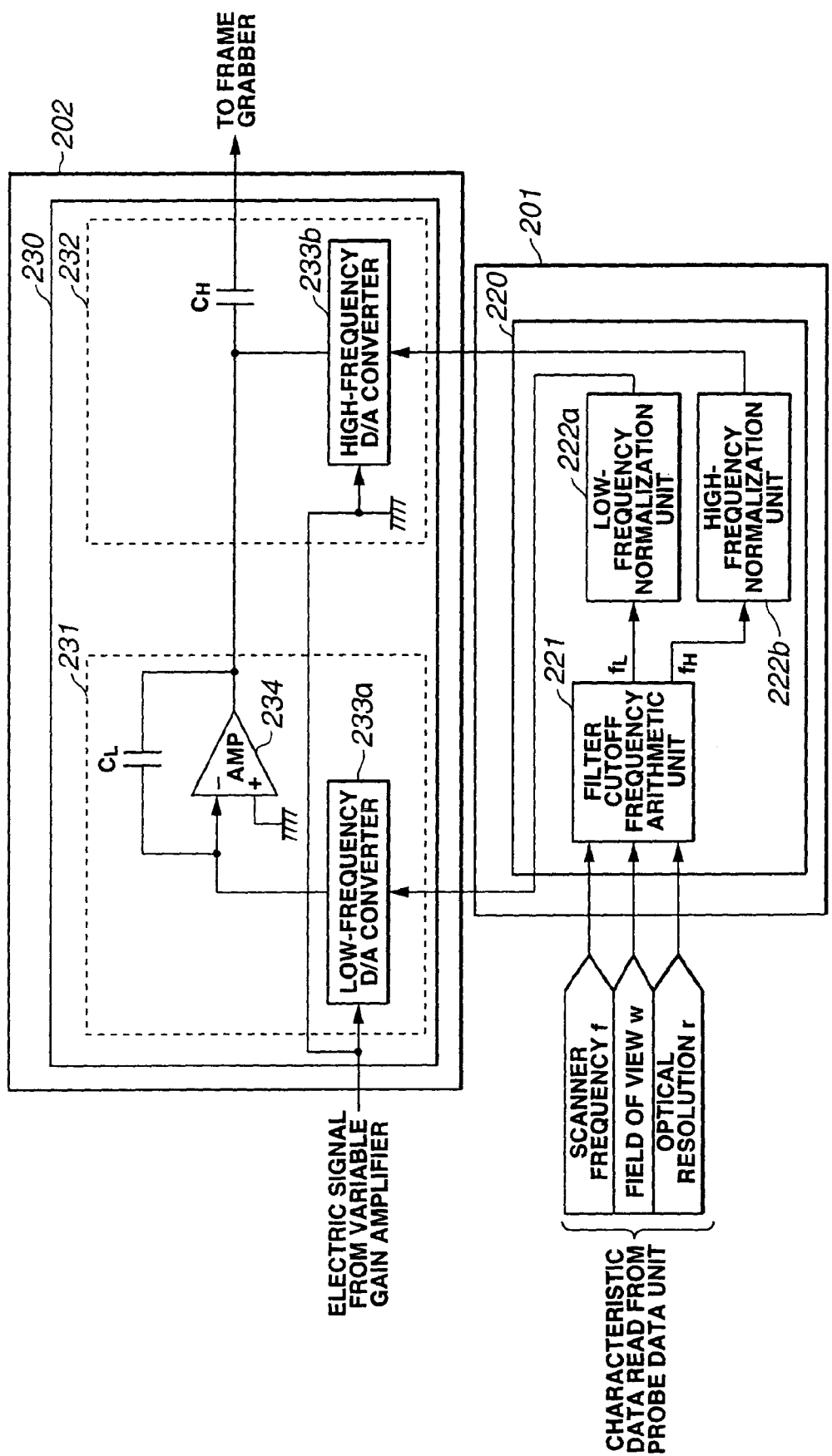
FIG. 62 is a circuit block diagram schematically showing the major portion of an optical imaging system in accordance with an eighth embodiment.
Figure 63:
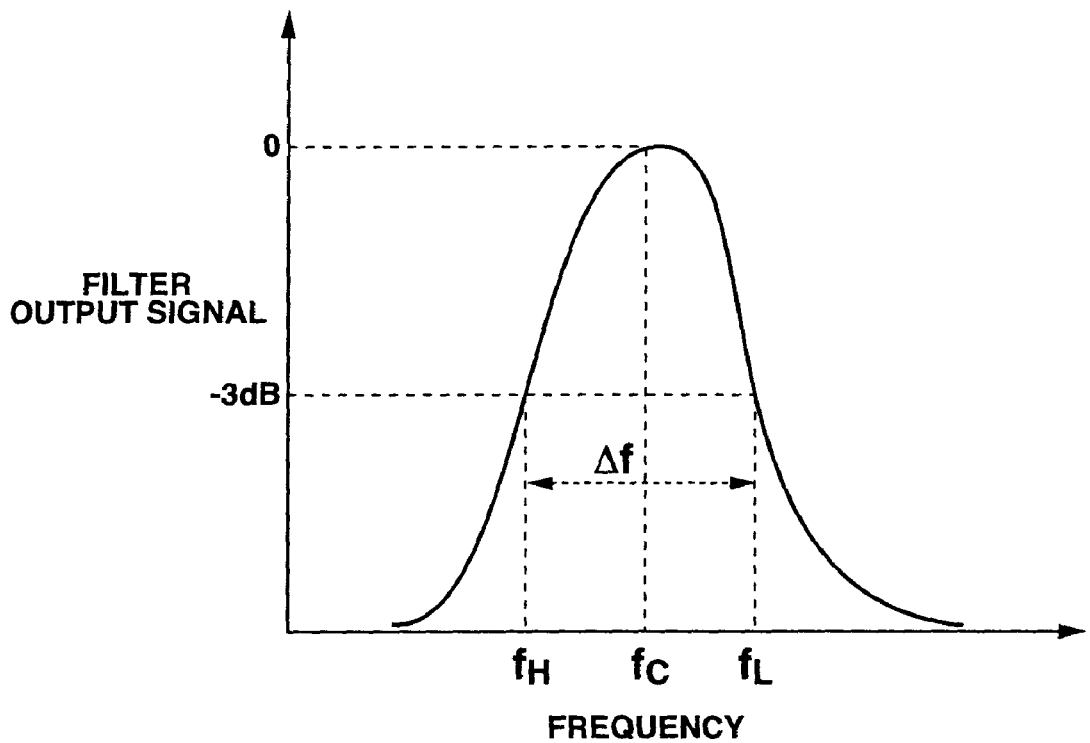
FIG. 63 is a graph indicating a frequency characteristic of a band-pass filter (BPF) included in the major portion shown in FIG. 62.

FIG. 62 to FIG. 65 are concerned with an eighth embodiment of the present invention. FIG. 62 is a circuit block diagram schematically showing a major portion of an optical imaging system in accordance with the eighth embodiment. FIG. 63 is a graph indicating the frequency characteristic of a band-pass filter (BPF) shown in FIG. 62.

Figure 65:
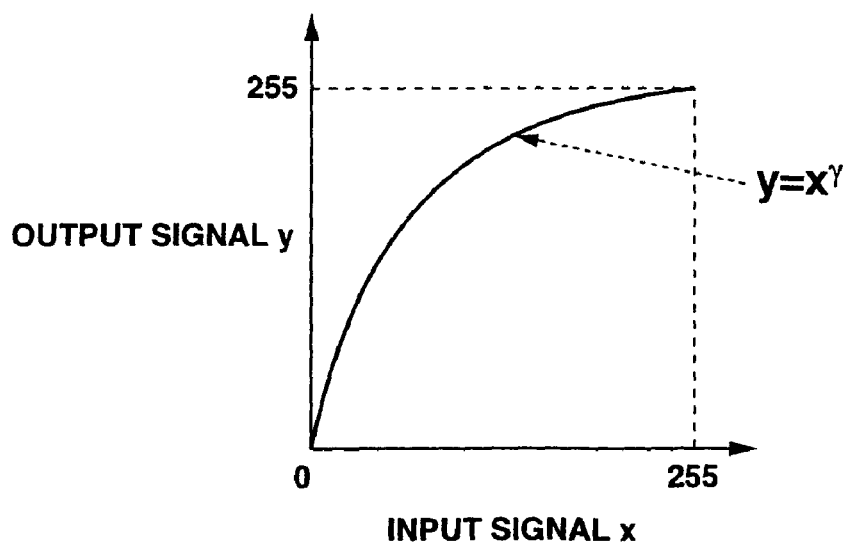
FIG. 65 is a graph of an output signal y versus an input signal x implying gamma correction.

FIG. 64 is a flowchart describing filter adjustment. FIG. 65 is a graph concerning correction of a gamma indicated in an output signal y in relation to that indicated in an input signal x.

The eighth embodiment includes a filter adjusting means that regulates the cutoff frequency of a photo-detector. The other characteristics are identical to those of the fourth embodiment, and the description of the identical characteristics is omitted. A description will proceed with the same reference numerals assigned to identical components.

In the conventional optical imaging systems, an object of observation is observed, and a band limitation filter is regulated manually. Thus, a frequency band is optimized. For this reason, in the conventional optical imaging systems, every time optical probes whose optical characteristics are different from references are changed, or every time observation is performed using the same optical probe, the frequency band must be regulated. The present embodiment includes a band adjusting means that even when optical probes are changed, can regulate a frequency band according to information inherent to each optical probe. Thus, the present embodiment can automatically regulate a frequency band of signal components that can pass through an optical probe.

As shown in FIG. 62, an optical imaging system of the eighth embodiment has a filter regulator 220, which regulates the cutoff frequency of the photo-detector 202, included in the control unit 201.

In the photo-detector 202, similarly to the one included in the fourth embodiment, the photo-detection element 117 photoelectrically converts return light propagated from the optical probe 101 into an electric signal. The variable gain amplifier 204 described in relation to the seventh embodiment controls a gain to be given to the electric signal. The band-pass filter (BPF) 230 passes frequency components, which fall within a predetermined frequency band, and outputs the resultant signal to the frame grabber 136.

The band-pass filter 230 includes a low-pass filter (LPF) 231 and a high-pass filter (HPF) 232. The low-pass filter 231 cuts off the low-frequency components of the electric signal, which is received from the variable gain amplifier 204, according to coefficient data (normalization value) sent from the filter regulator 220. The high-pass filter 232 cuts off, like the low-pass filter 231, the high-frequency components of the electric signal, which has the low-frequency components thereof cut off by the low-pass filter 231, according to coefficient data (normalization value) sent from the filter regulator 220.

The low-pass filter 231 includes a low-frequency D/A converter 233*a*, an I-V converter 234, and a capacitor $C_L$. The low-frequency D/A converter 233*a* digital-to-analog (D/A) converts the electric signal received from the variable gain amplifier 204, and outputs a current proportional to the coefficient data (normalization value) sent from the filter regulator 220. The I-V converter 234 current-to-voltage (I-V) converts the current received from the low-frequency D/A converter 233*a*. The capacitor $C_L$ passes only the low-frequency components of the current received from the I-V converter 234.

The high-pass filter 232 includes a high-frequency D/A converter 233*b* and a capacitor $C_H$. The high-frequency D/A converter 233*b* digital-to-analog converts the electric signal received from the variable gain amplifier 204, and outputs a current proportional to the coefficient data (normalization value) sent from the filter regulator 220. Based on the current received from the high-frequency D/A converter 233*b*, the capacitor $C_H$ passes the high-frequency components of the electric signal that has the low-frequency components thereof cut off by the low-pass filter 231.

The filter regulator 220 includes a filter cutoff frequency arithmetic unit 221, a low-frequency normalization unit 222*a*, and a high-frequency normalization unit 222*b*. The filter cutoff frequency arithmetic unit 221 calculates a low-pass filter cutoff frequency $f_L$ and a high-pass filter cutoff frequency $f_H$ from characteristic data specifying a scanner driving frequency f (X driving frequency $V_X$ and Y driving frequency $V_Y$), field of view w (X field of view $l_X$ and Y field of views $l_Y$), and an optical resolution r. The low-frequency normalization unit 222*a* normalizes the low-pass filter cutoff frequency $f_L$ calculated by the filter cutoff frequency arithmetic unit 221, and transmits the resultant value as the coefficient data used to regulate the cutoff frequency of the low-pass filter. The high-frequency normalization unit 222*b* normalizes the high-pass filter cutoff frequency $f_H$ calculated by the filter cutoff frequency arithmetic unit 221, and transmits the resultant value as the coefficient data used to regulate the cutoff frequency of the high-pass filter.

Now, the band-pass filter 230 exhibits the frequency characteristic like the one shown in, for example, FIG. 63.

As shown in FIG. 63, the frequency characteristic is graphically expressed with the Gaussian distribution.

The center frequency fc of an output of the band-pass filter 230 is expressed using the field of view w, scanner driving frequency f, and optical resolution r as follows:

$$fc = 2 \times w \times f/r \qquad (27)$$

Therefore, the bandwidth Δf of the output of the band-pass filter 230 is expressed as follows:

$$\Delta f = 0.882 \times fc \qquad (28)$$

The center frequency fc and bandwidth Δf are used to calculate the low-pass filter cutoff frequency $f_L$ and high-pass filter cutoff frequency $f_H$. The coefficients 2 and 0.882 employed in calculation of the center frequency fc and bandwidth Δf can be varied properly.

In the optical imaging system having the foregoing components, similarly to the one of the fourth embodiment, when the optical probe 101 is freely detachably attached to the main body, the probe data unit 137 is connected to the control unit 201. The control unit 201 reads data from the probe data unit 137. The control unit 201 then performs filter adjustment (cutoff frequency adjustment) on the photo-detector as described in the flowchart of FIG. 64.

As described in FIG. 64, in the control unit 201, the filter cutoff frequency arithmetic unit 221 reads the characteristic data (scanner driving frequency f, field of view w, or optical resolution r) from the probe data unit 137 (step S81). In the control unit 201, the filter cutoff frequency arithmetic unit 221 calculates the center frequency fc of an output of the band-pass filter 230 (step S82).

Thereafter, in the control unit 201, the filter cutoff frequency arithmetic unit 221 calculates the bandwidth Δf of the output of the band-pass filter 230 from the center frequency fc (step S83).

In the control unit 201, the filter cutoff frequency arithmetic unit 221 calculates the low-pass filter cutoff frequency $f_L$ using the center frequency fc and bandwidth Δf (step S84), and also calculates the high-pass filter cutoff frequency $f_H$ (step S85).

Thereafter, the control unit 201 normalizes the low-pass filter cutoff frequency $f_L$ to a value ranging from, for example, on condition 8-bit data is employed, 0 to 255 so that the low-pass filter cutoff frequency $f_L$ will be equal to a cutoff frequency $1/(2\pi R_L C_L)$ determined with the resistance of an internal resistor $R_L$ included in the low-frequency D/A converter 233*a* and the capacitance of the capacitor $C_L$ included therein (step S86). Moreover, the high-pass filter cutoff frequency $f_H$ is normalized to a value ranging from, for example, on condition 8-bit data is employed, 0 to 255 so that it will be equal to a cutoff frequency $1/(2\pi R_H C_H)$ determined with the resistance of an internal resistor $R_H$ included in the high-pass D/A converter 233b and the capacitance of the capacitor $C_H$ included therein (step S87).

Thereafter, the control unit 201 inputs the electric signal, which is sent from the variable gain amplifier 204, to the reference voltage input stage of the low-frequency D/A converter 233a included in the low-pass filter 231. The control unit 201 then instructs the low-frequency D/A converter 233a to transmit a current proportional to the normalized value of the low-pass filter cutoff frequency $f_L$ to the I-V converter 234 (step S88).

The I-V converter 234 current-to-voltage (I-V) converts the current received from the low-frequency D/A converter 233a. The capacitor $C_L$ passes the low-frequency components of the current received from the I-V converter 234 and outputs the resultant current to the capacitor $C_H$ included in the band-pass filter 230 (step S89). The capacitor $C_H$ passes only the high-frequency components of the electric signal received from the capacitor $C_L$, and outputs the resultant signal to the frame grabber 136 (step S90). Then, filter adjustment is terminated (step S91).

Consequently, in the optical imaging system of the eighth embodiment, even when optical probes 101 are changed, filter adjustment (cutoff frequency adjustment) can be optimized.

In the optical imaging system of the present embodiment, the employed D/A converter 212 is of a current output type. Alternatively, a voltage output type D/A converter 212 and an analog multiplier may be used to vary a gain to be given by the I-V converter 234. Thus, the cutoff frequency may be regulated.

Moreover, the optical imaging system of the present embodiment may not include the D/A converter 212. Instead, an analog switch is used to switch resistances so as to regulate the cutoff frequency.

In the optical imaging system of the present embodiment, the internal resistor R and capacitor C included in the D/A converter 212 constitute a filter. Alternatively, a combination of the internal resistor R and a coil L or a combination of the internal resistor R, coil L, and capacitor C will do. The I-V converter 234 may be included or excluded. Anyhow, a known filter will do.

In the conventional optical imaging systems, a predetermined gamma relative to an object of observation is calculated in advance. A measured gamma is corrected based on the calculated value. Therefore, in the conventional optical imaging systems, every time optical probes whose optical characteristics are different from references are changed, a gamma must be measured and controlled. An image signal producing means is therefore included for correcting a gamma according to information inherent to each optical probe even when optical probes are changed.

In short, a signal sent from the frame grabber 136 to the image engine 139 via the memory 138 has a gamma component thereof corrected using a function shown in FIG. 65. An image is then displayed on the display surface of a monitor that is not shown.

The gamma correction is performed using the following function of an output signal y to an input signal x expressed in the graph of FIG. 65:

$$y = x^\gamma \tag{29}$$

Incidentally, the gamma value has the relationship of $0 \leq \gamma \leq 1$. A value calculated in advance in order to permit optimal image display based on a signal representing living-body information, for example, a value of 0.45 is adopted.

Moreover, in FIG. 65, signal data represents a gray-scale level (ranging from 0 to 255) with eight bits. Alternatively, the data may be able to represent a higher gray-scale level.

The embodiments of the present invention have been described so far. Noted is that the present invention is not limited to the embodiments. Needless to say, the present invention can be modified in various manners without a departure from the gist of the invention.

INDUSTRIAL APPLICABILITY

According to the present invention, feature information of a connected optical probe is automatically detected or checked. Consequently, a connected optical probe can be driven or controlled suitably to a scanning technique implemented therein, a light path can be adjusted suitably, or a display image can be adjusted optimally.

The invention claimed is:

1. An optical imaging system for irradiating light that emanates from a light source and constructing an observed image of an object according to information of return light received from the object, said optical imaging system comprising:
    a replaceable optical probe for propagating the light, which emanates from said light source, to an object, and receiving return light from the object;
    a device main body including a light receiving means that receives return light from said light source and object, and converts the light into an electric signal, and having said optical probe freely detachably attached thereto;
    a detecting means for detecting the characteristics of an optical probe attached to said main body;
    a designating means for designating the conditions for controlling an optical probe according to the characteristics of the optical probe detected by said detecting means; and
    at least one of a focal range, a focal position and a numerical aperture of the optical probe being included in the characteristics of the optical probe.

2. The optical imaging system according to claim 1, further comprising:
    at least one scanning means for scanning light that emanates from said light source;
    signal generating means for driving said scanning means and generating a timing signal;
    storage means on which characteristic information of optical probes is recorded;
    an optical system for irradiating light, which emanates from said light source, to an object, and introducing return light received from the object to said light receiving means;
    memory means in which an electric signal sent from said light receiving means is stored;
    image signal producing means for transforming data stored in said memory means so as to produce an image signal; and
    control means for changing at least one of the settings of said image signal producing means and the settings of said signal generating means according to data read from said memory means.

3. The optical imaging system according to claim 2, wherein said scanning means, said storage means, and at least part of said optical system are included in said optical probe; and said optical probe is freely detachably attached to at least one of said image signal producing means and said signal generating means.

4. The optical imaging system according to claim 2 or 3, wherein the information stored in said storage means includes at least one of a driving frequency at which at least one scanner is driven, a driving voltage, an offset voltage, and an imaging range.

5. The optical imaging system according to claim 3, wherein the information stored in said storage means includes at least one of a type of probe and a serial number thereof.

6. The optical imaging system according to claim 2, wherein said control means designates data for said signal generating means according to information stored in said storage means.

7. The optical imaging system according to claim 6, wherein the data designated for said signal generating means is the amplitude of a driving waveform with which said scanning means is driven.

8. The optical imaging system according to claim 6, wherein the data designated for said signal generating means is the frequency of a driving waveform with which said scanning means is driven.

9. The optical imaging system according to claim 6, wherein the data designated for said signal generating means is the waveform of a driving waveform with which said scanning means is driven.

10. The optical imaging system according to claim 6, wherein said signal generating means includes a clock generator, and the data designated for said signal generating means is a clock frequency at which a signal is generated by said clock generator.

11. The optical imaging system according to claim 6, wherein the data designated for said signal generating means is the timing of a triggering signal outputted to said memory means.

12. The optical imaging system according to claim 2, wherein said scanning means is driven at a mechanical resonant frequency.

13. The optical imaging system according to claim 12, wherein two or more scanning means are included, and the beat frequency of the frequencies at which the two or more scanning means are driven is different from a frame rate.

14. The optical imaging system according to claim 2, further comprising a gain control means for controlling the sensitivity of said light receiving means to received light.

15. The optical imaging system according to claim 14, wherein said control means designates data for said gain control means according to information stored in said storage means.

16. The optical imaging system according to claim 15, wherein the data designated for said gain control means is an amount of return light received by said light receiving means.

17. The optical imaging system according to claim 16, wherein said amount of return light is determined with at least an optical path length relevant to said optical system, a focal length, and a numerical aperture of a lens.

18. The optical imaging system according to claim 14, wherein said gain control means includes a gain calculator for calculating a correction value according to the amount of return light.

19. The optical imaging system according to claim 18, wherein said gain control means includes a gain calculator that calculates a correction value according to a luminance value specified in data representing a specific area in at least one frame of an image.

20. The optical imaging system according to claim 18, wherein said gain control means calculates a luminance value using data representing each frame of an image, and feeds back the luminance value for display of the next frame.

21. The optical imaging system according to claim 18, wherein said gain control means calculates a luminance value using data representing at least a specific frame, and feeds back the luminance value for display of the next and subsequent frames.

22. The optical imaging system according to claim 2, further comprising a filter adjusting means for adjusting the frequency band of an electric signal to be transmitted to said memory means.

23. The optical imaging system according to claim 22, wherein said control means designates data for said filter adjusting means according to information stored in said storage means.

24. The optical imaging system according to claim 23, wherein the data designated for said filter adjusting means specifies a driving frequency at which said scanning means is driven and a resolution offered by said optical system.

25. An optical imaging system for irradiating light that emanates from a light source and constructing an observed image of an object according to information of return light received from the object, said optical imaging system comprising:
  a replaceable optical probe for propagating the light, which emanates from said light source, to an object, and receiving return light from the object;
  a device main body including a light receiving means that receives return light from said light source and object, and converts the light into an electric signal, and having said optical probe freely detachably attached thereto;
  a detecting means for detecting the characteristics of an optical probe attached to said main body;
  a designating means for designating the conditions for controlling an optical probe according to the characteristics of the optical probe detected by said detecting means;
  at least one scanning means for scanning light that emanates from said light source;
  signal generating means for driving said scanning means and generating a timing signal;
  storage means on which characteristic information of optical probes is recorded;
  an optical system for irradiating light, which emanates from said light source, to an object, and introducing return light received from the object to said light receiving means;
  memory means in which an electric signal sent from said light receiving means is stored;
  image signal producing means for transforming data stored in said memory means so as to produce an image signal; and
  control means for changing at least one of the settings of said image signal producing means and the settings of said signal generating means according to data read from said memory means, wherein said image signal producing means includes an interpolating means.

26. The optical imaging system according to claim 25, wherein said control means designates data for said interpolating means according to information stored in said storage means.

27. An optical imaging detection method for irradiating light that emanates from a light source and constructing an observed image of an object according to information of return light received from the object, wherein:

said optical imaging detection method is implemented in an optical imaging system comprising: a replaceable optical probe for propagating light, which emanates from said light source, to an object and receiving return light from the object; a light receiving means for receiving return light from said light source and object, and converting the light into an electric signal; a main body to which said optical probe can be freely detachably attached; and a detecting means for detecting the characteristics of an optical probe attached to said main body;

the conditions for controlling an optical probe are designated based on the characteristics of the optical probe detected by said detecting means; and at least one of a focal range, a focal position and a numerical aperture of the optical probe being included in the characteristics of the optical probe.

28. The optical imaging detection method according to claim 27, comprising:

a reading step for reading data from a storage means;

a calculating step for calculating the conditions for controlling said optical probe according to the data read at said reading step;

a designating step for designating the conditions for control calculated at said calculating step;

a controlling and driving step for controlling and driving said optical probe according to the conditions for control designated at said designating step; and a displaying-processing step for displaying an image according to image data acquired by an optical probe driven at said controlling and driving step.

* * * * *